United States Patent
Young et al.

(10) Patent No.: US 7,442,777 B2
(45) Date of Patent: Oct. 28, 2008

(54) CYTOTOXICITY MEDIATION OF CELLS EVIDENCING SURFACE EXPRESSION OF CD63

(75) Inventors: David S. F. Young, Toronto (CA); Helen P. Findlay, Toronto (CA); Susan E. Hahn, Toronto (CA); Luis A. G. da Cruz, Toronto (CA); Daad Sayegh, Mississauga (CA); Kristian Rogers, Georgetown (CA); Shankar Kumar, Pleasanton, CA (US); Paul Hinton, Sunnyvale, CA (US)

(73) Assignee: Arius Research Inc., Toronto, Ontario (CA)

( * ) Notice: Subject to any disclaimer, the term of this patent is extended or adjusted under 35 U.S.C. 154(b) by 0 days.

(21) Appl. No.: 11/362,452

(22) Filed: Feb. 24, 2006

(65) Prior Publication Data

US 2007/0025912 A1 Feb. 1, 2007

Related U.S. Application Data

(63) Continuation-in-part of application No. 11/321,624, filed on Dec. 29, 2005, and a continuation-in-part of application No. 10/810,751, filed on Mar. 26, 2004, now Pat. No. 7,361,343, which is a continuation-in-part of application No. 10/603,006, filed on Jun. 23, 2003, which is a continuation-in-part of application No. 10/348,231, filed on Jan. 21, 2003, now Pat. No. 7,009,040, and a continuation-in-part of application No. 09/727,361, filed on Nov. 29, 2000, now Pat. No. 6,657,048.

(51) Int. Cl.
*C07K 16/00* (2006.01)
*C07K 17/00* (2006.01)
(52) U.S. Cl. .................. 530/388.1; 530/391.1
(58) Field of Classification Search .......... None
See application file for complete search history.

(56) References Cited

U.S. PATENT DOCUMENTS

| | | | |
|---|---|---|---|
| 4,172,124 A | 10/1979 | Koprowski et al. |
| 4,861,581 A | 8/1989 | Epstein et al. |
| 4,867,973 A | 9/1989 | Goers et al. |
| 5,171,665 A | 12/1992 | Hellstrom et al. |
| 5,296,348 A | 3/1994 | Rakowicz-Szulczynsk |
| 5,484,596 A | 1/1996 | Hanna, Jr. et al. |
| 5,693,763 A | 12/1997 | Codington et al. |
| 5,750,102 A | 5/1998 | Eisenbach et al. |
| 5,780,033 A | 7/1998 | Torchillin et al. |
| 5,783,186 A | 7/1998 | Arakawa et al. |
| 5,849,876 A | 12/1998 | Linsley et al. |
| 5,869,045 A | 2/1999 | Hellstrom et al. |
| 5,869,268 A | 2/1999 | Kudo et al. |
| 6,180,357 B1 | 1/2001 | Young et al. |
| 6,245,898 B1 | 6/2001 | Testa et al. |
| 6,657,048 B2 | 12/2003 | Young et al. |
| 6,783,961 B1 | 8/2004 | Edwards et al. |
| 6,783,969 B1 | 8/2004 | Tang et al. |
| 7,009,040 B2 | 3/2006 | Young et al. |
| 2001/0003777 A1 | 6/2001 | Young et al. |
| 2001/0009665 A1 | 7/2001 | Young et al. |
| 2002/0102638 A1 | 8/2002 | Rosen et al. |
| 2003/0055220 A1 | 3/2003 | Legrain |
| 2003/0148408 A1 | 8/2003 | Frantz et al. |
| 2003/0211498 A1 | 11/2003 | Morin et al. |
| 2004/0105816 A1 | 6/2004 | Young et al. |
| 2004/0141913 A1 | 7/2004 | Young et al. |
| 2004/0141915 A1 | 7/2004 | Young et al. |
| 2004/0141979 A1 | 7/2004 | Young et al. |
| 2004/0197328 A1 | 10/2004 | Young et al. |
| 2004/0198651 A1 | 10/2004 | Klammer et al. |
| 2004/0258693 A1 | 12/2004 | Young et al. |

FOREIGN PATENT DOCUMENTS

| | | |
|---|---|---|
| CN | 1326951 | 12/2001 |
| CN | 1326962 | 12/2001 |
| CN | 1351054 | 5/2002 |
| CN | 1364803 | 8/2002 |
| EP | 1 033 401 | 6/2000 |
| WO | WO9520401 | 8/1995 |
| WO | WO 99/66027 | 12/1999 |
| WO | WO 00/05918 | 2/2000 |
| WO | WO 00/55180 | 9/2000 |

(Continued)

OTHER PUBLICATIONS

Ellis et al, J Immunol, Jul. 1995, 155(2):925-937.*
M. Adachi et al, "Novel staging protocol for non-small-cell lung cancers according to MRP-1/CD9 and KAII/CD82 gene expression", J. Clin. Oncol., 16(4):1397-1406 (Apr. 1998).
G. Andreola et al, "Induction of lymphocyte apoptosis by tumor cell secretion of FasL-bearing microvesicles", J. Exp. Med., 195(10):1303-1316 (May 2002).
B. Atkinson et al, "Monoclonal antibody to a highly glycosylated protein reacts in fixed tissue with melanoma and other tumors", Hybridoma, 4(3):243-255 (1985).

(Continued)

*Primary Examiner*—Misook Yu
*Assistant Examiner*—Sean Aeder
(74) *Attorney, Agent, or Firm*—McHale & Slavin, P.A.

(57) ABSTRACT

This invention relates to the diagnosis and treatment of cancerous diseases, particularly to the mediation of cytotoxicity of tumor cells; and most particularly to the use of cancerous disease modifying antibodies (CDMAB), optionally in combination with one or more chemotherapeutic agents, as a means for initiating the cytotoxic response. The invention further relates to binding assays which utilize the CDMAB of the instant invention.

5 Claims, 40 Drawing Sheets
(3 of 40 Drawing Sheet(s) Filed in Color)

FOREIGN PATENT DOCUMENTS

| | | |
|---|---|---|
| WO | WO 01/75177 | 10/2001 |
| WO | WO 02/00677 | 1/2002 |
| WO | WO 02/55551 | 7/2002 |
| WO | WO 02/057303 | 7/2002 |
| WO | WO 02/070539 | 9/2002 |
| WO | WO 03/016475 | 2/2003 |
| WO | WO 03/055515 | 7/2003 |
| WO | WO 03/057160 | 7/2003 |
| WO | WO 03/068268 | 8/2003 |
| WO | WO 03/070902 | 8/2003 |
| WO | WO 03/086 456 | 10/2003 |
| WO | WO 2004/041170 | 5/2004 |

OTHER PUBLICATIONS

D. Azorsa et al, "A general approach to the generation of monoclonal antibodies against members of the tetraspanin superfamily using recombinant GST fusion proteins", J. Immunol. Meth., 229:35-48 (1999).

M. Barrio et al, "A new epitope on human melanoma-associated antigen CD63/ME491 expressed by both primary and metastatic melanoma", Hybridoma, 17(4):355-364 (1998).

M. Barrio et al, "Monoclonal antibody FC-5.01, directed against CD63 antigen, is internalized into cytoplasmic vesicles in the IIB-BR-G human breast cancer cell line", Hybridoma, 17(6):517-523 (1998).

F. Berditchevski et al, "Characterization of integrin-tetraspanin adhesion complexes: role of tetraspanins in integrin signaling", J. Cell Biol., 146(2):477-492 (Jul. 1999).

F. Berditchevski et al, "A novel link between integrins, transmembrane-4 superfamily proteins (CD63 and CD81), and phosphatidylinositol 4-kinase", J. Biol. Chem., 272(5):2595-2598 (Jan. 1997).

F. Berditchevski et al, "Specific association of CD63 with the VLA-3 and VLA-6 integrins", J. Biol. Chem., 270(30):17784-17790 (Jul. 1995).

D. Blakey et al, "Antitumor activity of the novel vascular targeting agent ZD6126 in a panel of tumor models", Clinical Cancer Research, 8:1974-1983 (Jun. 2002).

A. Carmo et al, "Association of the transmembrane 4 superfamily molecule CD53 with a tyrosine phosphatase activity", Eur. J. Immunol., 25:2090-2095 (1995).

C. Claas et al, "Evaluation of prototype transmembrane 4 superfamily protein complexes and their relation to lipid rafts", J. Biol. Chem., 276(11):7974-7984 (Mar. 2001).

D. Demetrick et al, "ME491 melanoma-associated glycoprotein family: antigenic identity of ME491, NKI/C-3, neuroglandular antigen (NGA), and CD63 proteins", J. Natl Cancer Inst, 84(6):422-429 (Mar. 1992).

G. Eckhardt et al, "Developmental therapeutics: successes and failures of clinical trial designs of targeted compounds", in American Society of Clinical Oncology, pp. 209-219 (2003).

A. Engering et al, "Association of distinct tetraspanins with MHC class II molecules at different subcellular locations in human immature dendritic cells", International Immunology, 13(2):127-134 (2001).

J-M. Escola et al, "Selective enrichment of tetraspan proteins on the internal vesicles of multivesicular endosomes and on exosomes secreted by human B-lymphocytes", J. Biol. Chem., 273(32):20121-20127 (Aug. 1998).

S. Guichard et al, "Schedule-dependent activity of topotecan in OVCAR-3 ovarian carcinoma xenograft: pharmacokinetic and pharmacodynamic evaluation", Clinical Cancer Research, 7:3222-3228 (Oct. 2001).

N. Guilbaud et al, "Marked antitumor activity of a new potent acronycine derivative in orthotopic models of human solid tumors", Clinical Cancer Research, 7:2573-2580 (Aug. 2001).

C. Hammond et al, "The tetraspan protein CD82 is a resident of MHC class II compartments where it associates with HLA-DR, -DM, and -DO molecules", J. Immunol, 161:3282-3291 (1998).

J. Hildreth et al, "Characterization of a novel self-associating Mr 40,000 platelet glycoprotein", Blood, 77(1):121-132 (Jan. 1991).

S. Hirschfeld et al, "Oncology drug development: United States Food and Drug Administration perspective", Critical Reviews in Oncology/Hematology, 42:137-143 (2002).

H. Hotta et al, "Genomic structure of the ME491/CD63 antigen gene and functional analysis of the 5'-flanking regulatory sequences", Biochem Biophys Res Comm, 185(1):436-442 (May 1992).

H. Hotta et al, "Molecular cloning and characterization of an antigen associated with early stages of melanoma tumor progression", Cancer Research, 48:2955-2962 (Jun. 1988).

H. Hotta et al, "Overexpression of the human melanoma-associated antigen ME491 patially suppresses in vivo malignant phenotypes of H-ras-transformed NIH3T3 cells in athymic nude mice", Melanoma Research, 1:125-132 (1991).

C. Huang et al, "Correlation of reduction in MRP-1/CD9 and KAI1/CD82 expression with recurrences in breast cancer patients", Am J Pathol, 153(3):973-983 (Sep. 1998).

H-I. Jang et al, "A decrease in the expression of CD63 tetraspanin protein elevates invasive potential of human melanoma cells", Experimental and Molecular Medicine, 35(4):317-323 (Aug. 2003).

C. Joyner et al, "Identification and enrichment of human osteoprogenitor cells by using differentiation stage-specific monoclonal antibodies", Bone, 21(1):1-6 (Jul. 1997).

T. Karpanen et al, "Vascular endothelial growth factor C promotes tumor lymphangiogenesis and intralymphatic tumor growth", Cancer Research, 61:1786-1790 (Mar. 2001).

S. Kennel et al, "Monoclonal antibody to rat CD63 detects different molecular forms in rat tissue", Hybridoma, 17(6):509-515 (1998).

G. Klement et al, "Differences in therapeutic indexes of combination metronomic chemotherapy and an anti-VEGFR-2 antibody in multidrug-resistant human breast cancer xenografts", Clinical Cancer Research, 8:221-232 (Jan. 2002).

T. Kobayashi et al, "The tetraspanin CD63/lamp3 cycles between endocytic and secretory compartments in human endothelial cells", Molecular Biology of the Cell, 11:1829-1843 (May 2000).

M. Kondoh et al, "Decreased expression of human melanoma-associated antigen ME491 along the progression of melanoma precanceroses to invasive and metastatic melanomas", Melanoma Research, 3:241-245 (1993).

Y. Koyama et al, "A novel monoclonal antibody induces the differentiation of monocyte leukemic cells", Biochem Biophys Res Comm, 168(3):898-904 (May 1990).

Y. Koyama et al, "CD63, a member of tetraspan transmembrane protein family, induces cellular spreading by reaction with monoclonal antibody on substrata", Biochem Biophys Res Comm, 246(3):841-846 (1998).

S. Lebel-Binay et al, "CD82, member of the tetra-span-transmembrane protein family, is a costimulatory protein for T cell activation", J. Immunol., 155:101-110 (1995).

J. Li et al, "Recombinant CD63/ME491/neuroglandular/NKI/C-3 antigen inhibits growth of established tumors in transgenic mice", J. Immunol., 171:2922-2929 (2003).

B. Mannion et al, "Transmembrane-4 superfamily proteins CD81 (TAPA-1), CD82, CD63, and CD53 specifically associate with integrin alpha4beta1 (CD49d/CD29)", J. Immunol., 157:2039-2047 (1996).

T. Martin, "Phosphoinositide lipids as signaling molecules: common themes for signal transduction, cytoskeletal regulation, and membrane trafficking", Annu. Rev. Cell Dev. Biol., 14:231-264 (1998).

M. Martinez-Lorenzo et al, "Unusual intracellular trafficking of salmonella typhimurium in human melanoma cells", Cellular Microbiology, 3(6):407-416 (2001).

M. Metzelaar et al, "CD63 antigen", J. Biol. Chem., 266(5):3239-3245 (Feb. 1991).

H. Nieuwenhuis et al, "Studies with a monoclonal antibody against activated platelets: evidence that a secreted 53,000-molecular weight lysosome-like granule protein is exposed on the surface of activated platelets in the circulation", Blood, 70(3):838-845 (Sep. 1987).

H. Okochi et al, "Expression of tetra-spans transmembrane family (CD9, CD37, CD53, CD63, CD81 and CD82) in normal and neoplastic human keratinocytes: an association of CD9 with alpha3beta1 integrin", British Journal of Dermatology, 137:856-863 (1997).

K. Olson et al, "Inhibition of prostate carcinoma establishment and metastatic growth in mice by an antiangiogenin monoclonal antibody", Int. J. Cancer, 98:923-929 (2002).

P. Peters et al, "Cytotoxic T lymphocyte granules are secretory lysosomes, containing both perforin and granzymes", J. Exp. Med., 173:1099-1109 (May 1991).

K. Radford et al, "CD63 associates with transmembrane 4 superfamily members, CD9 and CD81, and with beta1 integrins in human melanoma", Biochem Biophys Res Comm, 222:13-18 (1996).

K. Radford et al, "Regulation of tumor cell motility and migration by CD63 in a human melanoma cell line", J. Immunol., 158:3353-3358 (1997).

K. Radford et al, "Suppression of human melanoma cell growth and metastasis by the melanoma-associated antigen CD63 (ME491)", Int. J. Cancer, 62:631-635 (1995).

E. Rubinstein et al, "CD9, CD63, CD81, and CD82 are components of a surface tetraspan network connected to HLA-DR and VLA integrins", Eur. J. Immunol., 26:2657-2665 (1996).

G. Sauer et al, "Expression of tetraspanin adaptor proteins below defined threshold values is associated with in vitro invasiveness of mammary carcinoma cells", Oncology Reports, 10:405-410 (2003).

Z. Si et al, "Expression of the neuroglandular antigen and analogues in melanoma, CD9 expression appears inversely related to metastatic potential of melanoma", Int. J. Cancer, 54:37-43 (1993).

L. Sikora et al, "Characterization of a novel neuroglandular antigen (NGA) expressed on abnormal human melanocytes", Int. J. Cancer, 39:138-145 (1987).

P. Sincock et al, "Localization of the transmembrane 4 superfamily (TM4SF) member PETA-3 (CD151) in normal human tissues: comparison with CD9, CD63, and alpha5beta1 integrin", J. Histochem Cytochem, 45:515-525 (1997).

K. Skubitz et al, "CD63 associates with CD11/CD18 in large detergent-resistant complexes after translocation to the cell surface in human neutrophils", FEBS Letters, 469:52-56 (2000).

K. Skubitz et al, "CD63 associates with tyrosine kinase activity and CD11/CD18, and transmits an activation signal in neutrophils", J. Immunol., 157:3617-3626 (1996).

P. Smith et al, "Anti-interleukin-6 monoclonal antibody induces regression of human prostate cancer xenografts in nude mice", The Prostate, 48:47-53 (2001).

R. Stephen et al, "A novel oestrogen-regulated gene in human breast cancer cells identified by differential display", J. Mol. Endocrin., 20:375-380 (1998).

V. Toothill et al, "Characterization of the enhanced adhesion of neutrophil leukocytes to thrombin-stimulated endothelial cells", J. Immunol., 145(1):283-291 (Jul. 1990).

P. Therasse et al, "New guidelines to evaluate the response to treatment in solid tumors", Journal of the National Cancer Institute, 92(3):205-216 (Feb. 2000).

B. Ulbricht et al, "Influence of 12(S)-hydroxyeicosatetraenoic acid (12(S)-HETE) on the localization of cathepsin B and cathepsin L in human lung tumor cells", Eur J Cell Biol, 74:294-301 (Nov. 1997).

C. Vennegoor et al, "Circulating melanoma-associated antigen detected by monoclonal antibody NKI/C-3", Cancer Immunol Immunother, 23:93-100 (1986).

V. Von Gruenigen et al, "Efficacy of intraperitoneal adenovirus-mediated p53 gene therapy in ovarian cancer", Int. J. Gynecol. Cancer, 9:365-372 (1999).

M. Wang et al, "An ocular melanoma-associated antigen", Arch Ophthalmol., 110:399-404 (1992).

W. Waud et al, "Characterization of in vivo mammary and prostate tumor xenograft models for growth and response to clinical anticancer agents", Contrib Oncol Basel Karger, 54:305-315 (1999).

Z. Xiao et al, "Generation of a baculovirus recombinant prostate-specific membrane antigen and its use in the development of a novel protein biochip quantitative immunoassay", Protein Expresion and Purification, 19:12-21 (2000).

R. Yauch et al, "Specific interactions among transmembrane 4 superfamily (TM4SF) proteins and phospholinositide 4-kinase", Biochem. J., 351:629-637 (2000).

A. Zannettino et al, "A powerful new technique for isolating genes encoding cell surface antigens using retroviral expression cloning", J. Immunol., 156:611-620 (1996).

A. Zannettino et al, "Molecular cloning of the cell surface antigen identified by the osteoprogenitor-specific monoclonal antibody, HOP-26", J. Cell. Biochem., 89:56-66 (2003).

Paus et al., "Mapping Epitopes and Antigenicity by Site-Directed Masking", PNAS (2006), vol. 103, No. 24, pp. 9172-9177.

Badger et al., "Prospects for Monoclonal Antibody Therapy of Leukemia and Lymphoma", Cancer (1986), vol. 58, pp. 584-589.

Begg et al., "Rapid Fluorence-Based Assay for Radiosensitivity and Chemosensitivity Testing in Mammalian Cells in Vitro", Cancer Research (1989), vol. 49, pp. 565-569.

Boven et al., "Monoclonal Antibodies in Cancer Treatment: Where Do We Stand After 10 Years?", Radiotherapy and Oncology (1986), vol. 5, pp. 109-117.

Costa et al., "Implications of Disaggregation Procedures on Biological Representation of Human Solid Tumours", Cell Tissue Kinet. (1987), vol. 20, pp. 171-180.

Dairkee et al., "Partial Enzymatic Degradation of Stroma Allows Enrichment and Expansion of Primary Breast Tumor Cells", Cancer Research (1997), vol. 57, pp. 1590-1596.

Dillman, "Antibodies as Cytotoxic Therapy", J. Clin. Oncol. (1994), vol. 12, No. 7, pp. 1497-1515.

Dillman, "Monoclonal Antibodies for Treating Cancer", Annals of Internal Medicine (1989), vol. 111, pp. 592-603.

Disis et al., "HER-2/neu Protein: A Target for Antigen-Specific Immunotherapy of Human Cancer", Advances in Cancer Research (1997), vol. 71, pp. 343-371.

Dvorak et al., "Structure of Solid Tumors and Their Vasculature: Implications for Therapy with Monoclonal Antibodies", Cancer Cells (1991), vol. 3, pp. 77-85.

Engelholm et al., "Disaggregation of Human Solid Tumours by Combined Mechanical and Enzymatic Methods", Br. J. Cancer (1985), vol. 51, pp. 93-98.

Epstein et al., "Two New Monoclonal Antibodies, Lym-1 and Lym-2, Reactive with Human B-Lymphocytes and Derived Tumors, With Immunodiagnostic and Immunotherapeutic Potential", Cancer Research (1987), vol. 47, pp. 830-840.

Foon, "Biological Therapy of Cancer", Breast Cancer Research & Treatment (1986), vol. 7, pp. 5-14.

Drexler, "Recent Results on the Biology of Hodgkin and Reed-Sternberg Cells", Leukemia and Lymphoma (1993), vol. 9, pp. 1-25.

Embleton, "Monoclonal Antibodies to Osteogenic Sarcoma Antigens", Immunol. Ser. (1984), vol. 23, pp. 181-207.

Freshney, "Culture of Animal Cells", a Manual of Basic Technique (1983), Alan R. Liss, Inc., New York, p. 3.

Gura, "Systems for Identifying New Drugs are Odten Faulty", Science (1997), vol. 278, pp. 1041-1042.

Dermer, "Another Anniversary for the War on Cancer", Bio/Technology (1994), vol. 12, p. 320.

Curti, "Physical Barriers to Drug Delivery in Tumors", Critical Reviews in Oncology/Hermatology (1993), vol. 14, pp. 29-39.

Hartwell et al., "Integrating Genetic Approaches into the Discovery of Anticancer Drugs", Science (1997), vol. 278, pp. 1064-1068.

Hsu, "Karyology of Cells in Culture - A Preparation and Analysis of Karyotypes and Idiograms", in Tissue Culture Methods and Applications (1973), eds. Kruse and Patterson, Academic Press, New York, pp. 764-767.

Franzen et al., "Nonenzymatic Extraction of Cells from Clinical Tumor Material for Analysis of Gene Expression by Two-Dimensional Polyacrylamide Gel Electrophoresis", Electrophoresis (1993), vol. 14, pp. 1045-1053.

Holz et al., "Antibody-Based Immunotherapeutic Strategies in Colorectal Cancer", Recent Results in Cancer Research (1996), vol. 142, pp. 381-400.

Cruse et al., Illustrated Dictionary of Immunology (1995), CRC Press, p. 280.

Knuth et al., "ADCC Reactivity of Human Melanoma Cells with Mouse Monoclonal Antibodies", Proc. Am. Assoc. Cancer Res. (1984), vol. 25, p. 1005, Abstract Only.

Kravtsov et al., "Automated Monitoring of Apoptosis in Suspension Cell Cultures", Laboratory Investigation (1996), vol. 74, No. 2, pp. 557-570.

Horoszewicz et al., "Monoclonal Antibodies to a New Antigenic Marker in Epithelial Prostatic Cells and SErum of Prostatic Cancer Patients ", Anticancer Research (1987), vol. 7, pp. 927-936.

Herlyn et al., "Monoclonal Anticolon Carcinoma Antibodies in Complement-Dependent Cytotoxicity", Int. J. Cancer (1981), vol. 27, pp. 769-774.

Harris et al., "Serotherapy of Cancer", Seminars in Oncology (1989), vol. 16, No. 3, pp. 180-198.

Baselga et al., "Phase II Study of Weekly Intravenous Recombinant Humanized Anti-p185HER2 Monoclonal Antibody in Patients with HER2/neu-Overexpressing Metastatic Breast Cancer", Journal of Clinical Oncology (1996), vol. 14, pp. 737-744.

Winter et al., "Humanized Antibodies", TIPS (1993), vol. 14, pp. 139-143.

Co et al., "Humanized Antibodies for Therapy", Nature (1991), vol. 351, pp. 501-502.

Campbell et al., "Biology: 5th Edition", 1999, p. 856.

Jain, "Barriers to Drug in Solid Tumors", Scientific American (1994), vol. 271, No. 1, pp. 58-65.

Presta et al., "Engineering Therapeutic Antibodies for Improved Function", Biochemical Society Transactions (2002), vol. 30, Part 4, pp. 487-490.

Chatterjee et al., "Idiotypic Antibody Immunotherapy of Cancer", Cancer Immunol. Immunother. (1994), vol. 38, pp. 75-82.

Weiner, "An Overview of Monoclonal Antibody Therapy of Cancer", Seminars in Oncology (1999), vol. 26, No. 4, Suppl. 12, pp. 41-50.

Seaver, "Monoclonal Antibodies in Industry: More Difficult Than Originally Thought", Genetic Engineering News (1994), vol. 14, No. 14, pp. 10 and 21.

Shak et al., "Overview of the Trastuzumab (Herceptin) Anti-HER2 Monoclonal Antibody Clinical Program in HER2-Overexpessing Metastatic Breast Cancer", Seminars in Oncology (1999), vol. 26, No. 4, Suppl. 12, pp. 71-77.

Tannock et al., "The Basic Science of Oncology: Second Edition", McGraw-Hill, Inc. (1992), Chapter 11, p. 399.

Colbleigh et al., "Multinational Study of the Efficacy and Safety of Humanized Anti-HER2 Monoclonal Antibody in Women Who Have HER2-Overexpressing Metastatic Breast Cancer That Has Progressed After Chemotherapy for Metastatic Disease", Journal of Clinical Oncology (1999), vol. 17, pp. 2639-2648.

Hellstrom et al., "Antitumor Effects of L6, an IgG2a Antibody that Reacts with Most Human Carcinomas", Proc. Natl. Acad. Science (1986), vol. 83, pp. 7059-7063.

Taber's Cyclopedia Medical Dictionary (1985), F.A. Davis Company, Philadelphia, p. 274.

Buskens et al., "Adenocarcinomas of the Gastro-Esophageal Junction: A Comparative Study of the Gastric Cardia and the Esophagus with Respect to Cyclooxygenase-2 Expression", Digestive Disease Week Abstracts and Itinerary Planner (2003), Abstract No. 850.

Krontiris et al., "Internal Medicine: Fourth Edition", Elsevier Science (1994), Chapters 71-72, pp. 699-729.

Carter et al., "Chemotherapy of Cancer: Second Edition", John Wiley & Sons (1981), New York, Appendix C.

Roitt et al., "Immunology: Fourth Edition", Mosby (1996), London, England, pp. 1.6-1.7.

Kimball, "Introduction to Immunology: Third Edition", Macmillan Publishing Company (1990), New York, p. 507.

Kaiser, "First Pass at Cancer Genome Reveals Complex Landscape", Science (2006), vol. 313, p. 1370.

Gura, "Systems for Identifying New Drugs are Often Faulty", Science (1997), vol. 278, pp. 1041-1042.

Tannock et al., "The Basic Science of Oncology: Second Edition", McGraw-Hill, Inc. (1992), Chapter 14.

* cited by examiner

FIGURE 1

|  |  | Secreting ELISA | | Cytotoxicity | | | Binding | | |
|---|---|---|---|---|---|---|---|---|---|
|  |  | Fold | | OCC-1 | OVCAR-3 | CCD-27sk | OCC-1 | OVCAR-3 | CCD7-27sk |
|  |  | IgG | IgM | Average | Average | Average | Fold | Fold | Fold |
|  | AR51A994.1 | 29.0 | 0.8 | 14 | 10 | -4 | 1.1 | 1.9 | 4.4 |
| Positive Controls | NaN$_3$ |  |  | 86 |  | -12 |  |  |  |
|  | CHX |  |  | 95 | 45 | 46 |  |  |  |

FIGURE 2A

|  |  | Pancreatic | Ovarian | | Normals | |
|---|---|---|---|---|---|---|
|  | Cell Line | BxPC-3 | OCC-1 | OVCAR-3 | CCD-27sk | Hs888.Lu |
|  | AR51A994.1 | 75 | 0 | 150 | 0 | 0 |
| Negative Controls | 1B7.11 | 0 | 0 | 0 | 0 | 0 |
|  | IgG Buffer | 0 | 0 | 0 | 0 | 0 |
| Positive Controls | anti-EGFR | 80 | 0 | 150 | 150 | 0 |
|  | CHX | 150 | 150 | 150 | 150 | 150 |

FIGURE 2B

|  |  | Lung | Pancreatic | | Ovarian | | | | | |
|---|---|---|---|---|---|---|---|---|---|---|
|  | Cell Line | A549 | AsPC-1 | PL45 | C-13 | ES-2 | Hey | OV2008 | OVCA-429 | OVCAR-3 |
|  | AR51A994.1 | 55 | 0 | 0 | 0 | 100 | 0 | 80 | 150 | 100 |
| Negative Controls | 1B7.11 | 0 | 0 | 0 | 0 | 0 | 0 | 0 | 0 | 0 |
|  | IgG Buffer | 0 | 0 | 0 | 100 | 0 | 0 | 0 | 0 | 0 |
| Positive Controls | anti-EGFR | 125 | 0 | 150 | 75 | 0 | 0 | 100 | 100 | 0 |
|  | CHX | 150 | 150 | 150 | 125 | 150 | 150 | 150 | 150 | 150 |

FIGURE 3A

|   | Cell Line | Pancreatic | Ovarian | | Normals | |
|---|---|---|---|---|---|---|
|   |   | BxPC-3 | OCC-1 | OVCAR-3 | CCD-27sk | Hs888.Lu |
|   | AR51A994.1 | 8.6 | 16.0 | 14.8 | 5.1 | 24.6 |
| Positive Control | anti-EGFR | 28.4 | 30.5 | 14.8 | 4.4 | 12.4 |

FIGURE 3B

|   | Cell Line | Lung | Pancreatic | | Ovarian | | | | | |
|---|---|---|---|---|---|---|---|---|---|---|
|   |   | A549 | AsPC-1 | PL45 | C-13 | ES-2 | Hey | OV2008 | OVCA-429 | OVCAR-3 |
|   | AR51A994.1 | 4.6 | 4.1 | 2.4 | 9.8 | 22.2 | 4.4 | 19.8 | 3.9 | 4.3 |
| Positive Control | anti-EGFR | 10.2 | 15.3 | 15.8 | 19.4 | 40 | 10.8 | 64.3 | 10.9 | 18.8 |

FIGURE 5

|  |  | Breast | Ovarian | Normals | | |
|---|---|---|---|---|---|---|
|  | Cell Line | MB-468 | OVCAR-3 | Bst549 | CCD-27sk | Hs888.Lu |
|  | 7BDI-60 | 130 | 0 | 0 | 0 | 0 |
|  | 7BDI-58 | 0 | 95 | 0 | 0 | 0 |
| Negative Controls | 107.3 | 0 | 0 | 0 | 0 | 0 |
| | IgG Buffer | 55 | 0 | 0 | 0 | 0 |
| Positive Controls | anti-Her2 | 0 | 125 | 0 | 0 | 0 |
| | CHX | 150 | 150 | 150 | 150 | 150 |

FIGURE 6

|  |  | Breast | Ovarian | Normals | | |
|---|---|---|---|---|---|---|
|  | Cell Line | MB-468 | OVCAR-3 | Bst549 | CCD-27sk | Hs888.Lu |
|  | 7BDI-60 | 5.1 | 5.7 | 3.7 | 8.1 | 9.1 |
|  | 7BDI-58 | 3.8 | 13.8 | 10.8 | 22.5 | 18.3 |
| Positive Control | anti-Her2 | 0.8 | 9.2 | 2.0 | 3.8 | 3.5 |

FIGURE 14

| | 7BD-33-11A | | | | | | | |
|---|---|---|---|---|---|---|---|---|
| IHC score | - | +/- | + | ++ | +++ | Total | Total positive | % positive |
| Tumor | 5 | 8 | 9 | 7 | 3 | 32 | 27 | 84% |
| Histological types | | | | | | | | |
| Ductal adenocarcinoma | 4 | 8 | 9 | 7 | 2 | 30 | 26 | 87% |
| Endocrine Carcinoma | 1 | 0 | 0 | 0 | 1 | 2 | 1 | 50% |
| Normal pancraes | 0 | 0 | 0 | 1 | 3 | 4 | 4 | 100% |
| Histological grade/Adenocarcinoma | Total No. 30 tumors of ductal adenocarcinoma | | | | | | | |
| G1 | 0 | 0 | 1 | 0 | 0 | 1 | 1 | 100% |
| G1-G2 | 1 | 1 | 1 | 0 | 0 | 3 | 2 | 67% |
| G2 | 3 | 2 | 3 | 3 | 1 | 12 | 9 | 75% |
| G2-G3 | 0 | 0 | 2 | 0 | 0 | 2 | 2 | 100% |
| G3 | 0 | 1 | 1 | 3 | 1 | 6 | 6 | 100% |
| G4 | 0 | 1 | 0 | 0 | 0 | 1 | 1 | 100% |
| Unknown | 0 | 3 | 1 | 1 | 0 | 5 | 5 | 100% |
| TNM Satge/Adenocarcinoma | Total No. 30 tumors of ductal adenocarcinoma | | | | | | | |
| Satge I | 0 | 0 | 1 | 0 | 0 | 1 | 1 | 100% |
| Satge II | 3 | 4 | 4 | 5 | 1 | 17 | 14 | 82% |
| Satge III | 0 | 0 | 1 | 0 | 0 | 1 | 1 | 100% |
| Satge IV | 1 | 4 | 3 | 2 | 1 | 11 | 10 | 91% |

FIGURE 15
A
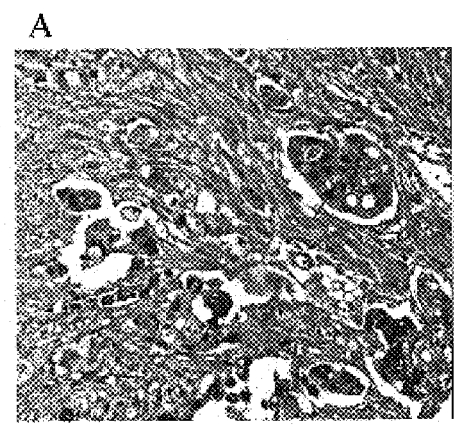
B
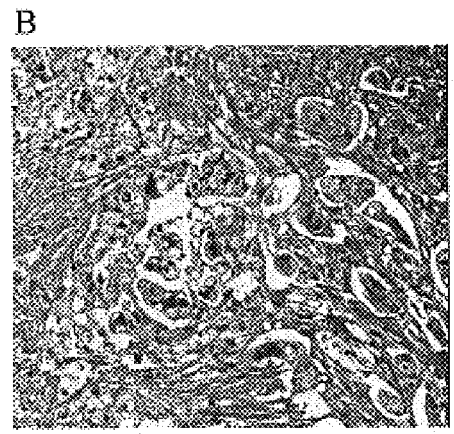
C
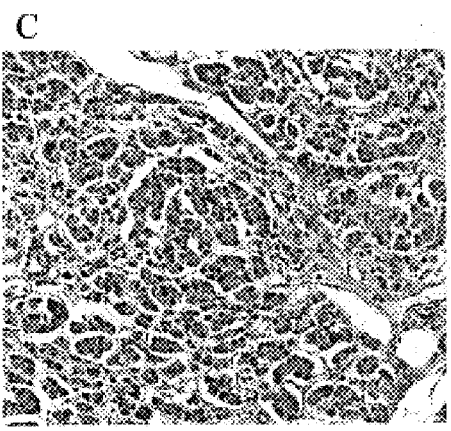
D
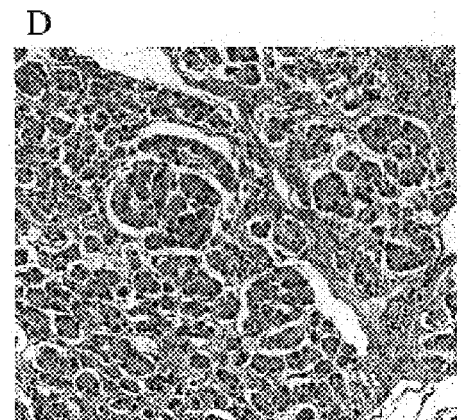

FIGURE 16
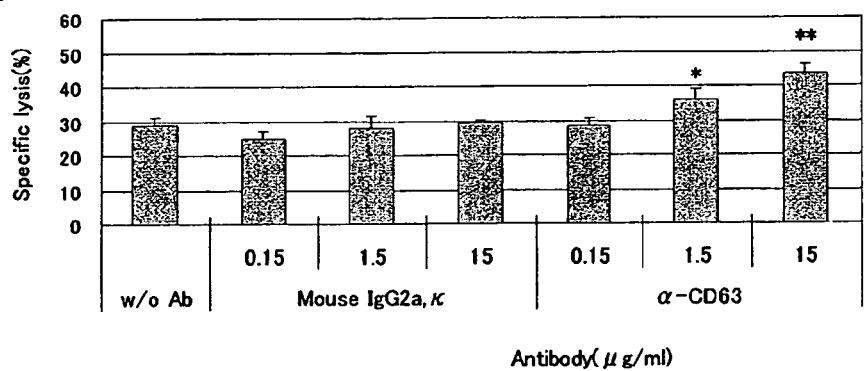
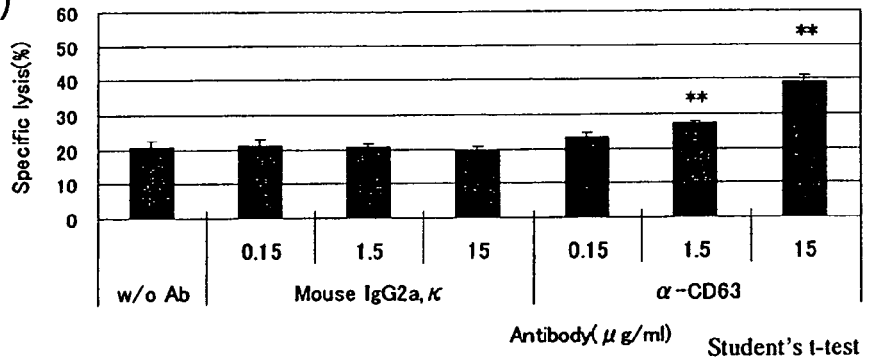
Student's t-test
*≤ 0.05, **≤ 0.01

FIGURE 17

| Treatment | Mean # of Macrophages | P Value | P Value (All Tumors) | Mean Tumor volume (mm3) | P Value |
|---|---|---|---|---|---|
| 3 doses buffer | 81.8 | 0.36 | 0.037 | 43.46 | 0.24 |
| 3 doses buffer | | | | | |
| 3 doses buffer | | | | | |
| 3 doses 7BD-33-11A | 102.5 | | | 60.95 | |
| 3 doses 7BD-33-11A | | | | | |
| 3 doses 7BD-33-11A | | | | | |
| 6 doses buffer | 112 | 0.047 | | 62.14 | 0.027 |
| 6 doses buffer | | | | | |
| 6 doses buffer | | | | | |
| 6 doses 7BD-33-11A | 175.7 | | | 3.28 | |
| 6 doses 7BD-33-11A | | | | | |
| 6 doses 7BD-33-11A | | | | | |
| 10 doses buffer | 116.7 | 0.4 | | 251.17 | 0.12 |
| 10 doses buffer | | | | | |
| 10 doses buffer | | | | | |
| 10 doses 7BD-33-11A | 179.5 | | | 97.79 | |
| 10 doses 7BD-33-11A | | | | | |
| 10 doses 7BD-33-11A | | | | | |

FIGURE 18

| residue no. | amino acid | residue no. | amino acid | residue no. | amino acid | residue no. | amino acid |
|---|---|---|---|---|---|---|---|
| 1 | N, E | 6 | Q | 11 | L | 16 | A, G |
| 2 | V, I | 7 | S | 12 | V, A | 17 | S, E |
| 3 | M, Q | 8 | P, G | 13 | K, V | 18 | V, K |
| 4 | M, L | 9 | S, P | 14 | P, S | 19 | K, V |
| 5 | T, Q | 10 | S, G | 15 | G, A | 20 | M, T |

FIGURE 19

```
                        30                              60
ATGGAATCACAGACTCAGGTCTTCCTCTCCCTGCTGCTCTGGGTATCTGGTACCTGTGGG
 M   E   S   Q   T   Q   V   F   L   S   L   L   W   V   S   G   T   C   G 90                             120
AACATTATGATGACACAGTCGCCATCATCTCTGGCTGTGTCTGCAGGAGAAAAGGTCACT
 N   I   M   M   T   Q   S   P   S   S   L   A   V   S   A   G   E   K   V   T 150                             180
ATGAGCTGTAAGTCCAGTCAAAGTGTTTTATACAGTTCAAATCAGAAAAACTACTTGGCC
 M   S   C   K   S   S   Q   S   V   L   Y   S   S   N   Q   K   N   Y   L   A 210                             240
TGGTACCAGCAGAAACCAGGGCAGTCTCCTAAACTGCTGATCTACTGGGCATCCACTAGG
 W   Y   Q   Q   K   P   G   Q   S   P   K   L   L   I   Y   W   A   S   T   R 270                             300
GAATCTGGTGTCCCTGATCGCTTCACAGGCAGTGGATCTGGGACAGATTTTACTCTTACC
 E   S   G   V   P   D   R   F   T   G   S   G   S   G   T   D   F   T   L   T 330                             360
ATCAGCAGTGTACAAGCTGAAGACCTGGCAGTTTATTACTGTCATCAATATTTCTCCTCG
 I   S   S   V   Q   A   E   D   L   A   V   Y   Y   C   H   Q   Y   F   S   S 390  396
TACACGTTCGGAGGGGGGACCAAGCTGGAAATAAAA
 Y   T   F   G   G   G   T   K   L   E   I   K
```

FIGURE 20

```
                          30                                60
ATGGAATGGAGTTGGATATTTCTCTTTCTCCTGTCAGGAACTGCAGGTGTCCACTCTGAG
 M   E   W   S   W   I   F   L   F   L   L   S   G   T   A   G   V   H   S   E 90                               120
GTCCAGCTGCAGCAGTCTGGACCTGGGCTGGTAAAGCCTGGGGCTTCAGTGAAGATGTCC
 V   Q   L   Q   Q   S   G   P   G   L   V   K   P   G   A   S   V   K   M   S 150                               180
TGCAAGGCTTCTGGATACACATTCACTAGTTATGTTATGCACTGGGTGAAGCAGATGCCT
 C   K   A   S   G   Y   T   F   T   S   Y   V   M   H   W   V   K   Q   M   P 210                               240
GGGCAGGGCCTTGAGTGGATTGGATATATTACTCCTTATAATGATGGTACTAAATACAAT
 G   Q   G   L   E   W   I   G   Y   I   T   P   Y   N   D   G   T   K   Y   N 270                               300
GAGAAGTTCAAAGGCAAGGCCACACTGACTTCAGACAAATCCTCCAGCACAGCCTACATG
 E   K   F   K   G   K   A   T   L   T   S   D   K   S   S   S   T   A   Y   M 330                               360
GACCTCAGCAGCCTGACCTCTGAGGACTCTGCGGTCTATTACTGTGTCTACGGTAGTAGA
 D   L   S   S   L   T   S   E   D   S   A   V   Y   Y   C   V   Y   G   S   R 390                         414
TACGACTGGTACTTCGATGTCTGGGGCGCAGGGACCACGGTCACCGTCTCCTCA
 Y   D   W   Y   F   D   V   W   G   A   G   T   T   V   T   V   S   S
```

FIGURE 21

```
                                                                    30
Mu33-11A    N I M M T Q S P S S L A V S A G E K V T M S C K S S Q S V L
Hu33-11A    D I V M T Q S P D S L A V S L G E R A T I S C K S S Q S V L
1LVE        D I V M T Q S P D S L A V S L G E R A T I N C - - - - - - -

60
Mu33-11A    Y S S N Q K N Y L A W Y Q Q K P G Q S P K L L I Y W A S T R
Hu33-11A    Y S S N Q K N Y L A W Y Q Q K P G Q P P K L L I Y W A S T R
1LVE        - - - - - - - - - - W Y Q Q K P G Q P P K L L I Y - - - - -

90
Mu33-11A    E S G V P D R F T G S G S G T D F T L T I S S V Q A E D L A
Hu33-11A    E S G V P D R F S G S G S G T D F T L T I S S L Q A E D V A
1LVE        - - G V P D R F S G S G S G T D F T L T I S S L Q A E D V A

112
Mu33-11A    V Y Y C H Q Y F S S Y T F G G G T K L E I K
Hu33-11A    V Y Y C H Q Y F S S Y T F G Q G T K L E I K
1LVE/JK2    V Y Y C - - - - - - - - F G Q G T K L E I K
```

FIGURE 22

```
                                                              30
Mu33-11A       E V Q L Q Q S G P G L V K P G A S V K M S C K A S G Y T F T
Hu33-11A       E V Q L V Q S G A E V K K P G A T V K I S C K V S G Y T F T
Hu33-11A(V11L) E V Q L V Q S G A E L K K P G A T V K I S C K V S G Y T F T
AAR32409       E V Q L V Q S G A E V K K P G A T V K I S C K V S G Y T F I

60
Mu33-11A       S Y V M H W V K Q M P G Q G L E W I G Y I T P Y N D G T K Y
Hu33-11A       S Y V M H W V R Q A P G K G L E W I G Y I T P Y N D G T K Y
Hu33-11A(V11L) S Y V M H W V R Q A P G K G L E W I G Y I T P Y N D G T K Y
AAR32409       - - - - - W V Q Q V P G K G L E W M G - - - - - - - - - - -

90
Mu33-11A       N E K F K G K A T L T S D K S S S T A Y M D L S S L T S E D
Hu33-11A       N E K F K G K A T L T S D K S T D T A Y M E L S S L R S E D
Hu33-11A(V11L) N E K F K G K A T L T S D K S T D T A Y M E L S S L R S E D
AAR32409       - - - - - - R V T I T A D T S T D T A Y M E L G S L R S E D

119
Mu33-11A       S A V Y Y C V Y G S R Y D W Y F D V W G A G T T V T V S S
Hu33-11A       T A V Y Y C V Y G S R Y D W Y F D V W G Q G T T V T V S S
Hu33-11A(V11L) T A V Y Y C V Y G S R Y D W Y F D V W G Q G T T V T V S S
AAR32409/JH6   T A V Y Y C A T - - - - - - - - - - - W G Q G T T V T V S S
```

FIGURE 23

```
                           30                              60
ACGCGTCCACCATGGATTTTCAAGTGCAGATTTTCAGCTTCCTGCTAATCAGTGCCTCAG
            M  D  F  Q  V  Q  I  F  S  F  L  L  I  S  A  S 90                             120
TCATAATATCCAGAGGAGACATTGTGATGACACAGTCGCCAGACTCTCTGGCTGTGTCTC
 V  I  I  S  R  G  D  I  V  M  T  Q  S  P  D  S  L  A  V  S 150                             180
TAGGAGAAAGGGCCACTATCAGCTGCAAGTCCAGTCAAAGTGTTTTATACAGTTCAAATC
 L  G  E  R  A  T  I  S  C  K  S  S  Q  S  V  L  Y  S  S  N 210                             240
AGAAAAACTACTTGGCCTGGTACCAGCAGAAACCAGGGCAGCCTCCTAAACTGCTGATCT
 Q  K  N  Y  L  A  W  Y  Q  Q  K  P  G  Q  P  P  K  L  L  I 270                             300
ACTGGGCATCCACTAGGGAATCTGGTGTCCCTGATCGCTTCTCAGGCAGTGGATCTGGGA
 Y  W  A  S  T  R  E  S  G  V  P  D  R  F  S  G  S  G  S 330                             360
CAGATTTTACTCTTACCATCAGCAGTCTACAAGCTGAAGACGTGGCAGTTTATTACTGTC
 T  D  F  T  L  T  I  S  S  L  Q  A  E  D  V  A  V  Y  Y  C 390                             420
ATCAATATTTCTCCTCGTACACGTTCGGACAGGGGACCAAGCTGGAAATAAAACGTAAGT
 H  Q  Y  F  S  S  Y  T  F  G  Q  G  T  K  L  E  I  K

433
ACTTTTTTCTAGA
```

FIGURE 24

```
                          30                              60
ACGCGTCCACCATGGACTCCAGGCTCAATTTAGTTTTCCTTGTCCTTATTTTAAAAGGTG
              M   D   S   R   L   N   L   V   F   L   V   L   I   L   K   G 90                             120
TCCAGTGTGAGGTCCAGCTGGTGCAGTCTGGAGCTGAGCTGAAAAAGCCTGGGGCTACAG
V   Q   C   E   V   Q   L   V   Q   S   G   A   E   L   K   K   P   G   A   T 150                             180
TGAAGATCTCCTGCAAGGTCTCTGGATACACATTCACTAGTTATGTTATGCACTGGGTTA
V   K   I   S   C   K   V   S   G   Y   T   F   T   S   Y   V   M   H   W   V 210                             240
GGCAGGCGCCTGGGAAGGGCCTTGAGTGGATTGGATATATTACTCCTTATAATGATGGTA
R   Q   A   P   G   K   G   L   E   W   I   G   Y   I   T   P   Y   N   D   G 270                             300
CTAAATACAATGAGAAGTTCAAAGGCAAGGCCACACTGACTTCAGACAAATCCACCGACA
  T   K   Y   N   E   K   F   G   K   A   T   L   T   S   D   K   S   T   D 330                             360
CAGCCTACATGGAACTCAGCAGCCTGCGCTCTGAGGACACTGCGGTCTATTACTGTGTCT
  T   A   Y   M   E   L   S   S   L   R   S   E   D   T   A   V   Y   Y   C   V 390                             420
ACGGTAGTAGATACGACTGGTACTTCGATGTCTGGGGCCAAGGGACCACCGTCACCGTCT
  Y   G   S   R   Y   D   W   Y   F   D   V   W   G   Q   G   T   T   V   T   V

446
CCTCAGGTAAGAATGGCCACTCTAGA
S   S
```

FIGURE 25

| Primer | Sequence (5'→3') |
|---|---|
| L1 | TATAACGCGTCCACCATGGATTTTCAAGTGCAGATTTTCA |
| L2 | GGCACTGATTAGCAGGAAGCTGAAAATCTGCACTTGAAAA |
| L3 | GCTTCCTGCTAATCAGTGCCTCAGTCATAATATCCAGAGG |
| L4 | ACTGTGTCATCACAATGTCTCCTCTGGATATTATGACTGA |
| L5 | AGACATTGTGATGACACAGTCGCCAGACTCTCTGGCTGTG |
| L6 | GTGGCCCTTTCTCCTAGAGACACAGCCAGAGAGTCTGGCG |
| L7 | TCTCTAGGAGAAAGGGCCACTATCAGCTGCAAGTCCAGTC |
| L8 | TGAACTGTATAAAACACTTTGACTGGACTTGCAGCTGATA |
| L9 | AAAGTGTTTTATACAGTTCAAATCAGAAAAACTACTTGGC |
| L10 | CTGGTTTCTGCTGGTACCAGGCCAAGTAGTTTTTCTGATT |
| L11 | CTGGTACCAGCAGAAACCAGGGCAGCCTCCTAAACTGCTG |
| L12 | CTAGTGGATGCCCAGTAGATCAGCAGTTTAGGAGGCTGCC |
| L13 | ATCTACTGGGCATCCACTAGGGAATCTGGTGTCCCTGATC |
| L14 | AGATCCACTGCCTGAGAAGCGATCAGGGACACCAGATTCC |
| L15 | GCTTCTCAGGCAGTGGATCTGGGACAGATTTTACTCTTAC |
| L16 | CAGCTTGTAGACTGCTGATGGTAAGAGTAAAATCTGTCCC |
| L17 | CATCAGCAGTCTACAAGCTGAAGACGTGGCAGTTTATTAC |
| L18 | GAGGAGAAATATTGATGACAGTAATAAACTGCCACGTCTT |
| L19 | TGTCATCAATATTTCTCCTCGTACACGTTCGGACAGGGGA |
| L20 | TCTAGAAAAAAGTACTTACGTTTTATTTCCAGCTTGGTCCC CTGTCCGAACGTGTAC |

FIGURE 26

| Primer | Sequence (5'→3') |
|---|---|
| H1 | TATAACGCGTCCACCATGGACTCCAGGCTCAATTTAGTTT |
| H2 | TTTTAAAATAAGGACAAGGAAAACTAAATTGAGCCTGGAG |
| H3 | TCCTTGTCCTTATTTTAAAAGGTGTCCAGTGTGAGGTCCA |
| H4 | CAGCTCCAGACTGCACCAGCTGGACCTCACACTGGACACC |
| H5 | GCTGGTGCAGTCTGGAGCTGAGGTGAAAAAGCCTGGGGCT |
| H6 | TTGCAGGAGATCTTCACTGTAGCCCCAGGCTTTTTCACCT |
| H7 | ACAGTGAAGATCTCCTGCAAGGTCTCTGGATACACATTCA |
| H8 | CCAGTGCATAACATAACTAGTGAATGTGTATCCAGAGACC |
| H9 | CTAGTTATGTTATGCACTGGGTTAGGCAGGCGCCTGGGAA |
| H10 | ATCCAATCCACTCAAGGCCCTTCCCAGGCGCCTGCCTAAC |
| H11 | GGGCCTTGAGTGGATTGGATATATTACTCCTTATAATGAT |
| H12 | TTCTCATTGTATTTAGTACCATCATTATAAGGAGTAATAT |
| H13 | GGTACTAAATACAATGAGAAGTTCAAAGGCAAGGCCACAC |
| H14 | GGTGGATTTGTCTGAAGTCAGTGTGGCCTTGCCTTTGAAC |
| H15 | TGACTTCAGACAAATCCACCGACACAGCCTACATGGAACT |
| H16 | CCTCAGAGCGCAGGCTGCTGAGTTCCATGTAGGCTGTGTC |
| H17 | CAGCAGCCTGCGCTCTGAGGACACTGCGGTCTATTACTGT |
| H18 | TCGTATCTACTACCGTAGACACAGTAATAGACCGCAGTGT |
| H19 | GTCTACGGTAGTAGATACGACTGGTACTTCGATGTCTGGG |
| H20 | GGTGACGGTGGTCCCTTGGCCCCAGACATCGAAGTACCAG |
| H21 | GCCAAGGGACCACCGTCACCGTCTCCTCAGGTAAGAATGG |
| H22 | TATATCTAGAGTGGCCATTCTTACCTGAGGAGAC |

FIGURE 28

| Antibody | IC$_{50}$ (µg/ml) | | |
|---|---|---|---|
| | n | Average | Std. Dev. |
| Mu33-11A | 11 | 7.02 | 2.35 |
| Hu33-11A.IgG1 | 9 | 25.3 | 9.1 |
| Hu33-11A.IgG2M3 | 2 | 62.3 | 15.1 |
| Hu33-11A.IgG1 (V24A) | 3 | 25.8 | 9.0 |
| Hu33-11A.IgG1 (R38K) | 3 | 36.0 | 18.2 |
| Hu33-11A.IgG1 (V24A,R38K) | 3 | 34.2 | 3.3 |
| Hu33-11A.IgG1 (V11L) | 3 | 17.1 | 0.7 |
| Hu33-11A.IgG1 (I20M) | 3 | 38.4 | 3.4 |
| Hu33-11A.IgG1 (Q111A) | 3 | 32.3 | 2.3 |

* Single amino acid substitution

FIGURE 31

```
  1 ATGGATTTTCAAGTGCAGATTTTCAGCTTCCTGCTAATCAGTGCCTCAGTCATAATATCC
    M  D  F  Q  V  Q  I  F  S  F  L  L  I  S  A  S  V  I  I  S
 61 AGAGGAGACATTGTGATGACACAGTCGCCAGACTCTCTGGCTGTGTCTCTAGGAGAAAGG
    R  G  D  I  V  M  T  Q  S  P  D  S  L  A  V  S  L  G  E  R
121 GCCACTATCAGCTGCAAGTCCAGTCAAAGTGTTTTATACAGTTCAAATCAGAAAAACTAC
    A  T  I  S  C  K  S  S  Q  S  V  L  Y  S  S  N  Q  K  N  Y
181 TTGGCCTGGTACCAGCAGAAACCAGGGCAGCCTCCTAAACTGCTGATCTACTGGGCATCC
    L  A  W  Y  Q  Q  K  P  G  Q  P  P  K  L  L  I  Y  W  A  S
241 ACTAGGGAATCTGGTGTCCCTGATCGCTTCTCAGGCAGTGGATCTGGGACAGATTTTACT
    T  R  E  S  G  V  P  D  R  F  S  G  S  G  S  G  T  D  F  T
301 CTTACCATCAGCAGTCTACAAGCTGAAGACGTGGCAGTTTATTACTGTCATCAATATTTC
    L  T  I  S  S  L  Q  A  E  D  V  A  V  Y  Y  C  H  Q  Y  F
361 TCCTCGTACACGTTCGGACAGGGGACCAAGCTGGAAATAAAACGTACTGTGGCTGCACCA
    S  S  Y  T  F  G  Q  G  T  K  L  E  I  K  R  T  V  A  A  P
421 TCTGTCTTCATCTTCCCGCCATCTGATGAGCAGTTGAAATCTGGAACTGCCTCTGTTGTG
    S  V  F  I  F  P  P  S  D  E  Q  L  K  S  G  T  A  S  V  V
481 TGCCTGCTGAATAACTTCTATCCCAGAGAGGCCAAAGTACAGTGGAAGGTGGATAACGCC
    C  L  L  N  N  F  Y  P  R  E  A  K  V  Q  W  K  V  D  N  A
541 CTCCAATCGGGTAACTCCCAGGAGAGTGTCACAGAGCAGGACAGCAAGGACAGCACCTAC
    L  Q  S  G  N  S  Q  E  S  V  T  E  Q  D  S  K  D  S  T  Y
601 AGCCTCAGCAGCACCCTGACGCTGAGCAAAGCAGACTACGAGAAACACAAAGTCTACGCC
    S  L  S  S  T  L  T  L  S  K  A  D  Y  E  K  H  K  V  Y  A
661 TGCGAAGTCACCCATCAGGGCCTGAGCTCGCCCGTCACAAAGAGCTTCAACAGGGGAGAG
    C  E  V  T  H  Q  G  L  S  S  P  V  T  K  S  F  N  R  G  E
721 TGTTAG
    C  *
```

FIGURE 32

```
   1 ATGGACTCCAGGCTCAATTTAGTTTTCCTTGTCCTTATTTTAAAAGGTGTCCAGTGTGAG
     M  D  S  R  L  N  L  V  F  L  V  L  I  L  K  G  V  Q  C  E
  61 GTCCAGCTGGTGCAGTCTGGAGCTGAGCTGAAAAAGCCTGGGGCTACAGTGAAGATCTCC
     V  Q  L  V  Q  S  G  A  E  L  K  K  P  G  A  T  V  K  I  S
 121 TGCAAGGTCTCTGGATACACATTCACTAGTTATGTTATGCACTGGGTTAGGCAGGCGCCT
     C  K  V  S  G  Y  T  F  T  S  Y  V  M  H  W  V  R  Q  A  P
 181 GGGAAGGGCCTTGAGTGGATTGGATATATTACTCCTTATAATGATGGTACTAAATACAAT
     G  K  G  L  E  W  I  G  Y  I  T  P  Y  N  D  G  T  K  Y  N
 241 GAGAAGTTCAAAGGCAAGGCCACACTGACTTCAGACAAATCCACCGACACAGCCTACATG
     E  K  F  K  G  K  A  T  L  T  S  D  K  S  T  D  T  A  Y  M
 301 GAACTCAGCAGCCTGCGCTCTGAGGACACTGCGGTCTATTACTGTGTCTACGGTAGTAGA
     E  L  S  S  L  R  S  E  D  T  A  V  Y  Y  C  V  Y  G  S  R
 361 TACGACTGGTACTTCGATGTCTGGGGCCAAGGGACCACCGTCACCGTCTCCTCAGCCTCC
     Y  D  W  Y  F  D  V  W  G  Q  G  T  T  V  T  V  S  S  A  S
 421 ACCAAGGGCCCATCGGTCTTCCCCCTGGCACCCTCCTCCAAGAGCACCTCTGGGGGCACA
     T  K  G  P  S  V  F  P  L  A  P  S  S  K  S  T  S  G  G  T
 481 GCGGCCCTGGGCTGCCTGGTCAAGGACTACTTCCCCGAACCGGTGACGGTGTCGTGGAAC
     A  A  L  G  C  L  V  K  D  Y  F  P  E  P  V  T  V  S  W  N
 541 TCAGGCGCCCTGACCAGCGGCGTGCACACCTTCCCGGCTGTCCTACAGTCCTCAGGACTC
     S  G  A  L  T  S  G  V  H  T  F  P  A  V  L  Q  S  S  G  L
 601 TACTCCCTCAGCAGCGTGGTGACCGTGCCCTCCAGCAGCTTGGGCACCCAGACCTACATC
     Y  S  L  S  S  V  V  T  V  P  S  S  S  L  G  T  Q  T  Y  I
 661 TGCAACGTGAATCACAAGCCCAGCAACACCAAGGTGGACAAGAAAGTTGAGCCCAAATCT
     C  N  V  N  H  K  P  S  N  T  K  V  D  K  K  V  E  P  K  S
 721 TGTGACAAAACTCACACATGCCCACCGTGCCCAGCACCTGAACTCCTGGGGGGACCGTCA
     C  D  K  T  H  T  C  P  P  C  P  A  P  E  L  L  G  G  P  S
 781 GTCTTCCTCTTCCCCCCAAAACCCAAGGACACCCTCATGATCTCCCGGACCCCTGAGGTC
     V  F  L  F  P  P  K  P  K  D  T  L  M  I  S  R  T  P  E  V
 841 ACATGCGTGGTGGTGGACGTGAGCCACGAAGACCCTGAGGTCAAGTTCAACTGGTACGTG
     T  C  V  V  V  D  V  S  H  E  D  P  E  V  K  F  N  W  Y  V
 901 GACGGCGTGGAGGTGCATAATGCCAAGACAAAGCCGCGGGAGGAGCAGTACAACAGCACG
     D  G  V  E  V  H  N  A  K  T  K  P  R  E  E  Q  Y  N  S  T
 961 TACCGTGTGGTCAGCGTCCTCACCGTCCTGCACCAGGACTGGCTGAATGGCAAGGAGTAC
     Y  R  V  V  S  V  L  T  V  L  H  Q  D  W  L  N  G  K  E  Y
1021 AAGTGCAAGGTCTCCAACAAAGCCCTCCCAGCCCCCATCGAGAAAACCATCTCCAAAGCC
     K  C  K  V  S  N  K  A  L  P  A  P  I  E  K  T  I  S  K  A
1081 AAAGGGCAGCCCCGAGAACCACAGGTGTACACCCTGCCCCCATCCCGGGATGAGCTGACC
     K  G  Q  P  R  E  P  Q  V  Y  T  L  P  P  S  R  D  E  L  T
1141 AAGAACCAGGTCAGCCTGACCTGCCTGGTCAAAGGCTTCTATCCCAGCGACATCGCCGTG
     K  N  Q  V  S  L  T  C  L  V  K  G  F  Y  P  S  D  I  A  V
1201 GAGTGGGAGAGCAATGGGCAGCCGGAGAACAACTACAAGACCACGCCTCCCGTGCTGGAC
     E  W  E  S  N  G  Q  P  E  N  N  Y  K  T  T  P  P  V  L  D
1261 TCCGACGGCTCCTTCTTCCTCTACAGCAAGCTCACCGTGGACAAGAGCAGGTGGCAGCAg
     S  D  G  S  F  F  L  Y  S  K  L  T  V  D  K  S  R  W  Q  Q
1321 GGGAACGTCTTCTCATGCTCCGTGATGCATGAGGCTCTGCACAACCACTACACGCAGAAG
     G  N  V  F  S  C  S  V  M  H  E  A  L  H  N  H  Y  T  Q  K
1381 AGCCTCTCCCTGTCTCCGGGTAAATGA
     S  L  S  L  S  P  G  K  •
```

FIGURE 33

```
   1 ATGGACTCCAGGCTCAATTTAGTTTTCCTTGTCCTTATTTTAAAAGGTGTCCAGTGTGAG
     M  D  S  R  L  N  L  V  F  L  V  L  I  L  K  G  V  Q  C  E
  61 GTCCAGCTGGTGCAGTCTGGAGCTGAGCTGAAAAAGCCTGGGGCTACAGTGAAGATCTCC
     V  Q  L  V  Q  S  G  A  E  L  K  K  P  G  A  T  V  K  I  S
 121 TGCAAGGTCTCTGGATACACATTCACTAGTTATGTTATGCACTGGGTTAGGCAGGCGCCT
     C  K  V  S  G  Y  T  F  T  S  Y  V  M  H  W  V  R  Q  A  P
 181 GGGAAGGGCCTTGAGTGGATTGGATATATTACTCCTTATAATGATGGTACTAAATACAAT
     G  K  G  L  E  W  I  G  Y  I  T  P  Y  N  D  G  T  K  Y  N
 241 GAGAAGTTCAAAGGCAAGGCCACACTGACTTCAGACAAATCCACCGACACAGCCTACATG
     E  K  F  K  G  K  A  T  L  T  S  D  K  S  T  D  T  A  Y  M
 301 GAACTCAGCAGCCTGCGCTCTGAGGACACTGCGGTCTATTACTGTGTCTACGGTAGTAGA
     E  L  S  S  L  R  S  E  D  T  A  V  Y  Y  C  V  Y  G  S  R
 361 TACGACTGGTACTTCGATGTCTGGGGCCAAGGGACCACCGTCACCGTCTCCTCAGCCTCC
     Y  D  W  Y  F  D  V  W  G  Q  G  T  T  V  T  V  S  S  A  S
 421 ACCAAGGGCCCATCGGTCTTCCCCCTGGCGCCCTGCTCCAGGAGCACCTCCGAGAGCACA
     T  K  G  P  S  V  F  P  L  A  P  C  S  R  S  T  S  E  S  T
 481 GCGGCCCTGGGCTGCCTGGTCAAGGACTACTTCCCCGAACCGGTGACGGTGTCGTGGAAC
     A  A  L  G  C  L  V  K  D  Y  F  P  E  P  V  T  V  S  W  N
 541 TCAGGCGCTCTGACCAGCGGCGTGCACACCTTCCCAGCTGTCCTACAGTCCTCAGGACTC
     S  G  A  L  T  S  G  V  H  T  F  P  A  V  L  Q  S  S  G  L
 601 TACTCCCTCAGCAGCGTGGTGACCGTGCCCTCCAGCAACTTCGGCACCCAGACCTACACC
     Y  S  L  S  S  V  V  T  V  P  S  S  N  F  G  T  Q  T  Y  T
 661 TGCAACGTAGATCACAAGCCCAGCAACACCAAGGTGGACAAGACAGTTGAGCGCAAATGT
     C  N  V  D  H  K  P  S  N  T  K  V  D  K  T  V  E  R  K  C
 721 TGTGTCGAGTGCCCACCGTGCCCAGCACCACCTGCGGCAGCACCGTCAGTCTTCCTCTTC
     C  V  E  C  P  P  C  P  A  P  P  A  A  A  P  S  V  F  L  F
 781 CCCCCAAAACCCAAGGACACCCTCATGATCTCCCGGACCCCTGAGGTCACGTGCGTGGTG
     P  P  K  P  K  D  T  L  M  I  S  R  T  P  E  V  T  C  V  V
 841 GTGGACGTGAGCCACGAAGACCCCGAGGTCCAGTTCAACTGGTACGTGGACGGCGTGGAG
     V  D  V  S  H  E  D  P  E  V  Q  F  N  W  Y  V  D  G  V  E
 901 GTGCATAATGCCAAGACAAAGCCACGGGAGGAGCAGTTCAACAGCACGTTCCGTGTGGTC
     V  H  N  A  K  T  K  P  R  E  E  Q  F  N  S  T  F  R  V  V
 961 AGCGTCCTCACCGTTGTGCACCAGGACTGGCTGAACGGCAAGGAGTACAAGTGCAAGGTC
     S  V  L  T  V  V  H  Q  D  W  L  N  G  K  E  Y  K  C  K  V
1021 TCCAACAAAGGCCTCCCAGCCCCCATCGAGAAAACCATCTCCAAAACCAAAGGGCAGCCC
     S  N  K  G  L  P  A  P  I  E  K  T  I  S  K  T  K  G  Q  P
1081 CGAGAACCACAGGTGTACACCCTGCCCCCATCCCGGGAGGAGATGACCAAGAACCAGGTC
     R  E  P  Q  V  Y  T  L  P  P  S  R  E  E  M  T  K  N  Q  V
1141 AGCCTGACCTGCCTGGTCAAAGGCTTCTACCCCAGCGACATCGCCGTGGAGTGGGAGAGC
     S  L  T  C  L  V  K  G  F  Y  P  S  D  I  A  V  E  W  E  S
1201 AATGGGCAGCCGGAGAACAACTACAAGACCACACCTCCCATGCTGGACTCCGACGGCTCC
     N  G  Q  P  E  N  N  Y  K  T  T  P  P  M  L  D  S  D  G  S
1261 TTCTTCCTCTACAGCAAGCTCACCGTGGACAAGAGCAGGTGGCAGCAGGGGAACGTCTTC
     F  F  L  Y  S  K  L  T  V  D  K  S  R  W  Q  Q  G  N  V  F
1321 TCATGCTCCGTGATGCATGAGGCTCTGCACAACCACTACACGCAGAAGAGCCTCTCCCTG
     S  C  S  V  M  H  E  A  L  H  N  H  Y  T  Q  K  S  L  S  L
1381 TCTCCGGGTAAATGA
     S  P  G  K  •
```

FIGURE 36

| Antibody | IC$_{50}$ (μg/ml) | | | | |
|---|---|---|---|---|---|
| | Exp. A | Exp. B | Exp. C | Average | Std. Dev. |
| Mu33-11A | 6.3 | 6.9 | 7.3 | 6.83 | 0.5 |
| Hu33-11A.IgG1 (V11L) | 14.4 | 12.5 | 11.3 | 12.7 | 1.6 |
| Hu33-11A.IgG2M3 (V11L) | 37.5 | 38.9 | 40 | 38.8 | 1.2 |

- 7BD-33-11A
- ▲ (hu)AR7BD-33-11A-IgG1(V11L)
- ● (hu)AR7BD-33-11A-IgG2M3(V11L)
- ◆ Murine IgG1 Isotype Control
- ● Humanized IgG1 Isotype Control
- ☐ Humanized IgG2M3 Isotype Control
- △ No Competitor Antibody
- ▽ Cells Only (No Antibody)

FIGURE 40

| Antibody | KD(nM) | SEM* |
|---|---|---|
| 7BD-33-11A | 135.0 | 30.4 |
| H460-22-1 | 41.7 | 8.3 |
| 1A245.6 | 9.8 | 2.9 |
| (hu)AR7BD-33-11A-IgG1** | 66.7 | 8.4 |
| (hu)AR7BD-33-11A-IgG2M3** | 50.0 | 0 |

*Data is the average and standard error of the mean (SEM) of at least three independent experiments.
** n=2

CYTOTOXICITY MEDIATION OF CELLS EVIDENCING SURFACE EXPRESSION OF CD63

REFERENCE TO RELATED APPLICATIONS

This application is a continuation-in-part of U.S. patent application Ser. No. 11/321,624, filed Dec. 29, 2005, which relies upon U.S. Provisional Application No. 60/642,057, filed Jan. 3, 2005, and is a continuation-in-part to U.S. patent application Ser. No. 10/810,751, filed Mar. 26, 2004, which is a continuation-in-part to U.S. patent application Ser. No. 10/603,006, filed Jun. 23, 2003, which is a continuation-in-part to U.S. patent application Ser. No. 10/348,231, filed Jan. 21, 2003, now U.S. Pat. No. 7,009,040 (including U.S. divisional application Ser. No. 10/891,866, filed Jul. 15, 2004), and is a continuation-in-part to U.S. patent application Ser. No. 09/727,361, filed Nov. 29, 2000, now U.S. Pat. No. 6,657,048 issued Dec. 2, 2003 (including U.S. divisional application Ser. No. 10/713,642, filed Nov. 13, 2003), the contents of each of which are herein incorporated by reference.

FIELD OF THE INVENTION

This invention relates to the diagnosis and treatment of cancerous diseases, particularly to the mediation of cytotoxicity of tumor cells; and most particularly to the use of cancerous disease modifying antibodies (CDMAB), optionally in combination with one or more chemotherapeutic agents, as a means for initiating the cytotoxic response. The invention further relates to binding assays, which utilize the CDMAB of the instant invention

BACKGROUND OF THE INVENTION

CD63 in Cancer: CD63 is a Type III membrane protein of the tetraspanin family whose 20 current members are characterized by the presence of four transmembrane segments. Several groups independently identified CD63, using antibodies raised to whole cell preparations of activated platelets, granulocytes, and melanoma cells. Cloning of the respective cDNAs of their cognate glycoprotein antigens led to the recognition that the different antigens were one and the same molecule. The Sixth International Workshop on Leukocyte Typing (1996) subsequently categorized these antibodies as CD63 antibodies. Prior to the 1996 Workshop, CD63 was known by multiple names (melanoma 1 antigen, ocular melanoma-associated antigen, melanoma associated antigen ME491, lysosome-associated membrane glycoprotein 3, granulophysin, melanoma-associated antigen MLA1), which were sometimes related to the antibodies that led to its partial characterization and identification. Thus, CD63 was also designated as antigen ME491 (MAb ME491), neuroglandular antigen (MAbs LS59, LS62, LS76, LS113, LS140 and LS152), Pltgp40 (MAbs H5C6, H4F8 and H5D2), human bone marrow stromal cell antigen (MAb 12F 12), osteoprogenitor-specific marker (MAb HOP-26), and integrin-associated protein (MAb 6H1). Other antibodies that were found to cross react with human CD63 were 8-1H, 8-2A (cross-reactivity with ME491), NKI/C-3 and NKI/black-13 (Vannegoor and Rumke, 1986; Demetrick et al., 1992; Wang et al., 1992).

CD63 was initially cloned from a melanoma cDNA library using MAb ME491, one of a number of antibodies raised against a preparation of human melanoma cells. It was shown that the reactivity of MAb ME491 appeared to be inversely correlated with melanoma progression in a study of human melanoma biopsies. The reactivity of the ME491 antibody was low in normal melanocytes, higher in the early stages of melanoma progression (dysplastic nevi and radial growth phase (RGP) tumors) and decreased or even absent in more advanced melanoma tumors such as those in the vertical growth phase (VGP) and in metastatic tumors.

CD63 was also found and partially characterized in human platelets using MAb 2.28 (raised against activated platelets) that detected an activation-dependent platelet membrane 53 kDa glycoprotein. This molecule was also associated with the membrane of internal granules in unstimulated platelets. In the same study MAb 2.28 also labelled internal granules in megakaryocytes and endothelial cells, where it co-localized with antibodies to the enzyme cathepsin D, a known marker of lysosomal compartments. Follow up studies with antibody clustering and expression cloning, led to the identification of the antigen recognized by this antibody as CD63, and further confirmed its presence in lysosomal compartments, where it co-localized with the compartment-specific markers LAMP-1 and LAMP-2. Cloning of this molecule identified it as CD63 and allowed its inclusion in the tetraspanin family.

Expression of CD63 was detected in many different tissues and cell types. At the cellular level it was found to be associated with the plasma membrane and also with intracellular late endosomal vesicular structures. Cell activation led, in certain cases, to increased surface expression by mobilization of intracellular stores of CD63. CD63 was also found to co-localize, and physically associate, with MHC class II in B-lymphocytes, particularly in endosomes, in exosomes involved in exporting MHC class II complexes to the surface, and in secreted vesicles. CD63 was found to interact with other members of the tetraspanin family, such as CD9, CD81, CD11 (integrin chain $\alpha_{M,L,X}$), CD18 (integrin chain $\beta_2$), CD49c (VLA-3 or integrin chain $\alpha_3$), CD49d (integrin chain $\alpha_4$), CD49f (VLA-6 or integrin chain $\alpha_6$) and CD29 (integrin chain $\beta_1$), in a variety of cell types including B- and T-lymphocytes, neutrophils, breast cancer and melanoma cells.

The role of CD63 in cancer has been unclear. Although CD63 was initially discovered by several independent groups to be involved in diverse events such as platelet and granulocyte activation, MHC class II-dependent antigen presentation, integrin-dependent cell adhesion and motility, and tumor progression in certain types of cancers, its function has yet to be fully elucidated. Even though current evidence supports its role in a variety of cellular physiological events, it is not clear if these functions are independent of each other or if there is an underlying common cellular mechanism in which CD63 is involved.

Several groups have investigated the association between CD63 and the progression of certain types of tumors, particularly melanomas. A number of other anti-CD63 monoclonal antibodies, in addition to Mab ME491, were developed for immunohistochemical (IHC) staining of cancer samples obtained from patients with tumors at various stages of progression. It was observed that decreased staining, interpreted by the authors as most likely reflecting decreased expression of CD63, correlated with advanced progression and with metastatic characteristics of the tumors. A more recent study, also described a significant correlation between the apparent decreased expression levels (after quantitation of mRNA) of several members of the tetraspanin protein family, including CD63, and the in vitro invasiveness of several mammary carcinoma-derived cell lines. Another study identified CD63, by differential display, in cultured breast cancer cells subjected to estrogen deprivation. This indicated that CD63 expression can be steroid-hormone regulated and that altered CD63 abundance and/or function might also be associated with breast tumor progression.

By contrast, work with anti-CD63 monoclonal antibody MAb FC-5.01 revealed that its reactive epitope was variably expressed in different normal tissues. Although this antibody was found to recognize CD63, it did not distinguish between early and more advanced stage melanomas, including metastatic melanomas (unlike MAb ME491), which suggested that the CD63 antigen was present in these more advanced tumors, but that some of its epitopes may have been masked in the cells from tumors at different stages. This might have been due to altered post-translational modifications of the core CD63 polypeptide, or to the interaction of CD63 with other molecules, which might have affected the availability of specific epitopes for antibody recognition and binding. These results supported the observation, described by Si and Hersey (1993), that staining with the anti-CD63 MAb NKI-C3, did not distinguish between tissue sections from melanomas at different stages of progression, such as primary, radial growth phase, vertical growth phase, and metastatic melanomas. Although in other studies (Adachi et al., 1998; Huang et al., 1998) analysis of mRNA from breast, and from non-small-cell lung cancers, by quantitative PCR, revealed that for two tetraspanin family members (CD9 and CD82) there was a significant correlation between their expression levels and tumor progression and patient prognosis, no such correlation was found for CD63, in that its expression was similar in all the samples. As a result of these, apparently conflicting, results, there is lack of strong and consistent data that would definitively demonstrate the association of CD63 with cancer.

To date very few in vivo studies have attempted to establish a link between CD63 and an eventual tumor suppressor function of this molecule. In one of these studies, human CD63-overexpressing H-ras-transformed NIH-3T3 cells, injected both subcutaneously and intraperitoneally into athymic mice, revealed a decreased malignant/tumorigenic phenotype, as indicated by decreased tumor size and metastatic potential as well as by increased survival time, when compared to the behavior of the parental non-CD63-overexpressing cells. This suggested that the presence of human CD63 in the transformed cells might suppress their malignant behavior. More recently, work with a transgenic mouse model expressing human CD63, and developed to induce tolerance to CD63, indicated that tumor growth of an injected human CD63-MHC class I (H-2K$^b$) co-transfected murine melanoma cell line could be inhibited, and survival increased, upon immunization with human CD63 fused to vaccinia virus. It was suggested by the authors that the therapeutic effect was T-lymphocyte dependent, and that endogenous anti-CD63 antibodies did not appear to be involved in this protective effect, since tumor growth inhibition only occurred when animals were injected with the CD63-MHC class I co-transfected cells and not with the CD63-only transfected cell line. This interpretation was supported by the fact that in wild type animals, pre-immunized with purified human CD63 and shown to have developed anti-human CD63 antibodies, there was no protective effect against tumor cell growth. Work described by Radford et al. (1995) using the KM3 cell line, initially thought to be of human origin but later characterized as being of rat lineage, transfected with human CD63, suggested that expression of this protein decreased the growth and metastastic potential of these cells, relative to that observed using the parental non-transfected KM3 cells, when injected intradermally into athymic mice, although there was no significant difference between the in vitro growth rates of the various transfected and non-transfected cell lines. These observations distinguished the potential effect of CD63 from that of other tumor suppressor genes known to affect both the in vivo and the in vitro growth rates of tumor cells. Furthermore, addition of the anti-CD63 monoclonal antibody ME491, which was found to have a functional effect on the same cells by decreasing their random motility in an in vitro assay (Radford et al., 1997), did not impact their in vitro growth rates.

This study also described the observation that CD63 may promote migration in response to extracellular matrix (ECM)-derived chemoattractants, such as laminin, fibronectin, collagen and vitronectin, and that this effect may be mediated by the functional involvement of $\beta_1$-type integrins, although antibodies to the integrins were unable to block these effects. However, there appeared to be an antagonistic effect between the role of vitronectin-mediated signaling (a known ligand for the integrin $\alpha_v\beta_5$) and that of the signaling mediated by other ECM components such as fibronectin, laminin and collagen on CD63 transfected cells. This suggested that under specific conditions, in the presence of ECM components, expression of CD63 may lead to decreased migration, and that this may be dependent on a fine balance between adhesion and motility. In another study, an anti-CD63 monoclonal antibody (MAb 710F) enhanced the adhesion and spreading of PMA-treated HL-60 cells, while another anti-CD63 monoclonal antibody (MAb 2.28), promoted a similar effect, but only on a much smaller fraction of the cell population, and only when added in much larger amounts. These results showed that although many antibodies to CD63 have been developed, their functional effects can be quite different.

Tetraspanins may also be involved in cell proliferation. Oren et al. (1990) described anti-proliferative effects of the murine MAb 5A6, that recognizes CD81 (TAPA-1), on lymphoma cell lines. In another study, ligation of CD37 in human T-lymphocytes with antibodies blocked CD37-induced proliferation. More recently, a study with an animal model deficient in the expression of CD37 (CD37 knockout) revealed that T lymphocytes from this animal were hyperproliferative compared to those from wild type animals in response to concanavalin A activation and CD3/T cell receptor engagement. It was therefore proposed that a functional role in cell growth and proliferation might be a common feature of the tetraspanin family. Recent studies with hepatoblastoma and hepatocellular carcinoma cells revealed that engagement of these cells with anti-CD81 monoclonal antibodies led to activation of the Erk/MAP kinase pathway. This signaling pathway has been shown to be involved with cell growth and proliferation events. In parallel work, transfected cell lines overexpressing human CD81 displayed increased proliferation relative to the mock-transfected control cells. Therefore, available evidence has pointed to a role of the tetraspanins in general, and of CD63 in particular, in events associated with cell growth proliferation and with cell adhesion/motility. These two types of cellular events are currently the target of intense research as both play a central role in tumor progression and metastasis.

Until now, no anti-CD63 antibodies, or other reagents that specifically targeted CD63-expressing cells, were reported and shown to have a simultaneous impact on the in vitro and on the in vivo growth characteristics of tumor cells, and also on the survival time of animal models of tumor cell growth.

Amino acid sequence determination and analysis did not reveal homology between tetraspanins and other protein families, or with any previously characterized functional modules, nor has it suggested any previously known enzymatic activity. As a result it has been very difficult to investigate the role of this family of proteins in the modulation of signal transduction pathways. However, the evidence generated using tetraspanin-specific reagents that led to changes in cellular physiology, and which were intimately dependent on the modulation of signal transduction pathways, suggests that tetraspanins have signal transduction properties. CD63 was shown to associate, both physically and functionally, with a number of molecules that are themselves either enzymes involved in the generation of secondary messenger signals, or are associated physically and/or functionally with such enzymes.

Experiments designed to dissect the mechanism controlling the interaction of human neutrophils with endothelial cells, which is one of the initial steps of the inflammatory response, revealed that pre-treatment of neutrophils with several anti-CD63 monoclonal antibodies (AHN-16, AHN-16.1, AHN-16.2, AHN-16.3 and AHN-16-5) promoted their adhesion to cultured endothelial cell layers. Furthermore this effect was strongly dependent on the presence of calcium ion ($Ca^{2+}$), a well-known modulator of many intracellular signaling pathways and which was restricted to a specific period of time during which the cells were exposed to the stimulating antibodies. After longer exposure to the antibody, adhesion of the neutrophils to the endothelial cells became insensitive to the later addition of $Ca^{2+}$, therefore implicating a dynamic and temporally regulated (transitory) event. In addition, CD63 was found to physically interact with the CD11/CD18 protein complex, and reagents that specifically targeted this complex mediated a modulatory signal. In this study CD63 was also found to be physically associated with, or to be part of, a complex that included the enzyme tyrosine kinases Lck and Hck. These enzymes are members of a class of proteins that play a central role in mediating intracellular regulatory signals upon activation of specific surface receptors and are part of cascades of signaling pathways that result in cell-specific physiological changes. Another study suggested that co-ligation of tetraspanins (including CD63) with monoclonal antibodies could enhance the phosphorylation or activity of the enzyme focal adhesion kinase (FAK) that was induced by adhesion of MDA-MB-231 breast cancer cells to collagen substrate. This pointed to a direct involvement of CD63 (and of other tetraspanin family members) in the modulation of integrin-mediated tyrosine kinase signaling pathways. Other signaling pathways that may functionally intersect with the presence and ligation of surface CD63 by the anti-CD63 monoclonal antibody MAb 710F appear to be those dependent on modulation of phosphorylation by the enzyme protein kinase C (PKC), another well known modulator of intracellular signaling pathways. In this context, enhancement of adhesion and of morphological changes in the myeloid cell line HL-60 by MAb 710F was dependent on pre-treatment of the cells with phorbol myristate acetate (PMA) although the temporal involvement of PKC was not conclusively demonstrated. However, later work by an independent group demonstrated that PMA-induced HL-60 differentiation was PKC-activity dependent since the molecule Ro31-8220, a specific inhibitor of this enzyme, blocked the effect of PMA.

Further evidence supporting the association of CD63, and other tetraspanin family members, with signal transduction pathways, arose from work that described a physical association, either direct or as part of a supramolecular complex, between CD63 (and also CD53) molecules with tyrosine phosphatase activity. In this study, immunoprecipitate complexes isolated with anti-CD63 antibodies were shown to be associated with tyrosine phosphatase activity, although unlike for CD53, which was shown to associate with the tyrosine phosphatase CD45, it was not possible to identify the CD63-associated phosphatase. More recently several members of the tetraspanin family were also found to be associated with a type II phosphatidylinositol 4-kinase (type II PI 4-K) (Berditchevski et al., 1997). This interaction appeared to be very specific since it was only identified for CD9, CD63, CD81, CD151 and A15/TALLA, and it was not observed to occur with CD37, CD52, CD82, or NAG-2. In addition, the association between tetraspanin family members and PI-4K was mutually exclusive since each PI-4 kinase-containing complex was limited to a single tetraspanin family member. CD63-PI-4 kinase complexes, in particular, were found, almost entirely, in intracellular compartments in lipid raft-like domains, unlike those formed with the other tetraspanin members. This observation suggested that this CD63 fraction, found to interact with the PI-4 kinase, might have been involved in specific intracellular events (Claas, C, et al., 2001) related to, or dependent from, phosphoinositide biosynthesis pathways, which are well known for their involvement in the regulation of membrane trafficking (endocytosis and exocytosis) and of cytoskeleton reorganization, in addition to their function as secondary messenger molecules (Martin, T., 1998).

The direct and important involvement of all the enzymes, that CD63 was found until now to be directly associated with, in the regulation of signaling pathways provided further evidence in support of the association of CD63 with the modulation of signal transduction pathways, either as a regulator or as an effector molecule downstream from the activity of these enzymes.

Elucidation of the mechanisms that lead to tumor progression is a very difficult and complex endeavor frequently marked by apparently contradictory observations and, as a result, it rare that those observations successfully translate into effective therapies. In view of what is currently known about the association of CD63 with tumor progression and metastasis and with signal transduction mechanisms, it is possible that its function may be altered, in tumor cells.

Development of antigen-specific reagents with cytotoxic effects on tumor cells, that bind cells expressing the recognized antigen(s) and which by themselves, or associated with other molecules, have cellular and in vivo physiological activity such that these reagents inhibit tumor cell growth, progression and metastasis, without significant deleterious effects on normal cell populations, would be extremely beneficial as a potential therapeutic and or diagnostic tool.

Monoclonal Antibodies as Cancer Therapy: Each individual who presents with cancer is unique and has a cancer that is as different from other cancers as that person's identity. Despite this, current therapy treats all patients with the same type of cancer, at the same stage, in the same way. At least 30% of these patients will fail the first line therapy, thus leading to further rounds of treatment and the increased probability of treatment failure, metastases, and ultimately, death. A superior approach to treatment would be the customization of therapy for the particular individual. The only current therapy which lends itself to customization is surgery. Chemotherapy and radiation treatment cannot be tailored to the patient, and surgery by itself, in most cases is inadequate for producing cures.

With the advent of monoclonal antibodies, the possibility of developing methods for customized therapy became more realistic since each antibody can be directed to a single epitope. Furthermore, it is possible to produce a combination of antibodies that are directed to the constellation of epitopes that uniquely define a particular individual's tumor.

Having recognized that a significant difference between cancerous and normal cells is that cancerous cells contain antigens that are specific to transformed cells, the scientific community has long held that monoclonal antibodies can be designed to specifically target transformed cells by binding specifically to these cancer antigens; thus giving rise to the belief that monoclonal antibodies can serve as "Magic Bullets" to eliminate cancer cells. However, it is now widely recognized that no single monoclonal antibody can serve in all instances of cancer, and that monoclonal antibodies can be deployed, as a class, as targeted cancer treatments. Monoclonal antibodies isolated in accordance with the teachings of the instantly disclosed invention have been shown to modify the cancerous disease process in a manner which is beneficial to the patient, for example by reducing the tumor burden, and will variously be referred to herein as cancerous disease modifying antibodies (CDMAB) or "anti-cancer" antibodies.

At the present time, the cancer patient usually has few options of treatment. The regimented approach to cancer therapy has produced improvements in global survival and morbidity rates. However, to the particular individual, these improved statistics do not necessarily correlate with an improvement in their personal situation.

Thus, if a methodology was put forth which enabled the practitioner to treat each tumor independently of other patients in the same cohort, this would permit the unique approach of tailoring therapy to just that one person. Such a course of therapy would, ideally, increase the rate of cures, and produce better outcomes, thereby satisfying a long-felt need.

Historically, the use of polyclonal antibodies has been used with limited success in the treatment of human cancers. Lymphomas and leukemias have been treated with human plasma, but there were few prolonged remission or responses. Furthermore, there was a lack of reproducibility and there was no additional benefit compared to chemotherapy. Solid tumors such as breast cancers, melanomas and renal cell carcinomas have also been treated with human blood, chimpanzee serum, human plasma and horse serum with correspondingly unpredictable and ineffective results.

There have been many clinical trials of monoclonal antibodies for solid tumors. In the 1980s there were at least four clinical trials for human breast cancer which produced only one responder from at least 47 patients using antibodies against specific antigens or based on tissue selectivity. It was not until 1998 that there was a successful clinical trial using a humanized anti-Her2/neu antibody (Herceptin®) in combination with Cisplatin. In this trial 37 patients were assessed for responses of which about a quarter had a partial response rate and an additional quarter had minor or stable disease progression. The median time to progression among the responders was 8.4 months with median response duration of 5.3 months.

Herceptin® was approved in 1998 for first line use in combination with Taxol®. Clinical study results showed an increase in the median time to disease progression for those who received antibody therapy plus Taxol® (6.9 months) in comparison to the group that received Taxol® alone (3.0 months). There was also a slight increase in median survival; 22 versus 18 months for the Herceptin® plus Taxol® treatment arm versus the Taxol® treatment alone arm. In addition, there was an increase in the number of both complete (8 versus 2 percent) and partial responders (34 versus 15 percent) in the antibody plus Taxol® combination group in comparison to Taxol® alone. However, treatment with Herceptin® and Taxol® led to a higher incidence of cardiotoxicity in comparison to Taxol® treatment alone (13 versus 1 percent respectively). Also, Herceptin® therapy was only effective for patients who over express (as determined through immunohistochemistry (IHC) analysis) the human epidermal growth factor receptor 2 (Her2/neu), a receptor, which currently has no known function or biologically important ligand; approximately 25 percent of patients who have metastatic breast cancer. Therefore, there is still a large unmet need for patients with breast cancer. Even those who can benefit from Herceptin® treatment would still require chemotherapy and consequently would still have to deal with, at least to some degree, the side effects of this kind of treatment.

The clinical trials investigating colorectal cancer involve antibodies against both glycoprotein and glycolipid targets. Antibodies such as 17-1A, which has some specificity for adenocarcinomas, has undergone Phase 2 clinical trials in over 60 patients with only 1 patient having a partial response. In other trials, use of 17-1A produced only 1 complete response and 2 minor responses among 52 patients in protocols using additional cyclophosphamide. To date, Phase III clinical trials of 17-1A have not demonstrated improved efficacy as adjuvant therapy for stage III colon cancer. The use of a humanized murine monoclonal antibody initially approved for imaging also did not produce tumor regression.

Only recently have there been any positive results from colorectal cancer clinical studies with the use of monoclonal antibodies. In 2004, ERBITUX® was approved for the second line treatment of patients with EGFR-expressing metastatic colorectal cancer who are refractory to irinotecan-based chemotherapy. Results from both a two-arm Phase II clinical study and a single arm study showed that ERBITUX® in combination with irinotecan had a response rate of 23 and 15 percent respectively with a median time to disease progression of 4.1 and 6.5 months respectively. Results from the same two-arm Phase II clinical study and another single arm study showed that treatment with ERBITUX® alone resulted in an 11 and 9 percent response rate respectively with a median time to disease progression of 1.5 and 4.2 months respectively.

Consequently in both Switzerland and the United States, ERBITUX® treatment in combination with irinotecan, and in the United States, ERBITUX® treatment alone, has been approved as a second line treatment of colon cancer patients who have failed first line irinotecan therapy. Therefore, like Herceptin®, treatment in Switzerland is only approved as a combination of monoclonal antibody and chemotherapy. In addition, treatment in both Switzerland and the US is only approved for patients as a second line therapy. Also, in 2004, AVASTIN® was approved for use in combination with intravenous 5-fluorouracil-based chemotherapy as a first line treatment of metastatic colorectal cancer. Phase III clinical study results demonstrated a prolongation in the median survival of patients treated with AVASTIN® plus 5-fluorouracil compared to patients treated with 5-fluourouracil alone (20 months versus 16 months respectively). However, again like Herceptin® and ERBITUX®, treatment is only approved as a combination of monoclonal antibody and chemotherapy.

There also continues to be poor results for lung, brain, ovarian, pancreatic, prostate, and stomach cancer. The most promising recent results for non-small cell lung cancer came from a Phase II clinical trial where treatment involved a monoclonal antibody (SGN-15; dox-BR96, anti-Sialyl-LeX) conjugated to the cell-killing drug doxorubicin in combination with the chemotherapeutic agent Taxotere. Taxotere is the only FDA approved chemotherapy for the second line treatment of lung cancer. Initial data indicate an improved overall survival compared to Taxotere alone. Out of the 62 patients who were recruited for the study, two-thirds received SGN-15 in combination with Taxotere while the remaining one-third received Taxotere alone. For the patients receiving SGN-15 in combination with Taxotere, median overall survival was 7.3 months in comparison to 5.9 months for patients receiving Taxotere alone. Overall survival at 1 year and 18 months was 29 and 18 percent respectively for patients receiving SNG-15 plus Taxotere compared to 24 and 8 percent respectively for patients receiving Taxotere alone. Further clinical trials are planned.

Preclinically, there has been some limited success in the use of monoclonal antibodies for melanoma. Very few of these antibodies have reached clinical trials and to date none have been approved or demonstrated favorable results in Phase III clinical trials.

The discovery of new drugs to treat disease is hindered by the lack of identification of relevant targets among the products of 30,000 known genes that unambiguously contribute to disease pathogenesis. In oncology research, potential drug targets are often selected simply due to the fact that they are over-expressed in tumor cells. Targets thus identified are then screened for interaction with a multitude of compounds. In the case of potential antibody therapies, these candidate compounds are usually derived from traditional methods of monoclonal antibody generation according to the fundamental principles laid down by Kohler and Milstein (1975, Nature, 256, 495-497, Kohler and Milstein). Spleen cells are collected from mice immunized with antigen (e.g. whole cells, cell fractions, purified antigen) and fused with immortalized hybridoma partners. The resulting hybridomas are screened and selected for secretion of antibodies which bind most avidly to the target. Many therapeutic and diagnostic antibodies directed against cancer cells, including Herceptin® and RITUXIMAB, have been produced using these methods and selected on the basis of their affinity. The flaws in this strategy are twofold. Firstly, the choice of appropriate targets for therapeutic or diagnostic antibody binding is limited by the paucity of knowledge surrounding tissue specific carcinogenic processes and the resulting simplistic methods, such as selection by overexpression, by which these targets are identified. Secondly, the assumption that the drug molecule that binds to the receptor with the greatest affinity usually has the highest probability for initiating or inhibiting a signal may not always be the case.

Despite some progress with the treatment of breast and colon cancer, the identification and development of efficacious antibody therapies, either as single agents or co-treatments, has been inadequate for all types of cancer.

Prior Patents:

US05296348 teaches methods for selecting monoclonal antibodies specific for cancer cell surface antigens that are internalizing, and for identifying monoclonal antibodies having anti-transcriptional and/or anti-replicational effects on cell metabolism. By way of example the ME491 antibody was shown to internalize in W9, WM35, WM983 melanoma cells, and SW948 colorectal carcinoma cells. In addition ME491 antibody was shown to decrease transcription and cell proliferation in SW948 cells. The patent application US20030211498A1 (and its related applications: WO0175177A3, WO0175177A2, AU0153140A5) allege a method of inhibiting the growth or metastasis of an ovarian tumor with an antibody that binds an ovarian tumor marker polypeptide encoded by an ovarian tumor marker gene selected from among a group that includes CD63 antigen. Serial analysis of gene expression using ovarian cancer was carried out to identify ovarian tumor marker genes which lead to the identification of CD63 as a candidate. The patent application WO02055551A1 (and its related application CN1364803A) alleges a new polypeptide-human CD63 antigen 56.87. The patent application CN1326962A alleges a new polypeptide-human CD63 antigen 14.63. The patent application CN1326951A alleges a new polypeptide-human CD63 antigen 15.07. The patent application CN1351054A alleges a new polypeptide-human CD63 antigen 11.11. These patents and patent applications identify CD63 antigens and antibodies but fail to disclose the isolated monoclonal antibody of the instant invention, or the utility of the isolated monoclonal antibody of the instant invention.

The gene encoding the ME491 polypeptide antigen was cloned and the sequence was received for publication on Feb. 24, 1988 (Can Res 48:2955, 1988, Jun. 1); the gene encoding CD63 was cloned and the sequence published in February 1991 (JBC 266(5):3239-3245, 1991) and the publication clearly indicated the identity of ME491 with CD63.

WO2004041170.89 (Sequence ID No.: 89, priority filing date: 29-Jun.-2004), WO2003068268-A2 (Sequence ID No.: 1, priority filing date: 13-Feb.-2003(2003WO-EP001461); other priority date: 14-Feb.-2002(2002GB-00003480)), WO2003057160-A29 (Sequence ID No.: 40, priority filing date: 30-Dec.-2002(2002WO-US041798); other priority date: 02-Jan.-2002(2002US-0345444P)) all allege polypeptides that have 100% sequence homology to CD63.

WO2003016475-A2(Sequence ID No.: 9787&12101, priority filing date: 14-Aug.-2002 (2002WO-US025765); other priority date: 14-Aug.-2001(2001 US-0312147P) allege polypeptides that have 100% sequence homology with 237 amino acids of 238 amino acids comprising CD63.

WO2003070902-A2(Sequence ID No.:27, priority filing date: 18-Feb.-2003(2003WO-US004902); other priority date: 20-Feb.-2002(2002US-0358279P)) allege polypeptides that have 94% sequence homology with 224 amino acids of 238 amino acids comprising CD63.

EP1033401-A2 (Sequence ID No.: 4168&4913, priority filing date: 21 Feb. 2000(2000EP-00200610); other priority date: 26 Feb. 1999(99US-0122487P)) allege polypeptides that have 100% sequence homology with 205 amino acids and with 94 amino acids of 238 amino acids comprising CD63, respectively.

WO200257303-A2 (Human prey protein for Shigella ospG#26, priority filing date: 11-Jan.-2002(2002WO-EP000777); other priority date: 12-Jan.-2001(2001US-0261130P)) allege polypeptides that have 100% sequence homology with 130 amino acids of 238 amino acids comprising CD63.

WO200055180-A2 (Sequence ID No.: 756, priority filing date: 08-Mar.-2000(2000WO-US005918); other priority date: 12-Mar.-1999(99US-0124270P)) allege polypeptides that have 99% sequence homology with 127 amino acids of 238 amino acids comprising CD63.

WO200200677-A1 (Sequence ID No.:3203, priority filing date: 07-Jun.-2001(2001WO-US018569); other priority date: 07-Jun.-2000(2000US-0209467P)) allege polypeptides that have 97% sequence homology with 132 amino acids of 238 amino acids comprising CD63.

WO9966027-A1 (Large extracellular loop sequence from human CD63 protein, priority filing date: 15-Jun.-1999 (99WO-US013480); other priority date: 15-Jun.-1998 (98US-0089226P)) allege polypeptides that have 100% sequence homology with 99 amino acids of 238 amino acids comprising CD63.

WO200270539-A2 (Sequence ID No.: 1207, priority filing date: 05-Mar.-2002(2002WO-US005095); other priority date: 05 Mar. 2001(2001US-00799451)) allege polypeptides that have 86% sequence homology with 102 amino acids of 238 amino acids comprising CD63.

EP1033401-A2 (Sequence ID No.: 4169, 21-Feb.-2000 (2000EP-00200610); other priority date: 26-Feb.-1999

(99US-0122487P)) allege polypeptides that have 100% sequence homology with 74 amino acids of 238 amino acids comprising CD63.

These patent applications identify polypeptides that have varying sequence homology to CD63 antigen. In most cases these application also allege antibodies and anitbody derivatives to the corresponding polypepide and their homologs but fail to disclose the isolated monoclonal antibody of the instant invention, or the utility of the applications monoclonal antibody of the instant invention. Importantly, all the above applications were filed after the publication of the sequence of the polynucleotide encoding CD63.

SUMMARY OF THE INVENTION

The instant inventors have previously been awarded U.S. Pat. No. 6,180,357, entitled "Individualized Patient Specific Anti-Cancer Antibodies" directed to a process for selecting individually customized anti-cancer antibodies which are useful in treating a cancerous disease. It is well recognized in the art that some amino acid sequence can be varied in a polypeptide without significant effect on the structure or function of the protein. In the molecular rearrangement of antibodies, modifications in the nucleic or amino acid sequence of the backbone region can generally be tolerated. These include, but are not limited to, substitutions (preferred are conservative substitutions), deletions or additions. Furthermore, it is within the purview of this invention to conjugate standard chemotherapeutic modalities, e.g. radionuclides, with the CDMAB of the instant invention, thereby focusing the use of said chemotherapeutics. The CDMAB can also be conjugated to toxins, cytotoxic moieties, enzymes e.g. biotin conjugated enzymes, or hematogenous cells, thereby forming an antibody conjugate.

This application utilizes the method for producing patient specific anti-cancer antibodies as taught in the '357 patent for isolating hybridoma cell lines which encode for cancerous disease modifying monoclonal antibodies. These antibodies can be made specifically for one tumor and thus make possible the customization of cancer therapy. Within the context of this application, anti-cancer antibodies having either cell-killing (cytotoxic) or cell-growth inhibiting (cytostatic) properties will hereafter be referred to as cytotoxic. These antibodies can be used in aid of staging and diagnosis of a cancer, and can be used to treat tumor metastases. These antibodies can also be used for the prevention of cancer by way of prophylactic treatment. Unlike antibodies generated according to traditional drug discovery paradigms, antibodies generated in this way may target molecules and pathways not previously shown to be integral to the growth and/or survival of malignant tissue. Furthermore, the binding affinity of these antibodies are suited to requirements for initiation of the cytotoxic events that may not be amenable to stronger affinity interactions.

The prospect of individualized anti-cancer treatment will bring about a change in the way a patient is managed. A likely clinical scenario is that a tumor sample is obtained at the time of presentation, and banked. From this sample, the tumor can be typed from a panel of pre-existing cancerous disease modifying antibodies. The patient will be conventionally staged but the available antibodies can be of use in further staging the patient. The patient can be treated immediately with the existing antibodies, and a panel of antibodies specific to the tumor can be produced either using the methods outlined herein or through the use of phage display libraries in conjunction with the screening methods herein disclosed. All the antibodies generated will be added to the library of anti-cancer antibodies since there is a possibility that other tumors can bear some of the same epitopes as the one that is being treated. The antibodies produced according to this method may be useful to treat cancerous disease in any number of patients who have cancers that bind to these antibodies.

In addition to anti-cancer antibodies, the patient can elect to receive the currently recommended therapies as part of a multi-modal regimen of treatment. The fact that the antibodies isolated via the present methodology are relatively non-toxic to non-cancerous cells allows for combinations of antibodies at high doses to be used, either alone, or in conjunction with conventional therapy. The high therapeutic index will also permit re-treatment on a short time scale that should decrease the likelihood of emergence of treatment resistant cells.

If the patient is refractory to the initial course of therapy or metastases develop, the process of generating specific antibodies to the tumor can be repeated for re-treatment. Furthermore, the anti-cancer antibodies can be conjugated to red blood cells obtained from that patient and re-infused for treatment of metastases. There have been few effective treatments for metastatic cancer and metastases usually portend a poor outcome resulting in death. However, metastatic cancers are usually well vascularized and the delivery of anti-cancer antibodies by red blood cells can have the effect of concentrating the antibodies at the site of the tumor. Even prior to metastases, most cancer cells are dependent on the host's blood supply for their survival and an anti-cancer antibody conjugated to red blood cells can be effective against in situ tumors as well. Alternatively, the antibodies may be conjugated to other hematogenous cells, e.g. lymphocytes, macrophages, monocytes, natural killer cells, etc.

There are five classes of antibodies and each is associated with a function that is conferred by its heavy chain. It is generally thought that cancer cell killing by naked antibodies are mediated either through antibody dependent cellular cytotoxicity or complement dependent cytotoxicity. For example murine IgM and IgG2a antibodies can activate human complement by binding the C1 component of the complement system thereby activating the classical pathway of complement activation which can lead to tumor lysis. For human antibodies the most effective complement activating antibodies are generally IgM and IgG1. Murine antibodies of the IgG2a and IgG3 isotype are effective at recruiting cytotoxic cells that have Fc receptors which will lead to cell killing by monocytes, macrophages, granulocytes and certain lymphocytes. Human antibodies of both the IgG1 and IgG3 isotype mediate ADCC.

Another possible mechanism of antibody mediated cancer killing may be through the use of antibodies that function to catalyze the hydrolysis of various chemical bonds in the cell membrane and its associated glycoproteins or glycolipids, so-called catalytic antibodies.

There are three additional mechanisms of antibody-mediated cancer cell killing. The first is the use of antibodies as a vaccine to induce the body to produce an immune response against the putative antigen that resides on the cancer cell. The second is the use of antibodies to target growth receptors and interfere with their function or to down regulate that receptor so that its function is effectively lost. The third is the effect of such antibodies on direct ligation of cell surface moieties that may lead to direct cell death, such as ligation of death receptors such as TRAIL R1 or TRAIL R2, or integrin molecules such as alpha V beta 3 and the like.

The clinical utility of a cancer drug is based on the benefit of the drug under an acceptable risk profile to the patient. In cancer therapy survival has generally been the most sought after benefit, however there are a number of other well-recognized benefits in addition to prolonging life. These other benefits, where treatment does not adversely affect survival, include symptom palliation, protection against adverse events, prolongation in time to recurrence or disease-free survival, and prolongation in time to progression. These criteria are generally accepted and regulatory bodies such as the U.S. Food and Drug Administration (F.D.A.) approve drugs that produce these benefits (Hirschfeld et al. Critical Reviews in Oncology/Hematolgy 42:137-143 2002). In addition to these criteria it is well recognized that there are other endpoints that may presage these types of benefits. In part, the accelerated approval process granted by the U.S. F.D.A. acknowledges that there are surrogates that will likely predict patient benefit. As of year-end (2003), there have been sixteen drugs approved under this process, and of these, four have gone on to full approval, i.e., follow-up studies have demonstrated direct patient benefit as predicted by surrogate endpoints. One important endpoint for determining drug effects in solid tumors is the assessment of tumor burden by measuring response to treatment (Therasse et al. Journal of the National Cancer Institute 92(3):205-216 2000). The clinical criteria (RECIST criteria) for such evaluation have been promulgated by Response Evaluation Criteria in Solid Tumors Working Group, a group of international experts in cancer. Drugs with a demonstrated effect on tumor burden, as shown by objective responses according to RECIST criteria, in comparison to the appropriate control group tend to, ultimately, produce direct patient benefit. In the pre-clinical setting tumor burden is generally more straightforward to assess and document. In that pre-clinical studies can be translated to the clinical setting, drugs that produce prolonged survival in pre-clinical models have the greatest anticipated clinical utility. Analogous to producing positive responses to clinical treatment, drugs that reduce tumor burden in the pre-clinical setting may also have significant direct impact on the disease. Although prolongation of survival is the most sought after clinical outcome from cancer drug treatment, there are other benefits that have clinical utility and it is clear that tumor burden reduction, which may correlate to a delay in disease progression, extended survival or both, can also lead to direct benefits and have clinical impact (Eckhardt et al. Developmental Therapeutics: Successes and Failures of Clinical Trial Designs of Targeted Compounds; ASCO Educational Book, 39$^{th}$ Annual Meeting, 2003, pages 209-219).

Using substantially the process of U.S. Pat. No. 6,180,357, and as disclosed in U.S. Pat. No. 6,657,048 and in Ser. No. 10/348,231 and Ser. No. 60/642,057 the contents of each of which are herein incorporated by reference, the mouse monoclonal antibodies, 7BDI-58, 7BDI-60, H460-22-1, 1A245.6 and 7BD-33-11A were obtained following immunization of mice with cells from a patient's lung (H460-22-1) or breast (7BDI-58, 7BDI-60, 7BD-33-11A and 1A245.6) tumor biopsy. The H460-22-1, 1A245.6 and 7BD-33-11A antigen was expressed on the cell surface of a wide range of human cell lines from different tissue origins. The 7BDI-58 and the 7BDI-60 antigen was expressed on the cell surface of breast cancer cells. The breast cancer cell line MDA-MB-231 (MB-231) and the melanoma cell line A2058 were susceptible to the cytotoxic effect of H460-22-1 in vitro. The breast cancer cell line MCF-7 and prostate cancer cell line PC-3 were susceptible to the cytotoxic effects of 1A245.6 and 7BD-33-11A in vitro. The breast cancer cell line Hs574.T was susceptible to the cytotoxic effects of 7BDI-58 and 7BDI-60 in vitro.

The result of H460-22-1 cytotoxicity against breast cancer cells in culture was further extended by its anti-tumor activity towards this cancer indication in vivo (as disclosed in Ser. No. 11/321,624). In the preventative in vivo model of human breast cancer, H460-22-1 was given to mice one day prior to implantation of tumor cells followed by weekly injections for a period of 7 weeks. H460-22-1 treatment was significantly (p<0.0001) more effective in suppressing tumor growth during the treatment period than an isotype control antibody. At the end of the treatment phase, mice given H460-22-1 had tumors that grew to only 17.7 percent of the control group. During the post treatment follow-up period, the treatment effects of H460-22-1 were sustained and the mean tumor volume in the treated group continued to be significantly smaller than controls until the end of the measurement phase.

Using survival as a measure of antibody efficacy, the control group reached 50 percent mortality between day 74-81 post-implantation. In contrast, the H460-22-1 treated group had not reached 50 percent mortality at the time of termination of the study. This difference was significant between H460-22-1 and isotype control treated group (p<0.0015). These data demonstrated that H460-22-1 treatment conferred a survival benefit compared to the control-treated group. H460-22-1 treatment appeared safe, as it did not induce any signs of toxicity, including reduced body weight and clinical distress. Thus, H460-22-1 treatment was efficacious as it both delayed tumor growth and enhanced survival compared to the control-treated group in a well-established model of human breast cancer. These results were also reproducible as similar findings were observed in another study of this kind and suggest its relevance and benefit to treatment of people with cancer.

Besides the preventative in vivo tumor model of breast cancer, H460-22-1 demonstrated anti-tumor activity against MB-231 cells in an established in vivo tumor model (as disclosed in Ser. No. 11/321,624). In this xenograft tumor model, MB-231 breast cancer cells were transplanted subcutaneously into immunodeficient mice such that the tumor reached a critical size before antibody treatment. Treatment with H460-22-1 was compared to the standard chemotherapeutic drug, cisplatin, and it was shown that the cisplatin and H460-22-1 treatment groups had significantly (p<0.001) smaller mean tumor volumes compared with the group treated with isotype control antibody. H460-22-1 treatment mediated tumor suppression that was approximately two-thirds that of cisplatin chemotherapy but without the significant weight loss (p<0.003) and clinical distress observed with cisplatin. The anti-tumor activity of H460-22-1 and its minimal toxicity make it an attractive anti-cancer therapeutic agent.

In the post-treatment period, H460-22-1 maintained tumor suppression by delaying tumor growth compared to the isotype control antibody group. At 31 days post treatment, H460-22-1 limited tumor size by reducing tumor growth by 42 percent compared to the isotype control group, which is comparable to the 48 percent reduction observed at the end of the treatment. In the established tumor model of breast cancer, these results indicated the potential of H460-22-1 to maintain tumor suppression beyond the treatment phase and demonstrated the ability of the antibody to reduce the tumor burden and enhance survival in a mammal.

The result of 1A245.6 and 7BD-33-11A cytotoxicity against breast and prostate cancer cells in culture was further extended by its anti-tumor activity towards these cancer indications in vivo (as disclosed in Ser. Nos. 10/348,231, 10/891, 866, 10/603,006 and 10/810,751).

7BD-33-11A and 1A245.6 prevented tumor growth and tumor burden in a MB-231 preventative in vivo model of human breast cancer. Monitoring continued past 300 days post-treatment. 7BD-33-11A never developed tumors and 87.5 percent of the 7BD-33-11A-treatment group was still alive at over 9 months post-implantation (one of the mice died from non-tumor related causes). Conversely, the isotype control group had 100 percent mortality by day 72 (23 days post-treatment). 1A245.6-treated mice reached 100 percent mortality by day 151 post-treatment, which is greater than 6 times longer than the isotype control treatment group. Therefore 1A245.6, and to a greater extent 7BD-33-11A enhanced survival and prevented tumor growth (thus delaying disease progression) in a breast cancer model.

7BD-33-11A and 1A245.6 also significantly suppressed tumor growth and decreased tumor burden in an established in vivo model of human breast cancer. By day 80 (23 days post-treatment), 7BD-33-11A treated mice had 83 percent lower mean tumor volumes in comparison to the isotype control group (p=0.001). 1A245.6 treatment reduced the mean tumor volumes on this day by 35 percent, however, the reduction did not reach significance in this experiment (p=0.135).

Using survival as a measure of antibody efficacy, it was estimated that the risk of dying in the 7BD-33-11A treatment group was about 16 percent of the isotype control group (p=0.0006) at around 60 days post-treatment. 100 percent of the isotype control group died by 50 days post-treatment. In comparison, 1A245.6-treated mice survived until 100 days post-treatment and 60 percent of the 7BD-33-11A treatment groups were still alive at 130 days post-treatment. This data demonstrated that both 1A245.6 and 7BD-33-11A treatment conferred a survival benefit and reduced tumor burden compared to the control treated group.

7BD-33-11A and 1A245.6 treatment appeared safe, as it did not induce any signs of toxicity, including reduced body weight and clinical distress. Thus, 7BD-33-11A and 1A245.6 treatment was efficacious as it both delayed tumor growth and enhanced survival compared to the control-treated group in a well-established model of human breast cancer.

In a study disclosed in Ser. No. 10/810,751, the contents of which are herein incorporated by reference, the effect of 7BD-33-11A compared to chemotherapeutic drug (Cisplatin) treatment alone or in combination was determined in two different established breast cancer xenograft models.

In the MB-231 model, at day 83 (20 days after treatment), 7BD-33-11A treatment resulted in an 83 percent reduction in tumor growth relative to the buffer control treated animals (p=0.002). Cisplatin treatment alone resulted in a 77 percent reduction in tumor size relative to the control, while Cisplatin in combination with 7BD-33-11A resulted in an 88 percent reduction in tumor size relative to the control (p=0.006).

In the MDA-MB-468 (MB-468) model, at day 62 (12 days after treatment) the greatest reduction in tumor growth (97 percent, p=0.001) was observed with Cisplatin treatment in combination with 7BD-33-11A. Cisplatin treatment alone produced a 95 percent decrease in tumor growth in comparison to the buffer control while 7BD-33-11A treatment alone showed a 37 percent (p=0.046) reduction.

In both the MB-231 and MB-468 model, treatment with 7BD-33-11A led to greater animal well-being in comparison to treatment with Cisplatin as measured by body weight. These results indicated that 7BD-33-11A treatment had greater efficacy in comparison with Cisplatin treatment alone in the MB-231 model and was better tolerated with fewer adverse effects, such as weight loss, than Cisplatin in both breast cancer models.

To determine the effects of 7BD-33-11A treatment at various doses, a dose response experiment was performed in a preventative breast cancer xenograft model (as disclosed in Ser. No. 10/810,751). At day 55 (5 days after treatment), the 0.2 mg/kg treatment group had reduced tumor growth by 85 percent relative to the isotype control treated group. Also at day 55, both the 2 and 20 mg/kg treatment groups had yet to develop tumors. Similar results were obtained past day 125 (75 days after treatment), where the 20 mg/kg treatment group had still not developed tumors and the 2 mg/kg treatment group had some initial tumor growth. 7BD-33-11A treatment also demonstrated a survival benefit. All of the mice in the isotype control group had died by day 104 (54 days after treatment) while the 0.2 mg/kg 7BD-33-11A treatment group survived until day 197 (147 days after treatment). Even greater survival benefits were observed with the 2.0 and 20 mg/kg 7BD-33-11A treatment groups; only 50 percent of the 2.0 mg/kg treatment group had died by day 290 (240 days after treatment) while none of the 20 mg/kg treatment group had died by day 290. Therefore, 7BD-33-11A treatment showed significant tumor growth reduction and increased survival with all three doses with the greatest degree of efficacy being exhibited by the highest dose.

In addition to the beneficial effects in the established in vivo tumor model of breast cancer, 7BD-33-11A and 1A245.6 treatment also had anti-tumor activity against PC-3 cells in a preventative in vivo prostate cancer model (disclosed in Ser. Nos. 10/603,006 and 10/810,751, the contents of each of which are herein incorporated by reference). 7BD-33-11A and 1A245.6 treatment was significantly (p=0.001 and 0.017 respectively) more effective in suppressing tumor growth shortly after the treatment period than an isotype control antibody. At the end of the treatment phase, mice given 7BD-33-11A or 1A245.6 had tumors that grew to only 31 and 50 percent of the isotype control group respectively.

For PC-3 SCID xenograft models, body weight can be used as a surrogate indicator of disease progression. On day 52, 7BD-33-11A and 1A245.6 treatment significantly (p=0.002 and 0.004 respectively) prevented the loss of body weight by 54 and 25 percent respectively in comparison to isotype control. Mice were monitored for survival post-treatment. At 11 days post-treatment, isotype and buffer control mice had reached 100 percent mortality. Conversely, 7BD-33-11A and 1A245.6 reached 100 percent mortality at day 38 post-treatment, 3 times longer than the control groups. Thus, 7BD-33-11A and 1A245.6 treatment was efficacious as it both delayed tumor growth, prevented body weight loss and extended survival compared to the isotype control treated group in a well-established model of human prostate cancer.

In addition to the preventative in vivo tumor model of prostate cancer, 7BD-33-11A demonstrated anti-tumor activity against PC-3 cells in an established in vivo tumor model (disclosed in Ser. Nos. 10/603,006 and 10/810,751, the contents of each of which are herein incorporated by reference). Treatment with 7BD-33-11A was again compared to isotype control. It was shown that the 7BD-33-11A treatment group had significantly (p<0.024) smaller mean tumor volumes compared with the isotype control treated group immediately following treatment. 7BD-33-11A treatment mediated tumor suppression by 36 percent compared to the isotype control group.

In addition to the beneficial effects in the in vivo tumor models of breast and prostate cancer, 7BD-33-11A treatment also had anti-tumor activity against BxPC-3 cells in a preventative in vivo pancreatic cancer model (as disclosed in Ser. No. 11/321,624). 7BD-33-11A treatment was significantly more effective in suppressing tumor growth (71 percent, p=0.0009) shortly after the treatment period than the buffer control. In addition, 7BD-33-11A treatment conferred a survival benefit in comparison to the buffer control treatment group. In the 7BD-33-11A treated group, 40 percent of the mice were still alive over 2 weeks after all of the buffer control group mice had died.

In addition to the beneficial effects in the in vivo tumor models of breast, prostate and pancreatic cancer, 7BD-33-11A treatment also had anti-tumor activity against A2058 and A375 cells in two separate preventative in vivo melanoma cancer models (as disclosed in Ser. No. 11/321,624). In both the A2058 and A375 model, 7BD-33-11A treatment was significantly more effective in suppressing tumor growth (72 percent, p=0.011 and 63 percent, p=0.0006 respectively) than the buffer control. The anti-tumor activities of 7BD-33-11A in melanoma as well as in breast, prostate and pancreatic cancer models make it an attractive anti-cancer therapeutic agent.

In addition to the beneficial effects demonstrated in the preventative in vivo model of human melanoma, 7BD-33-11A-treatment also had anti-tumor activity against A2058 and A375 cells in two separate established in vivo melanoma cancer models (as disclosed in Ser. No. 11/321,624). Tumor growth was significantly inhibited in the 7BD-33-11A-treatment and the 7BD-33-11A plus dacarbazine treatment group for the A2058 and A375 model respectively. In the A2058 model, the mean tumor volume was 30.87% (p<0443) of the control group measurement. In the A375 model, the 7BD-33-11A/dacarbazinbe combination treatment group resulted in a median TTE (time-to-endpoint) of 39.1 days, corresponding to a significant 147% delay in tumor growth (p<0.01). No toxic deaths were observed in either model. Therefore, 7BD-33-11A treatment appeared safe and has displayed efficacy in the treatment of breast and now melanoma in vivo models of established human cancer.

To determine if the efficacy demonstrated by 7BD-33-11A in vivo is due in whole or in part to ADCC activity, 7BD-33-11A anti-tumor activity was measured against MB-231 cells in an established tumor model in both NOD SCID and SCID mice. NOD SCID mice are functionally deficit in natural killer (NK) cells and lack circulating complement and a functionally immature macrophage population while SCID mice have both complement and robust NK cell activity. 7BD-33-11A is a murine IgG2a monoclonal antibody and is therefore capable of ADCC activity in vivo. The anti-tumor activity of 7BD-33-11A was compared to both a buffer control and H460-22-1, a murine IgG1 monoclonal antibody that should not exhibit its activity through ADCC based on its isotype. On day 54 (4 days after the last treatment), in the SCID treated group, 7BD-33-11A and H460-22-1 treated mice developed tumors that were only 1.9 and 3.6 percent respectively of the mean tumor volume of the buffer control treated mice. Conversely, in the NOD SCID treated group, again on day 54 (4 days after the last treatment), 7BD-33-11A treated mice had tumor growth that was 67 percent of the mean tumor volume of the buffer control treated mice. H460-22-1 treated mice exhibited a similar effect as in the SCID mice; tumor growth was 1.4 percent of the mean tumor volume of the buffer control treated mice. Consequently, 7BD-33-11A activity in vivo seems to be in-part due to ADCC activity while H460-22-1's anti-tumor effect appears to be independent of ADCC.

In order to validate the H460-22-1, 1A245.6 and 7BD-33-11A epitope as a drug target, the expression of their target antigens in normal human tissues was determined. As partially disclosed in Ser. Nos. 10/603,006 and 10/810,751, the contents of each of which are herein incorporated by reference, the binding of 7BD-33-11A, H460-22-1 and 1A245.6 towards normal human tissues was determined. By IHC staining, the majority of the tissues failed to express the 7BD-33-11A antigen, including the vital organs, such as the kidney, heart, and lung. 7BD-33-11A stained the salivary gland, liver, pancreas, stomach, prostate and duodenum, and strongly stained the tonsil. Results from tissue staining indicated that 7BD-33-11A showed restricted binding to various cell types but had binding to infiltrating macrophages, lymphocytes, and fibroblasts. For both H460-22-1 and 1A245.6, a wider range of tissues was positively stained. For the majority of cases, staining was restricted to the epithelium or infiltrating macrophages, lymphocytes, and fibroblasts. However, positive staining was seen on both cardiac muscle and hepatocytes. 7BD-33-11A, H460-22-1 and 1A245.6 displayed both membrane and cytoplasmic staining patterns.

As disclosed in Ser. No. 10/810,751, the contents of which are herein incorporated by reference, 7BD-33-11A was compared with commercially available anti-CD63 antibodies (RFAC4 and H5C6). Results from normal human tissue staining indicated that 7BD-33-11A again showed restricted binding to various cell types but had binding to infiltrating macrophages, lymphocytes, and fibroblasts. The RFAC4 and H5C6 antibodies showed a similar staining pattern in comparison to each other. However, the staining pattern of both RFAC4 and H5C6 was quite different than that observed with 7BD-33-11A. Specifically, both RFAC4 and H5C6 antibodies bound to a broader range of normal tissues, usually had higher staining intensity in tissues where 7BD-33-11A was also positive and bound not only to infiltrating macrophages, lymphocytes and fibroblasts but also to the epithelium in a majority of the tissues.

Localization of the H460-22-1, 1A245.6 and 7BD-33-11A antigen and determination of their prevalence within the population, such as among breast cancer patients, is important in assessing the therapeutic use of these antibodies and designing effective clinical trials. To address H460-22-1, 1A245.6 and 7BD-33-11A antigen expression in breast tumors from cancer patients, tumor tissue samples from 98 individual breast cancer patients were screened for expression of the 7BD-33-11A antigen (results from 50 patients have been previously described in Ser. Nos. 10/603,006 and 10/810,751, the contents of each of which are herein incorporated by reference) and tumor tissue samples from 50 patients were screened for 1A245.6 (disclosed in Ser. No. 10/603,006, the contents of which are herein incorporated by reference) and H460-22-1 antigen (disclosed in Ser. No. 11/321,624, the contents of which are herein incorporated by reference).

The results of these studies showed that 37 percent of tissue samples positively stained for the 7BD-33-11A antigen. Expression of 7BD-33-11A within patient samples appeared specific for cancer cells as staining was restricted to malignant cells. In addition, 7BD-33-11A stained 0 of 20 samples of normal tissue from breast cancer patients. On the other hand, H460-22-1 and 1A245.6 stained 92 percent and 98 percent of breast cancer tissue samples respectively. H460-22-1 and 1A245.6 also stained 9 out of 10 samples of normal tissue from breast cancer patients. However, this staining was generally much weaker than that observed with the breast cancer tissue samples and was generally restricted to infiltrating fibroblasts. Breast tumor expression of the 7BD-33-11A, H460-22-1 and 1A245.6 antigen appeared to be localized to the cell membrane and cytoplasm of malignant cells, making CD63 an attractive target for therapy.

As disclosed in Ser. No. 10/810,751, the contents of which are herein incorporated by reference, 7BD-33-11A was compared to RFAC4 and H5C6 and to an anti-Her2 antibody (c-erbB-2). The results of the current study were similar to previous results and showed that 36 percent of tumor tissue samples stained positive for the 7BD-33-11A antigen while 94 and 85 percent of breast tumor tissues were positive for the H5C6 and RFAC4 epitope respectively. Expression of 7BD-33-11A within patient samples appeared specific for cancer cells as staining was restricted to malignant cells. In addition, 7BD-33-11A stained 0 of 10 samples of normal tissue from breast cancer patients while both H5C6 and RFAC4 stained 7 of 8 samples of normal breast tissue. In comparison to c-erbB-2, 7BD-33-11A showed a completely different staining profile where half of the breast tumor tissue samples that were positive for the 7BD-33-11A antigen were negative for Her2 expression indicating that 7BD-33-11A targets a patient population that is not served by existing antibody therapies. There were also differences in the intensity of staining between the breast tumor tissue sections that were positive for both 7BD-33-11A and Her2. The c-erbB-2 antibody also positively stained one of the normal breast tissue sections.

As disclosed in Ser. Nos. 10/603,006, 10/810,751 and 11/321,624, the contents of each of which are herein incorporated by reference, 7BD-33-11A, H460-22-1 and 1A245.6 expression was further evaluated based on breast tumor expression of the receptors for the hormones estrogen and progesterone, which play an important role in the development, treatment, and prognosis of breast tumors. No correlation was apparent between expression of the 1A245.6 antigen and expression of the receptors for either estrogen or progesterone. There was a slight correlation between absence of estrogen receptors and presence of progesterone receptors and 7BD-33-11A antigen expression and presence of both estrogen and progesterone receptors and H460-22-1 antigen expression. When tumors were analyzed based on their stage, or degree to which the cancer advanced, results suggested a trend towards greater positive expression with higher tumor stage for both 7BD-33-11A and H460-22-1. Similar results were obtained with RFAC4. H5C6 also showed a very slight correlation with estrogen or progesterone receptor expression but there was no apparent correlation with tumor stage, however, conclusions were limited by the small sample size.

Localization of the 7BD-33-11A antigen and its prevalence within prostate cancer patients is important in assessing the benefits of 7BD-33-11A immunotherapy to patients with prostate cancer and designing effective clinical trials. To address 7BD-33-11A antigen expression in prostate tumors from cancer patients, tumor tissue samples from 51 individual prostate cancer patients were screened for expression of the 7BD-33-11A antigen (as disclosed in Ser. No. 10/810,751, the contents of which are herein incorporated by reference). The results of the study showed that 88 percent of tissue samples stained positive for the 7BD-33-11A antigen. Although 7BD-33-11A stained the normal tissue sections with high intensity as well, there was a higher degree of membranous staining in the tumor tissue samples in comparison to the normal samples. There was one embryonal rhabdomyosarcoma tissue sample that did not stain for the 7BD-33-11A antigen. In the small sample size tested there did not appear to be a direct correlation between tumor stage and presence of the 7BD-33-11A antigen.

Localization of the 7BD-33-11A antigen and its prevalence within melanoma cancer patients is important in assessing the benefits of 7BD-33-11A immunotherapy to patients with melanoma and designing effective clinical trials. To address 7BD-33-11A antigen expression in melanoma tumors from cancer patients, tumor tissue samples from 39 individual melanoma patients were screened for expression of the 7BD-33-11A antigen (as disclosed in Ser. No. 11/321,624). The results of the study showed that 90 percent of tissue samples stained positive for the 7BD-33-11A antigen. In this small sample, there also appeared to be no direct correlation between tumor stage and presence of the 7BD-33-11A antigen.

To further extend the potential therapeutic benefit of 7BD-33-11A, H460-22-1 and 1A245.6, the frequency and localization of the antigen within various human cancer tissues was also determined (disclosed in Ser. Nos. 10/603,006, 10/810,751 and 11/321,624, the contents of each of which are herein incorporated by reference). Several cancer types, in addition to breast and prostate cancer, expressed the 7BD-33-11A antigen. The positive human cancer types included skin (1/2), lung (3/4), liver (2/3), stomach (4/5), thyroid (2/2), uterus (4/4) and kidney (3/3). Some cancers did not express the antigen; these included ovary (0/3), testis (0/1), brain (0/2) and lymph node (0/2). For H460-22-1 and 1A245.6, as with the normal human tissue array, a multitude of cancers from various human tissue types were positively stained. Greater staining was seen on malignant cells of the skin, lung, liver, uterus, kidney, stomach and bladder. As with human breast, prostate and melanoma cancer tissue, localization of 7BD-33-11A, H460-22-1 and 1A245.6 occurred both on the membrane and within the cytoplasm of these tumor cells. Therefore, in addition to the H460-22-1, 1A245.6 and 7BD-33-11A antibody binding to cancer cell lines in vitro, there is evidence that the antigen is expressed in humans, and on multiple types of cancers.

As disclosed in Ser. No. 10/810,751, the contents of which are herein incorporated by reference, for 7BD-33-11A and in Ser. No. 11/321,624 for 1A245.6 and H460-22-1, biochemical data also indicate that the antigen recognized by H460-22-1, 1A245.6 and 7BD-33-11A is CD63. This is supported by studies showing that the monoclonal antibody RFAC4, reactive against CD63, identifies proteins that bound to 7BD-33-11A, H460-22-1 or 1A245.6 by immunoprecipitation. In addition, bacterial expression studies elucidated that H460-22-1, 1A245.6 and 7BD-33-11A bound to extracellular loop 2 of CD63. The 7BD-33-11A, H460-22-1 and 1A245.6 epitope was also distinguished by being conformation dependent. These IHC and biochemical results demonstrate that H460-22-1, 1A245.6 and 7BD-33-11A bind to the CD63 antigen. Thus, the preponderance of evidence shows that H460-22-1, 1A245.6 and 7BD-33-11A mediate anti-cancer effects through ligation of unique conformational epitope(s) present on CD63. For the purpose of this invention, said epitope is defined as a "CD63 antigenic moiety" characterized by its ability to bind with a monoclonal antibody encoded by the hybridoma cell line 7BD-33-11A, 1A245.6, H460-22-1, antigenic binding fragments thereof or antibody conjugates thereof.

In toto, this data demonstrates that the H460-22-1, 1A245.6 and 7BD-33-11A antigen is a cancer associated antigen and is expressed in humans, and is a pathologically relevant cancer target. Further, this data also demonstrates the binding of the H460-22-1, 1A245.6 and 7BD-33-11A antibody to human cancer tissues, and can be used appropriately for assays that can be diagnostic, predictive of therapy, or prognostic. In addition, the cell membrane localization of this antigen is indicative of the cancer status of the cell due to the relative infrequency of expression of the antigen in most non-malignant cells, and this observation permits the use of this antigen, its gene or derivatives, its protein or its variants to be used for assays that can be diagnostic, predictive of therapy, or prognostic.

The present invention describes the development and use of H460-22-1, 7BD-33-11A and 1A245.6, developed by the process described in U.S. Pat. No. 6,180,357 and identified by, its effect, in a cytotoxic assay, in non-established and established tumor growth in animal models and in prolonging survival time in those suffering from cancerous disease. In addition, the present invention discloses the development of two humanized versions of 7BD-33-11A, one of which displays similar cytotoxicity in a prophylatic animal model. The present invention also discloses the development and use of mouse monoclonal antibodies AR51A994.1, 7BDI-58 and 7BDI-60.

This invention represents an advance in the field of cancer treatment in that it describes reagents that bind specifically to an epitope or epitopes present on the target molecule, CD63, and that also have in vitro cytotoxic properties against malignant tumor cells but not normal cells, and which also directly mediate inhibition of tumor growth and extension of survival in in vivo models of human cancer. This is an advance in relation to any other previously described anti-CD63 antibody, since none have been shown to have similar properties. It also provides an advance in the field since it clearly demonstrates the direct involvement of CD63 in events associated with growth and development of certain types of tumors. It also represents an advance in cancer therapy since it has the potential to display similar anti-cancer properties in human patients. A further advance is that inclusion of these antibodies in a library of anti-cancer antibodies will enhance the possibility of targeting tumors expressing different antigen markers by determination of the appropriate combination of different anti-cancer antibodies, to find the most effective in targeting and inhibiting growth and development of the tumors.

In all, this invention teaches the use of the 7BD-33-11A antigen as a target for a therapeutic agent, that when administered can reduce the tumor burden of a cancer expressing the antigen in a mammal, and can also lead to a prolonged survival of the treated mammal.

Accordingly, it is an objective of the invention to utilize a method for producing cancerous disease modifying antibodies (CDMAB) raised against cancerous cells derived from a particular individual, or one or more particular cancer cell lines, which CDMAB are cytotoxic with respect to cancer cells while simultaneously being relatively non-toxic to non-cancerous cells, in order to isolate hybridoma cell lines and the corresponding isolated monoclonal antibodies and antigen binding fragments thereof for which said hybridoma cell lines are encoded.

It is an additional objective of the invention to teach cancerous disease modifying antibodies, ligands and antigen binding fragments thereof.

It is a further objective of the instant invention to produce cancerous disease modifying antibodies whose cytotoxicity is mediated through antibody dependent cellular toxicity.

It is yet an additional objective of the instant invention to produce cancerous disease modifying antibodies whose cytotoxicity is mediated through complement dependent cellular toxicity.

It is still a further objective of the instant invention to produce cancerous disease modifying antibodies whose cytotoxicity is a function of their ability to catalyze hydrolysis of cellular chemical bonds.

A still further objective of the instant invention is to produce cancerous disease modifying antibodies and ligands which are useful in a binding assay for diagnosis, prognosis, and monitoring of cancer.

Other objects and advantages of this invention will become apparent from the following description wherein are set forth, by way of illustration and example, certain embodiments of this invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2 is a comparison of AR51A994.1 versus positive and negative controls in a cytotoxicity assay.

FIG. 3 represents binding of AR51A994.1 and the anti-EGFR control to cancer and normal cell lines. The data is tabulated to present the mean fluorescence intensity as a fold increase above isotype control.

FIG. 5 is a comparison of 7BDI-58 and 7BDI-60 versus positive and negative controls in a cytotoxicity assay.

FIG. 6 represents binding of 7BDI-58, 7BDI-60 and the anti-Her2 control to cancer and normal cell lines. The data is tabulated to present the mean fluorescence intensity as a fold increase above isotype control.

FIG. 11. Immunocomplex prepared by immunoprecipitation with 7BD-33-11A from the total membrane fraction of the MDA-MB-231 cell line. Individual lanes of the blot were probed with 7BDI-58 (lane 1), AR51A994.1 (lane 2), 7BD-33-11A (lane 3) and with isotype control antibodies (lanes 4 and 5).

FIG. 14 is a summary of 7BD-33-11A binding on a human pancreatic tumor and normal tissue microarray.

FIG. 15. Representative micrographs showing the binding pattern on pancreatic tumor tissue obtained with 7BD-33-11A (A) or the isotype control antibody (B) and on non-neoplastic pancreatic tissue obtained with 7BD-33-11A (C) or the isotype control antibody (D) from a human tissue microarray. 7BD-33-11A displayed strong positive staining for the tumor cells and weak-moderate staining on the normal tissue. Magnification is 200x.

FIG. 16. In vitro cytotoxic activity, of mouse effector cells against human breast cancer cells, elicited by 7BD-33-11A. $^{51}$Cr-labelled MDA-MB-231 cells were incubated with non-adherent (a) and adherent (b) mouse splenic effector cells in the presence of varying concentrations of 7BD-33-11A or the isotype control.

FIG. 17. Summary of the number of macrophages from MDA-MB-231 xenografts after various dosing regiments with 7BD-33-11A or buffer control.

FIG. 18. Sequence of the N-terminal amino acids of 7BD-33-11A antibody.

FIG. 19. cDNA sequence for the light chain variable region of the 7BD-33-11A antibody (SEQ ID NO:1). The deduced amino acid sequence is shown below the nucleotide sequence (SEQ ID NO:2). The signal peptide sequence is in italics. The CDRs (Kabat nomenclature) are underlined. The mature light chain begins with an asparagine residue (bold and double underlined).

FIG. 20. cDNA sequence for the heavy chain variable region of the 7BD-33-11A antibody (SEQ ID NO:3). The deduced amino acid sequence is shown below the nucleotide sequence (SEQ ID NO:4). The signal peptide sequence is in italics. The CDRs (Kabat nomenclature) are underlined. The mature heavy chain begins with a glutamic acid residue (bold and double underlined).

FIG. 21. Alignment of the $V_L$ region amino acid sequences. The amino acid sequences of the $V_L$ regions of 7BD-33-11A (Mu33-11A) and (hu)AR7BD-33-11A (Hu33-11A), and the human acceptor 1LVE and JK2 are shown in single letter code. The CDR sequences (Kabat nomenclature) are underlined in the 7BD-33-11A $V_L$ sequence. The CDR sequences in the human VL segment are omitted in the Figure. The single underlined amino acid in the (hu)AR7BD-33-11A $V_L$ sequence is predicted to contact the CDR sequences, and therefore has been substituted with the corresponding mouse residue. The sequences disclosed, as read from the top, are amino acid residues 21-50 of SEQ ID NO:2; amino acid residues 22-52 of SEQ ID NO:6; SEQ ID NO:62; amino acid residues 51-80 of SEQ ID NO:2; amino acid residues 53-82 of SEQ ID NO:6; amino acid residues 63-77 of SEQ ID NO:6; amino acid residues 81-110 of SEQ ID NO:2; amino acid residues 83-112 of SEQ ID NO:6; amino acid residues 85-112 of SEQ ID NO:6; amino acid residues 111-132 of SEQ ID NO:2; amino acid residues 113-134 of SEQ ID NO:6; amino acid residues 113-116 of SEQ ID NO:6 and amino acid residues 125-134 of SEQ ID NO:6.

FIG. 22. Alignment of the $V_H$ region amino acid sequences. The amino acid sequences of the $V_H$ regions of 7BD-33-11A (Mu33-11A), (hu)AR7BD-33-11A (Hu33-11A), (hu)AR7BD-33-11A(V11L) and the human acceptor AAR32409 and JH6 are shown in single letter code. The CDR sequences (Kabat nomenclature) are underlined in the 7BD-33-11A $V_H$ sequence. The CDR sequences in the human $V_H$ segment are omitted in the Figure. The single underlined amino acids in the (hu)AR7BD-33-11A and (hu)AR7BD-33-11A(V11L) $V_H$ sequence are predicted to contact the CDR sequences, and therefore have been substituted with the corresponding mouse residues. The double underlined amino acids have been substituted with consensus human residues to reduce potential immunogenicity. The sequences disclosed, as read from the top, are amino acid residues 20-49 of SEQ ID NO:4; amino acid residues 20-49 of SEQ ID NO:8; amino acid residues 20-49 of SEQ ID NO:12; SEQ ID NO:63; amino acid residues 50-79 of SEQ ID NO:4; amino acid residues 50-79 of SEQ ID NO:8; amino acid residues 50-79 of SEQ ID NO:12; SEQ ID NO:64; amino acid residues 80-109 of SEQ ID NO:4; amino acid residues 80-109 of SEQ ID NO:8; amino acid residues 80-109 of SEQ ID NO:12; SEQ ID NO:65; amino acid residues 110-138 of SEQ ID NO:4; amino acid residues 110-138 of SEQ ID NO:8; amino acid residues 110-138 of SEQ ID NO: 12; SEQ ID NO:66 and amino acid resides 128-138 of SEQ ID NOS:8 and 12.

FIG. 23. Nucleotide sequence (SEQ ID NO:5) and deduced amino acid sequence (SEQ ID NO:6) of the light chain variable region of (hu)AR7BD-33-11A in the mini exon. The signal peptide sequence is in italics. The CDRs (Kabat nomenclature) are underlined. The mature light chain begins with an aspartic acid residue (bold and double-underlined). The sequence is flanked by unique MluI (ACGCGT) and XbaI (TCTAGA) sites.

FIG. 24. Nucleotide sequence (SEQ ID NO:7) and deduced amino acid sequence (SEQ ID NO:8) of the heavy chain variable region of (hu)AR7BD-33-11A(V11L) in the mini exon. The signal peptide sequence is in italics. The CDRs (Kabat nomenclature) are underlined. The mature heavy chain begins with a glutamic acid residue (bold and double-underlined). The sequence shown is flanked by unique MluI (ACGCGT) and XbaI (TCTAGA) sites.

FIG. 25. Primers used for the construction of the 7BD-33-11A $V_L$ gene. The sequences disclosed, as read from the top, are SEQ ID NOS:21-39.

FIG. 26. Primers used for the construction of the 7BD-33-11A $V_H$ gene. The sequences disclosed, as read from the top, are SEQ ID NOS:40-61.

FIG. 28. Summary of FACS competition experiments.

FIG. 31. (hu)AR7BD-33-11A kappa light chain cDNA (SEQ ID NO:9) and translated amino acid sequence (SEQ ID NO: 10). The amino acids are shown in single letter code; the dot (•) indicates the translation termination codon. The first amino acid of the mature light chain is double-underlined and bold, preceded by its signal peptide sequence.

FIG. 32. (hu)AR7BD-33-11A(V11L)γ1 heavy chain cDNA (SEQ ID NO:11) and translated amino acid sequence (SEQ ID NO:12). The amino acids are shown in single letter code; the dot (•) indicates the translation termination codon. The first amino acid of the mature heavy chain is double-underlined and bold, preceded by its signal peptide sequence.

FIG. 33. (hu)AR7BD-33-11A(V11L)γ2M3 heavy chain cDNA (SEQ ID NO:13) and translated amino acid sequence (SEQ ID NO:14). The amino acids are shown in single letter code; the dot (•) indicates the translation termination codon. The first amino acid of the mature heavy chain is double-underlined and bold, preceded by its signal peptide sequence.

FIG. 36. Summary of FACS competition experiments.

FIG. 40. Binding affinity of the anti-CD637BD-33-11A, H460-22-1, 1A245.6, and of the humanized antibodies (hu) AR7BD-33-11A-IgG1 and (hu)AR7BD-33-11A-IgG2M3. Dissociation constants for the binding of the antibodies to the purified recombinant GST fusion construct protein GST-EC2 (CD63) was assessed by surface plasmon resonance.

DETAILED DESCRIPTION OF THE INVENTION

Figure 4:
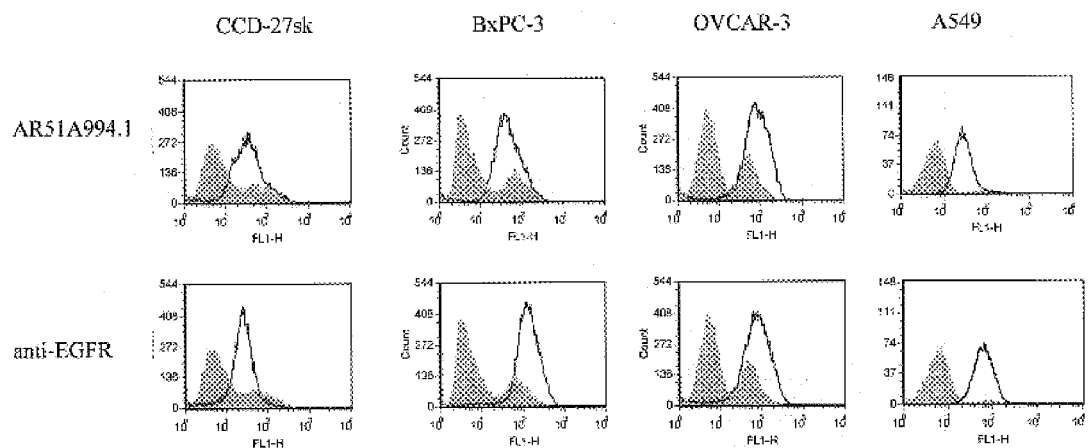
FIG. 4 includes representative FACS histograms of AR51A994.1 and anti-EGFR antibodies directed against several cancer and non-cancer cell lines.

In general, the following words or phrases have the indicated definition when used in the summary, description, examples, and claims.

The term "antibody" is used in the broadest sense and specifically covers, for example, single monoclonal antibodies (including agonist, antagonist, and neutralizing antibodies, de-immunized, murine, chimerized or humanized antibodies), antibody compositions with polyepitopic specificity, single chain antibodies, immunoconjugates and fragments of antibodies (see below).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma (murine or human) method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352:624-628 (1991) and Marks et al., J Mol. Biol., 222:581-597 (1991), for example.

"Antibody fragments" comprise a portion of an intact antibody, preferably comprising the antigen-binding or variable region thereof. Examples of antibody fragments include less than full length antibodies, Fab, Fab', $F(ab')_2$, and Fv fragments; diabodies; linear antibodies; single-chain antibody molecules; single-chain antibodies, single domain antibody molecules, fusion proteins, recombinant proteins and multi-specific antibodies formed from antibody fragment(s).

An "intact" antibody is one which comprises an antigen-binding variable region as well as a light chain constant domain $(C_L)$ and heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

Depending on the amino acid sequence of the constant domain of their heavy chains, intact antibodies can be assigned to different "classes". There are five-major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called a, d, e, ?, and μ, respectively. The subunit structures and three-dimensional configurations of different classes of immunoglobulins are well known.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc.

"Antibody-dependent cell-mediated cytotoxicity" and "ADCC" refer to a cell-mediated reaction in which nonspecific cytotoxic cells that express Fc receptors (FcRs)(e.g. Natural Killer (NK) cells, neutrophils, and macrophages) recognize bound antibody on a target cell and subsequently cause lysis of the target cell. The primary cells for mediating ADCC, NK cells, express Fc?RIII only, whereas monocytes express Fc?RI, Fc?RII and Fc?RIII. FcR expression on hematopoietic cells in summarized is Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998).

"Effector cells" are leukocytes which express one or more FcRs and perform effector functions. Preferably, the cells express at least Fc?RIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the Fc?RI, Fc?RII, and Fc? RIII subclasses, including allelic variants and alternatively spliced forms of these receptors. Fc?RII receptors include Fc?RIIA (an "activating receptor") and Fc?RIIB (an "inhibiting receptor"), which have similar amino acid sequences that differ primarily in the cytoplasmic domains thereof. Activating receptor Fc?RIIA contains an immunoreceptor tyrosine-based activation motif (ITAM) in its cytoplasmic domain. Inhibiting receptor Fc?RIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, Annu. Rev. Immunol 9:457-92 (1991); Capel et al., *Immunomethods* 4:25-34 (1994); and de Haas et al., *J Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J Immunol.* 117:587 (1976) and Kim et al., *Eur. J. Immunol.* 24:2429 (1994)).

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the >sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of proteins of Immunological Interest*, 5th Ed. Public Health Service, National Institutes of Health, Bethesda, Md. (1991)) and/or those residues from a "hypervariable loop" (e.g. residues 2632 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site. The Fab fragment also contains the constant domain of the light chain and the first constant domain (CH I) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (?) and lambda (?), based on the amino acid sequences of their constant domains.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies*, vol. 113, Rosenburg and Moore eds., Springer-Verlag, N.Y., pp. 269-315 (1994).

The term "diabodies" refers to small antibody fragments with two antigen-binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA,* 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other protcinaceous or nonproteinaceous solutes. Isolated antibody includes the antibody in situ within recombinant cells since at least one component of the antibody's natural environment will not be present. Ordinarily, however, isolated antibody will be prepared by at least one purification step.

An antibody "which binds" an antigen of interest, e.g. CD63 antigenic moiety, is one capable of binding that antigen with sufficient affinity such that the antibody is useful as a therapeutic or diagnostic agent in targeting a cell expressing the antigen. Where the antibody is one which binds CD63 antigenic moiety it will usually preferentially bind CD63 antigenic moiety as opposed to other receptors, and does not include incidental binding such as non-specific Fc contact, or binding to post-translational modifications common to other antigens and may be one which does not significantly cross-react with other proteins. Methods, for the detection of an antibody that binds an antigen of interest, are well known in the art and can include but are not limited to assays such as FACS, cell ELISA and Western blot.

As used herein, the expressions "cell", "cell line", and "cell culture" are used interchangeably, and all such designations include progeny. It is also understood that all progeny may not be precisely identical in DNA content, due to deliberate or inadvertent mutations. Mutant progeny that have the same function or biological activity as screened for in the originally transformed cell are included. It will be clear from the context where distinct designations are intended.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. Hence, the mammal to be treated herein may have been diagnosed as having the disorder or may be predisposed or susceptible to the disorder.

The terms "cancer" and "cancerous" refer to or describe the physiological condition in mammals that is typically characterized by unregulated cell growth or death. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, camomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2?-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®, Aventis, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

"Mammal" for purposes of treatment refers to any animal classified as a mammal, including humans, mice, SCID or nude mice or strains of mice, domestic and farm animals, and zoo, sports, or pet animals, such as sheep, dogs, horses, cats, cows, etc. Preferably, the mammal herein is human.

"Oligonucleotides" are short-length, single-or double-stranded polydeoxynucleotides that are chemically synthesized by known methods (such as phosphotriester, phosphite, or phosphoramidite chemistry, using solid phase techniques such as described in EP 266,032, published 4 May 1988, or via deoxynucleoside H-phosphonate intermediates as described by Froehler et al., *Nucl. Acids Res.,* 14:5399-5407, 1986. They are then purified on polyacrylamide gels.

Unless indicated otherwise, the term "CD63 antigenic moiety" when used herein refers to the Type III membrane protein of the tetraspanin family also referred to as melanoma 1 antigen, ocular melanoma-associated antigen, melanoma associated antigen ME491, lysosome-associated membrane glycoprotein 3, granulophysin, melanoma-associated antigen MLA1.

"Chimeric" antibodies are immunoglobulins in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567 and Morrison et al, Proc. Natl. Acad. Sci. USA, 81:6851-6855 (1984)).

"Humanized" forms of non-human (e.g. murine) antibodies are specific chimeric immunoglobulins, immunoglobulin chains or fragments thereof (such as Fv, Fab, Fab', F(ab)$_2$ or other antigen-binding subsequences of antibodies) which contain minimal sequence derived from non-human immunoglobulin. For the most part, humanized antibodies are human immunoglobulins (recipient antibody) in which residues from the complementarity determining regions (CDRs) of the recipient antibody are replaced by residues from the CDRs of a non-human species (donor antibody) such as mouse, rat or rabbit having the desired specificity, affinity and capacity. In some instances, Fv framework region (FR) residues of the human immunoglobulin are replaced by corresponding non-human FR residues. Furthermore, the humanized antibody may comprise residues which are found neither in the recipient antibody nor in the imported CDR or FR sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR residues are those of a human immunoglobulin consensus sequence. The humanized antibody optimally also will comprise at least a portion of an immunoglobulin constant region (Fc), typically that of a human immunoglobulin.

"De-immunized" antibodies are immunoglobulins that are non-immunogenic, or less immunogenic, to a given species. De-immunization can be achieved through structural alterations to the antibody. Any de-immunization technique known to those skilled in the art can be employed. One suitable technique for de-immunizing antibodies is described, for example, in WO 00/34317 published Jun. 15, 2000.

"Homology" is defined as the percentage of residues in the amino acid sequence variant that are identical after aligning the sequences and introducing gaps, if necessary, to achieve the maximum percent homology. Methods and computer programs for the alignment are well known in the art.

Throughout the instant specification, hybridoma cell lines, as well as the isolated monoclonal antibodies which are produced therefrom, are alternatively referred to by their internal designation, 7BDI-58, 7BDI-60, 7BD-33-11A, 1A245.6, H460-22-1, or AR51A994.1 or Depository Designation, IDAC 141205-01, ATCC PTA-4623, ATCC PTA-4890, ATCC PTA-4889, ATCC PTA-4622, or IDAC 141205-06.

As used herein "ligand" includes a moiety which exhibits binding specificity for a target antigen, and which may be an intact antibody molecule and any molecule having at least an antigen-binding region or portion thereof (i.e., the variable portion of an antibody molecule), e.g., an Fv molecule, Fab molecule, Fab' molecule, F(ab').sub.2 molecule, a bispecific antibody, a fusion protein, or any genetically engineered molecule which specifically recognizes and binds the antigen bound by the isolated monoclonal antibody produced by the hybridoma cell line designated as, IDAC 141205-01, ATCC PTA-4623, ATCC PTA-4890, ATCC PTA-4889, ATCC PTA-4622, or IDAC 141205-06 (the IDAC 141205-01, ATCC PTA-4623, ATCC PTA-4890, ATCC PTA-4889, ATCC PTA-4622, or IDAC 141205-06 antigen).

As used herein "antigen-binding region" means a portion of the molecule which recognizes the target antigen.

As used herein "competitively inhibits" means being able to recognize and bind a determinant site to which the monoclonal antibody produced by the hybridoma cell line designated as IDAC 141205-01, ATCC PTA-4623, ATCC PTA-4890, ATCC PTA-4889, ATCC PTA-4622, or IDAC 141205-06, (the IDAC 141205-01, ATCC PTA-4623, ATCC PTA-4890, ATCC PTA-4889, ATCC PTA-4622, or IDAC 141205-06 antibody) is directed using conventional reciprocal antibody competition assays. (Belanger L., Sylvestre C. and Dufour D. (1973), Enzyme linked immunoassay for alpha fetoprotein by competitive and sandwich procedures. Clinica Chimica Acta 48, 15).

As used herein "target antigen" is the IDAC 141205-01, ATCC PTA-4623, ATCC PTA-4890, ATCC PTA-4889, ATCC PTA-4622, or IDAC 141205-06 antigen or portions thereof.

As used herein, an "immunoconjugate" means any molecule or ligand such as an antibody chemically or biologically linked to a cytotoxin, a radioactive agent, enzyme, toxin, an anti-tumor drug or a therapeutic agent. The antibody may be linked to the cytotoxin, radioactive agent, anti-tumor drug or therapeutic agent at any location along the molecule so long as it is able to bind its target. Examples of immunoconjugates include antibody toxin chemical conjugates and antibody-toxin fusion proteins.

As used herein, a "fusion protein" means any chimeric protein wherein an antigen binding region is connected to a biologically active molecule, e.g., toxin, enzyme, or protein drug.

In order that the invention herein described may be more fully understood, the following description is set forth.

The present invention provides ligands (i.e., IDAC 141205-01, ATCC PTA-4623, ATCC PTA-4890, ATCC PTA-4889, ATCC PTA-4622, or IDAC 141205-06 ligands) which specifically recognize and bind the IDAC 141205-01, ATCC PTA-4623, ATCC PTA-4890, ATCC PTA-4889, ATCC PTA-4622, or IDAC 141205-06 antigen.

The ligand of the invention may be in any form as long as it has an antigen-binding region which competitively inhibits the immunospecific binding of the monoclonal antibody produced by hybridoma IDAC 141205-01, ATCC PTA-4623, ATCC PTA-4890, ATCC PTA-4889, ATCC PTA-4622, or IDAC 141205-06 to its target antigen. Thus, any recombinant proteins (e.g., fusion proteins wherein the antibody is combined with a second protein such as a lymphokine or a tumor inhibitory growth factor) having the same binding specificity as the IDAC 141205-01, ATCC PTA-4623, ATCC PTA-4890, ATCC PTA-4889, ATCC PTA-4622, or IDAC 141205-06 antibody fall within the scope of this invention.

In one embodiment of the invention, the ligand is the IDAC 141205-01, ATCC PTA-4623, ATCC PTA-4890, ATCC PTA-4889, ATCC PTA-4622, or IDAC 141205-06 antibody.

In other embodiments, the ligand is an antigen binding fragment which may be a Fv molecule (such as a single chain Fv molecule), a Fab molecule, a Fab' molecule, a F(ab')2 molecule, a fusion protein, a bispecific antibody, a heteroantibody or any recombinant molecule having the antigen-binding region of the IDAC 141205-01, ATCC PTA-4623, ATCC PTA-4890, ATCC PTA-4889, ATCC PTA-4622, or IDAC 141205-06 antibody. The ligand of the invention is directed to the epitope to which the IDAC 141205-01, ATCC PTA-4623, ATCC PTA-4890, ATCC PTA-4889, ATCC PTA-4622, or IDAC 141205-06 monoclonal antibody is directed.

The ligand of the invention may be modified, i.e., by amino acid modifications within the molecule, so as to produce derivative molecules. Chemical modification may also be possible.

Derivative molecules would retain the functional property of the polypeptide, namely, the molecule having such substitutions will still permit the binding of the polypeptide to the IDAC 141205-01, ATCC PTA-4623, ATCC PTA-4890, ATCC PTA-4889, ATCC PTA-4622, or IDAC 141205-06 antigen or portions thereof.

These amino acid substitutions include, but are not necessarily limited to, amino acid substitutions known in the art as "conservative".

For example, it is a well-established principle of protein chemistry that certain amino acid substitutions, entitled "conservative amino acid substitutions," can frequently be made in a protein without altering either the conformation or the function of the protein.

Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

Given an antibody, an individual ordinarily skilled in the art can generate a competitively inhibiting ligand, for example a competing antibody, which is one that recognizes the same epitope (Belanger et al., 1973). One method could entail immunizing with an immunogen that expresses the antigen recognized by the antibody. The sample may include but is not limited to tissue, isolated protein(s) or cell line(s). Resulting hybridomas could be screened using a competing assay, which is one that identifies antibodies that inhibit the binding of the test antibody, such as ELISA, FACS or immunoprecipitation. Another method could make use of phage display libraries and panning for antibodies that recognize said antigen (Rubinstein et al., 2003). In either case, hybridomas would be selected based on their ability to out-compete the binding of the original antibody to its target antigen. Such hybridomas would therefore possess the characteristic of recognizing the same antigen as the original antibody and more specifically would recognize the same epitope.

EXAMPLE 1

Hybridoma Production—Hybridoma Cell Line AR51A994.1 and 7BDI-58

The hybridoma cell lines 7BDI-58 and AR51A994.1 were deposited, in accordance with the Budapest Treaty, with the International Depository Authority of Canada (IDAC), Bureau of Microbiology, Health Canada, 1015 Arlington Street, Winnipeg, Manitoba, Canada, R3E 3R2, on Dec. 14, 2005, under Accession Numbers 141205-01 and 141205-06 respectively. In accordance with 37 CFR 1.808, the depositors assure that all restrictions imposed on the availability to the public of the deposited materials will be irrevocably removed upon the granting of a patent.

The hybridoma that produces the anti-cancer antibody 7BDI-58 was produced as disclosed in Ser. No. 10/713,642. To produce the hybridoma that produces the anti-cancer antibody AR51A994.1, a single cell suspension of frozen human ovarian endometroid adenocarcinoma tumor tissue (Genomics Collaborative, Cambridge, Mass.) was prepared in PBS. IMMUNEASY™ (Qiagen, Venlo, Netherlands) adjuvant was prepared for use by gentle mixing. Four to six week old BALB/c mice were immunized by injecting subcutaneously, 2 million cells in 50 microliters of the antigen-adjuvant. Recently prepared antigen-adjuvant was used to boost the immunized mice intraperitoneally, 2 and 5 weeks after the initial immunization, with approximately 2 million cells in 50-60 microliters. A spleen was used for fusion three days after the last immunization. The hybridomas were prepared by fusing the isolated splenocytes with NSO-1 myeloma partners. The supernatants from the fusions were tested from subclones of the hybridomas.

Figure 1I:
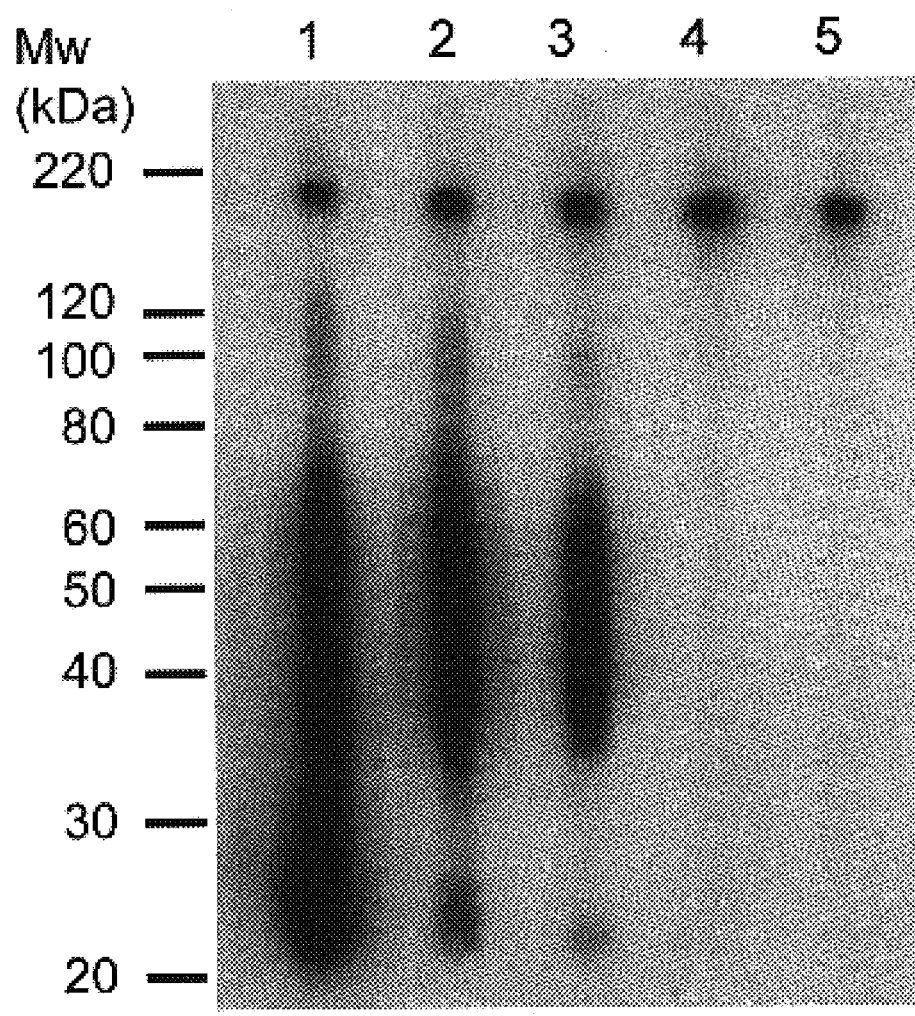
FIG. 1 compares the percentage cytotoxicity and binding levels of the hybridoma supernatants against cell lines OCC-1, OVAR-3 and CCD-27sk.

To determine whether the antibodies secreted by the hybridoma cells are of the IgG or IgM isotype, an ELISA assay was employed. 100 microliters/well of goat anti-mouse IgG+IgM (H+L) at a concentration of 2.4 micrograms/mL in coating buffer (0.1 M carbonate/bicarbonate buffer, pH 9.2-9.6) at 4° C. was added to the ELISA plates overnight. The plates were washed thrice in washing buffer (PBS+0.05% Tween). 100 microliters/well blocking buffer (5% milk in wash buffer) was added to the plate for 1 hour at room temperature and then washed thrice in washing buffer. 100 microliters/well of hybridoma supernatant was added and the plate incubated for 1 hour at room temperature. The plates were washed thrice with washing buffer and 1/100,000 dilution of either goat anti-mouse IgG or IgM horseradish peroxidase conjugate (diluted in PBS containing 5% milk), 100 microliters/well, was added. After incubating the plate for 1 hour. at room temperature the plate was washed thrice with washing buffer. 100 microliters/well of TMB solution was incubated for 1-3 minutes at room temperature. The color reaction was terminated by adding 50 microliters/well 2M $H_2SO_4$ and the plate was read at 450 nm with a Perkin-Elmer HTS7000 plate reader. As indicated in FIG. 1, the AR51A994.1 hybridoma secreted primarily antibodies of the IgG isotype.

To determine the subclass of antibody secreted by the hybridoma cells, an isotyping experiment was performed using a Mouse Monoclonal Antibody Isotyping Kit (HyCult Biotechnology, Frontstraat, Netherlands). 500 microliters of buffer solution was added to the test strip containing rat anti-mouse subclass specific antibodies. 500 microliters of hybridoma supernatant was added to the test tube, and submerged by gentle agitation. Captured mouse immunoglobulins were detected directly by a second rat monoclonal antibody which is coupled to colloid particles. The combination of these two proteins creates a visual signal used to analyse the isotype. The anti-cancer antibody AR51A994.1 is of the IgG1, kappa isotype.

After one round of limiting dilution, hybridoma supernatants were tested for antibodies that bound to target cells in a cell ELISA assay. Two human ovarian cancer cell lines, and 1 human normal skin cell line were tested: OCC-1, OVCAR-3 and CCD-27sk respectively. The plated cells were fixed prior to use. The plates were washed thrice with PBS containing $MgCl_2$ and $CaCl_2$ at room temperature. 100 microliters of 2% paraformaldehyde diluted in PBS was added to each well for 10 minutes at room temperature and then discarded. The plates were again washed with PBS containing $MgCl_2$ and $CaCl_2$ three times at room temperature. Blocking was done with 100 microliters/well of 5% milk in wash buffer (PBS+ 0.05% Tween) for 1 hour at room temperature. The plates were washed thrice with wash buffer and the hybridoma supernatant was added at 75 microliters/well for 1 hour at room temperature. The plates were washed 3 times with wash buffer and 100 microliters/well of 1/25,000 dilution of goat anti-mouse IgG antibody conjugated to horseradish peroxidase (diluted in PBS containing 5% milk) was added. After 1 hour incubation at room temperature the plates were washed 3 times with wash buffer and 100 microliters/well of TMB substrate was incubated for 1-3 minutes at room temperature. The reaction was terminated with 50 microliters/well 2M $H_2SO_4$ and the plate read at 450 nm with a Perkin-Elmer HTS7000 plate reader. The results as tabulated in FIG. 1 were expressed as the number of folds above background compared to an in-house IgG isotype control that has previously been shown not to bind to the cell lines tested. The antibodies from the hybridoma AR51A994.1 showed binding to the ovarian cancer cell line OVCAR-3 and to the normal skin cell line CCD-27sk.

In conjunction with testing for antibody binding, the cytotoxic effect of the hybridoma supernatants was tested in the cell lines: OCC-1, OVCAR-3 and CCD-27sk. Calcein AM was obtained from Molecular Probes (Eugene, Oreg.). The assays were performed according to the manufacturer's instructions with the changes outlined below. Cells were plated before the assay at the predetermined appropriate density. After 2 days, 75 microliters of supernatant from the hybridoma microtitre plates were transferred to the cell plates and incubated in a 5 percent $CO_2$ incubator for 5 days. The wells that served as the positive controls were aspirated until empty and 100 microliters of sodium azide ($NaN_3$) or cycloheximide was added. After 5 days of treatment, the plates were then emptied by inverting and blotting dry. Room temperature DPBS (Dulbecco's phosphate buffered saline) containing $MgCl_2$ and $CaCl_2$ was dispensed into each well from a multichannel squeeze bottle, tapped 3 times, emptied by inversion and then blotted dry. 50 microliters of the fluorescent calcein dye diluted in DPBS containing $MgCl_2$ and $CaCl_2$ was added to each well and incubated at 37° C. in a 5% $CO_2$ incubator for 30 minutes. The plates were read in a Perkin-Elmer HTS7000 fluorescence plate reader and the data was analyzed in Microsoft Excel. The results are tabulated in FIG. 1. Supernatant from the AR51A994.1 hybridoma produced specific cytotoxicity of 14 percent and 10 percent on the OCC-1 and OVCAR-3 cells respectively. On OCC-1, this was 16 and 15 percent of the cytotoxicity obtained with the positive controls sodium azide and cycloheximide, respectively. On OVCAR-3, this was 22 percent of the cytotoxicity obtained with the positive control cycloheximide. Results from FIG. 1 demonstrated that the cytotoxic effects of AR51A994.1 were not proportional to the binding levels on the cancer cell types. There was a greater level of cytotoxicity produced in the OCC-1 cells as compared to the OVCAR-3 cells, although the level of binding in the OVCAR-3 cells was higher. As tabulated in FIG. 1, AR51A994.1 did not produce cytotoxicity in the CCD-27sk normal cell line. The known non-specific cytotoxic agents cycloheximide and $NaN_3$ generally produced cytotoxicity as expected.

EXAMPLE 2

Antibody Production:

The AR51A994.1, 7BDI-58 and 7BDI-60 monoclonal antibodies were produced by culturing the hybridomas in CL-1000 flasks (BD Biosciences, Oakville, ON) with collections and reseeding occurring twice/week. The antibody was purified according to standard antibody purification procedures with Protein G Sepharose 4 Fast Flow (Amersham Biosciences, Baie d'Urfé, QC). It is within the scope of this invention to utilize monoclonal antibodies that are de-immunized, humanized, chimerized or murine.

The AR51A994.1 antibody was compared to a number of both positive (anti-EGFR (C225, IgG1, kappa, 5 microgram/mL, Cedarlane, Hornby, ON), Cycloheximide (100 micromolar, Sigma, Oakville, ON), $NaN_3$ (0.1%, Sigma, Oakville, ON)) and negative (107.3 (anti-TNP, IgG1, kappa, 20 micrograms/mL, BD Biosciences, Oakville, ON), and 1B7.11 (anti-TNP), IgG1, kappa, 20 micrograms/mL purified in-house)), as well as a buffer diluent control in a cytotoxicity assay (FIG. 2). Pancreatic cancer (BxPC-3), ovarian cancer (OCC-1 and OVCAR-3) and non-cancer (CCD-27sk, Hs888.Lu) cell lines were tested (all from the ATCC, Manassas, Va.). Calcein AM was obtained from Molecular Probes (Eugene,OR). The assays were performed according to the manufacturer's instructions with the changes outlined below. Cells were plated before the assay at the predetermined appropriate density. After 2 days, 100 microliters of purified antibody or controls were diluted into media, and then transferred to the cell plates and incubated in a 5 percent $CO_2$ incubator for 5 days. The plates were then emptied by inverting and blotted dry. Room temperature DPBS containing $MgCl_2$ and $CaCl_2$ was dispensed into each well from a multichannel squeeze bottle, tapped 3 times, emptied by inversion and then blotted dry. 50 μL of the fluorescent calcein dye diluted in DPBS containing $MgCl_2$ and $CaCl_2$ was added to each well and incubated at 37° C. in a 5 percent $CO_2$ incubator for 30 minutes. The plates were read in a Perkin-Elmer HTS7000 fluorescence plate reader and the data was analyzed in Microsoft Excel and the results were tabulated in FIG. 2. Each antibody received a score between 5 and 50 based on the average cytotoxicity observed in four experiments tested in triplicate, and a score between 25 and 100 based on the variability observed between assays. The sum of these two scores (the cytotoxicity score) is presented in FIG. 2. A cytotoxicity score of greater than or equal to 55 was considered to be positive on the cell line tested. The AR51A994.1 antibody produced specific cytotoxicity in the OVCAR-3 ovarian cancer cell line and the BxPC-3 pancreatic cancer cell line relative to both isotype and buffer negative controls. This is consistent with data from the hybridoma supernatant of the AR51A994.1 clone, which also showed specific cytotoxicity against the OVCAR-3 cell line (see Example 1). AR51A994.1 did not produce positive cytotoxicity scores in the OCC-1 ovarian cancer cell line. Importantly, AR51A994.1 did not produce significant cytotoxicity, compared to negative controls, against non-cancer cell lines such as CCD-27sk or Hs888.Lu, suggesting that the antibody is specifically cytotoxic towards cancer cells. The chemical cytotoxic agents induced their expected cytotoxicity against multiple cell lines.

Binding of AR51A994.1 to pancreatic cancer (BxPC-3), ovarian cancer (OCC-1 and OVCAR-3) and non-cancer (CCD-27sk, Hs888.Lu) cell lines was assessed by flow cytometry (FACS). Cells were prepared for FACS by initially washing the cell monolayer with DPBS (without $Ca^{++}$ and Mg$^{++}$). Cell dissociation buffer (INVITROGEN, Burlington, ON) was then used to dislodge the cells from their cell culture plates at 37° C. After centrifugation and collection, the cells were resuspended in DPBS containing MgCl$_2$, CaCl$_2$ and 2 percent fetal bovine serum at 4° C. (staining media) and counted, aliquoted to appropriate cell density, spun down to pellet the cells and resuspended in staining media at 4° C. in the presence of test antibodies (AR51A994.1) or control antibodies (isotype control, anti-EGFR) at 20 µg/mL on ice for 30 minutes. Prior to the addition of Alexa Fluor 546-conjugated secondary antibody the cells were washed once with staining media. The Alexa Fluor 546-conjugated antibody in staining media was then added for 30 minutes at 4° C. The cells were then washed for the final time and resuspended in fixing media (staining media containing 1.5% paraformaldehyde). Flow cytometric acquisition of the cells was assessed by running samples on a FACSarray™ using the FACSarray™ System Software (BD Biosciences, Oakville, ON). The forward (FSC) and side scatter (SSC) of the cells were set by adjusting the voltage and amplitude gains on the FSC and SSC detectors. The detectors for the fluorescence (Alexa-546) channel was adjusted by running unstained cells such that cells had a uniform peak with a median fluorescent intensity of approximately 1-5 units. For each sample, approximately 10,000 gated events (stained fixed cells) were acquired for analysis and the results are presented in FIG. 3.

FIG. 3 presents the mean fluorescence intensity fold increase above isotype control. Representative histograms of AR51A994.1 antibodies were compiled for FIG. 4. AR51A994.1 showed strong binding to the ovarian cancer cell lines OCC-1 and OVCAR-3 (16 and 14.8 fold respectively) and the non-cancer lung cell line Hs888.Lu (24.6 fold) with weaker binding to the pancreatic cancer cell line BxPC-3 (8.6 fold) and the non-cancer skin cell line CCD-27sk (5.1 fold). These data demonstrate that AR51A994.1 exhibited functional specificity in that although there was clear binding to a number of cell lines tested, there was only associated cytotoxicity with OVCAR-3 ovarian and BxPC-3 pancreatic cancer in vitro.

To further the in vitro binding and cytotoxicity results from above, the AR51A994.1 antibody was tested with lung cancer (A549), additional pancreatic cancer (AsPC-1 and PL45) and ovarian cancer (C-13, ES-2, Hey, OV2008, OVCA-429 and OVCAR-3) cell lines (A549, AsPC-1, PL45 and OVCAR-3 were from ATCC, Manassas, Va. C-13, ES-2, Hey, OV2008 and OVCA-429 were obtained from the Ottawa Regional Cancer Center (Ottawa, Ontario)) along with the positive and negative controls as mentioned above, in a cytotoxicity assay. The Live/Dead cytotoxicity assay was performed as described above. The AR51A994.1 antibody produced specific cytotoxicity in the ES-2, OV2008 and OVCA-429 ovarian cancer cell lines and the A549 lung cancer cell line relative to both isotype and buffer negative controls (FIG. 2). Also, the AR51A994.1 antibody produced specific cytotoxicity in the OVCAR-3 ovarian cancer cell line. This is consistent with the OVCAR-3 cytotoxicity data from above. AR51A994.1 did not produce positive cytotoxicity scores in the C-13 and Hey ovarian cancer cell lines or the AsPC-1 and PL45 pancreatic cell lines. The chemical cytotoxic agents induced their expected cytotoxicity against multiple cell lines.

Binding of AR51A994.1 to lung cancer (A549), additional pancreatic cancer (AsPC-1 and PL45) and ovarian cancer (C-13, ES-2, Hey, OV2008, OVCA-429 and OVCAR-3) cell lines was assessed by flow cytometry (FACS) as outlined above. FIG. 3 presents the mean fluorescence intensity fold increase above isotype control. Representative histograms of AR51A994.1 antibodies were compiled for FIG. 4. AR51A994.1 showed greater binding to the ovarian cancer cell lines ES-2 and OV2008 (22.2 and 19.8 fold respectively) and weaker binding to the ovarian cancer cell lines C-13, Hey, OVCA-429 and OVCAR-3 (9.8, 4.4, 3.9 and 4.3 fold respectively), the pancreatic cell lines AsPC-1 and PL45 (4.1 and 2.4 fold respectively) and the lung cancer cell line A549 (4.6 fold). These data demonstrate that AR51A994.1 exhibited functional specificity in that although there was clear binding to all cell lines tested, there was only associated cytotoxicity with some of the cancer cell lines.

The 7BDI-58 and 7BDI-60 antibody was compared to a number of both positive (anti-Her2 (IgG1, kappa, 10 micrograms/mL, Inter Medico, Markham, ON), Cycloheximide (100 micromolar, Sigma, Oakville, ON)) and negative (107.3 (anti-TNP, IgG1, kappa, 20 micrograms/mL, BD Biosciences, Oakville, ON)), as well as a buffer diluent control in a cytotoxicity assay (FIG. 5). Ovarian cancer (OVCAR-3) and breast cancer (MDA-MB-468 (MB-468)) and non-cancer (Bst549, CCD-27sk, Hs888.Lu) cell lines were tested (all from the ATCC, Manassas, Va.). The Live/Dead cytotoxicity assay was obtained from Molecular Probes (Eugene, Oreg.). The assays were performed according to the manufacturer's instructions with the changes outlined below. Cells were plated before the assay at the predetermined appropriate density. After 2 days, 100 microliters of purified antibody or controls were diluted into media, and then transferred to the cell plates and incubated in a 5 percent CO$_2$ incubator for 5 days. The plates were then emptied by inverting and blotted dry. Room temperature DPBS containing MgCl$_2$ and CaCl$_2$ was dispensed into each well from a multichannel squeeze bottle, tapped 3 times, emptied by inversion and then blotted dry. 50 microliters of the fluorescent calcein dye diluted in DPBS containing MgCl$_2$ and CaCl$_2$ was added to each well and incubated at 37° C. in a 5 percent CO$_2$ incubator for 30 minutes. The plates were read in a Perkin-Elmer HTS7000 fluorescence plate reader and the data was analyzed in Microsoft Excel and the results were tabulated in FIG. 5. Each antibody received a score between 5 and 50 based on the average cytotoxicity observed in four experiments tested in triplicate, and a score between 25 and 100 based on the variability observed between assays. The sum of these two scores (the cytotoxicity score) is presented in FIG. 5. A cytotoxicity score of greater than or equal to 55 was considered to be positive on the cell line tested. The 7BDI-58 antibody produced specific cytotoxicity in the OVCAR-3 ovarian cancer cell line relative to both isotype and buffer negative controls. 7BDI-58 did not produce positive cytotoxicity scores in the MB-468 breast cancer cell line. Importantly, 7BDI-58 did not produce significant cytotoxicity, compared to negative controls, against non-cancer cell lines such as Bst549, CCD-27sk or Hs888.Lu, suggesting that the antibody has specific cytotoxicity for cancer cells. The 7BDI-60 antibody produced specific cytotoxicity in the MB-468 breast cancer cell line relative to both isotype and buffer negative controls. 7BDI-60 did not produce positive cytotoxicity scores in the OVCAR-3 ovarian cancer cell line. Importantly, 7BDI-60 did not produce significant cytotoxicity, compared to negative controls, against non-cancer cell lines such as Bst549, CCD-27sk or Hs888.Lu, suggesting that the antibody has specific cytotoxicity for cancer cells. The chemical cytotoxic agent induced its expected cytotoxicity against multiple cell lines.

Binding of 7BDI-58 and 7BDI-60 to breast cancer (MB-468), ovarian cancer (OVCAR-3) and non-cancer (Bst549, CCD-27sk, Hs888.Lu) cell lines was assessed by flow cytometry (FACS). Cells were prepared for FACS by initially washing the cell monolayer with DPBS (without Ca$^{++}$ and Mg$^{++}$).

Cell dissociation buffer (INVITROGEN, Burlington, ON) was then used to dislodge the cells from their cell culture plates at 37° C. After centrifugation and collection the cells were resuspended in Dulbecco's phosphate buffered saline containing $MgCl_2$, $CaCl_2$ and 25% fetal bovine serum at 4° C. (wash media) and counted, aliquoted to appropriate cell density, spun down to pellet the cells and resuspended in staining media (DPBS containing $MgCl_2$ and $CaCl_2$) containing test antibodies (7BDI-58 or 7BDI-60) or control antibodies (isotype control or anti-EGFR) at 20 micrograms/mL on ice for 30 minutes. Prior to the addition of Alexa Fluor 488-conjugated secondary antibody the cells were washed once with wash media. The Alexa Fluor 488-conjugated antibody in staining media was then added for 20 minutes. The cells were then washed for the final time and resuspended in staining media containing 1 microgram/mL propidium iodide. Flow cytometric acquisition of the cells was assessed by running samples on a FACScan using the CellQuest software (BD Biosciences). The forward (FSC) and side scatter (SSC) of the cells were set by adjusting the voltage and amplitude gains on the FSC and SSC detectors. The detectors for the three fluorescence channels (FL1, FL2, and FL3) were adjusted by running cells stained with purified isotype control antibody followed by Alexa Fluor 488-conjugated secondary antibody such that cells had a uniform peak with a median fluorescent intensity of approximately 1-5 units. Live cells were acquired by gating for FSC and propidium iodide exclusion. For each sample, approximately 10,000 live cells were acquired for analysis and the results presented in FIG. 6.

Figure 7:
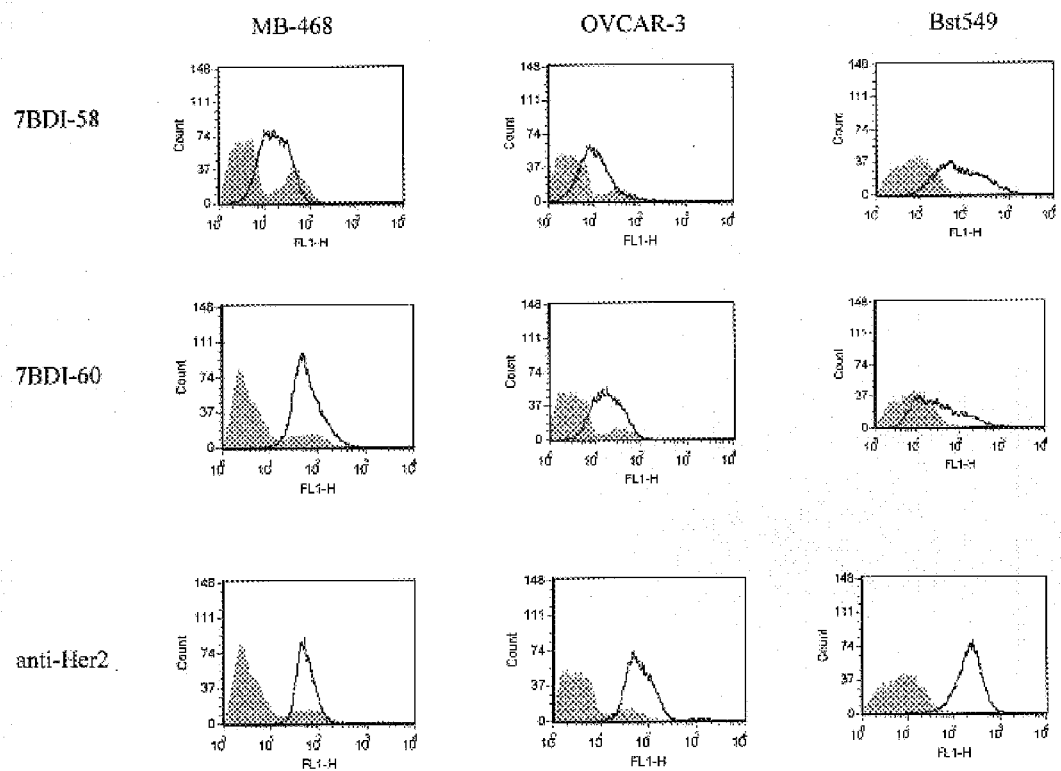
FIG. 7 includes representative FACS histograms of 7BDI-58, 7BDI-60 and anti-Her2 antibodies directed against several cancer and non-cancer cell lines.

FIG. 6 presents the mean fluorescence intensity fold increase above isotype control for each antibody. Representative histograms of 7BDI-58 and 7BDI-60 antibodies were compiled for FIG. 7. 7BDI-58 showed greater binding to the ovarian cancer cell line OVCAR-3 (13.8 fold), the non-cancer lung cell line Hs888.Lu (18.3 fold), the non-cancer breast cell line Bst549 (10.8 fold) and the non-cancer skin cell line CCD-27sk (22.5) with weaker binding to the breast cancer cell line MB-468 (3.8 fold). These data demonstrate that 7BDI-58 exhibited functional specificity in that although there was clear binding to a number of cell lines tested, there was only associated cytotoxicity with OVCAR-3 ovarian cancer. 7BDI-60 showed binding to the ovarian cancer cell line OVCAR-3 (5.7 fold), the breast cancer cell line MB-468 (5.1 fold), the non-cancer lung cell line Hs888.Lu (9.1 fold), the non-cancer breast cell line Bst549 (3.7 fold) and the non-cancer skin cell line CCD-27sk (8.1 fold). These data demonstrate that 7BDI-60 exhibited functional specificity in that although there was clear binding to a number of cell lines tested, there was only associated cytotoxicity with MB-468 breast cancer.

EXAMPLE 3

In vivo Tumor Experiments with MDA-MB-231 Cells

With reference to FIGS. 8 and 9, 4 to 6 week old female SCID mice were implanted with 5 million human breast cancer cells (MDA-MB-231) in 100 microliters saline injected subcutaneously in the scruff of the neck. The mice were randomly divided into 2 treatment groups of 5. On the day after implantation, 20 mg/kg of 7BDI-58 test antibody or buffer control was administered intraperitoneally to each cohort in a volume of 300 microliters after dilution from the stock concentration with a diluent that contained 2.7 mM KCl, 1 mM $KH_2PO_4$, 137 mM NaCl and 20 mM $Na_2HPO_4$. The antibody and control samples were then administered once per week for the duration of the study, a total of 8 doses, in the same fashion. Tumor growth was measured about every seventh day with calipers. Body weights of the animals were recorded once per week for the duration of the study. At the end of the study all animals were euthanized according to CCAC guidelines.

Figure 8:
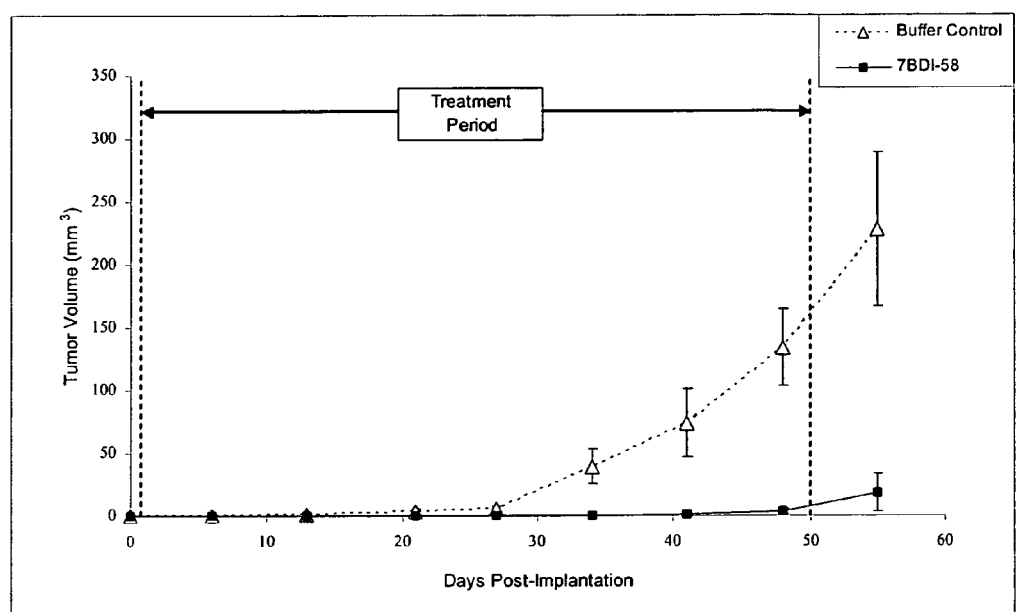
FIG. 8 demonstrates the effect of 7BDI-58 on tumor growth in a prophylactic MDA-MB-231 breast cancer model. The vertical dashed lines indicate the period during which the antibody was administered. Data points represent the mean +/−SEM.

7BDI-58 markedly reduced tumor growth in the MDA-MB-231 in vivo prophylactic model of human breast cancer. On day 55 post-implantation, 5 days after the last treatment dose, the mean tumor volume in the 7BDI-58 treated group was 91.2 percent lower than the tumor volume in the buffer control-treated group (FIG. 8). The tumor volume at the end of the study was significantly different from that of the control ($p=0.0105$, t-test).

Figure 9:
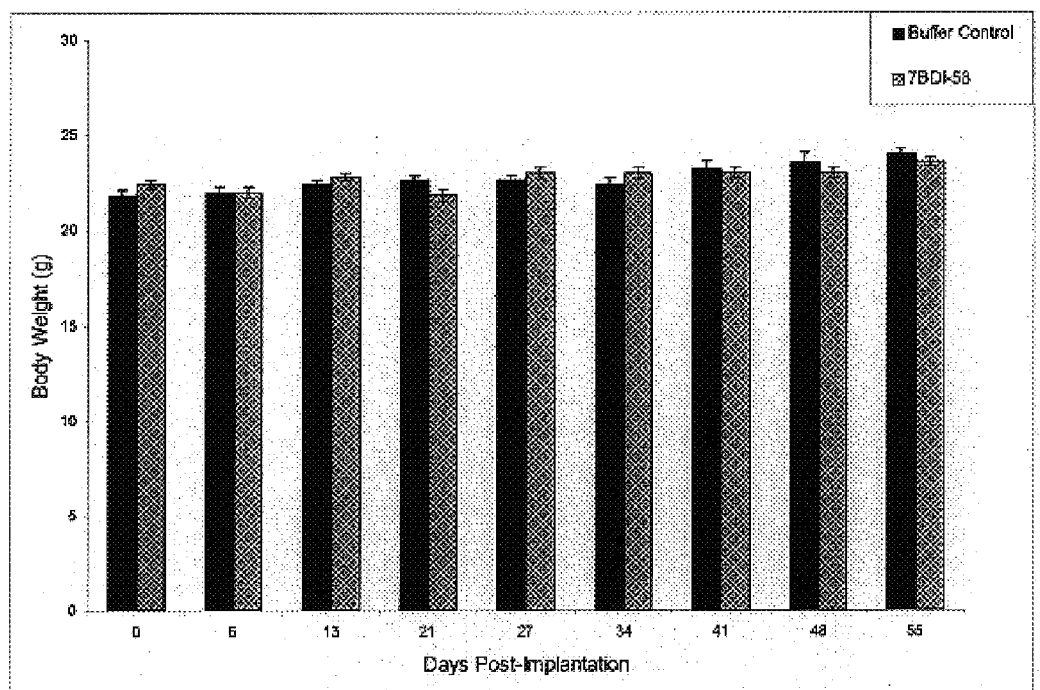
FIG. 9 demonstrates the effect of 7BDI-58 on body weight in a prophylactic MDA-MB-231 breast cancer model. Data points represent the mean +/−SEM.

There were no clinical signs of toxicity throughout the study. Body weight measured at weekly intervals was a surrogate for well-being and failure to thrive. As seen in FIG. 9, there were no significant differences in the body weights of the control or 7BDI-58-treated groups over the course of the study. There was also no significant difference in body weight between the two groups at the end of the treatment period.

In conclusion, 7BDI-58 was well-tolerated and decreased the tumor burden in this human breast cancer xenograft model.

EXAMPLE 4

Figure 10:
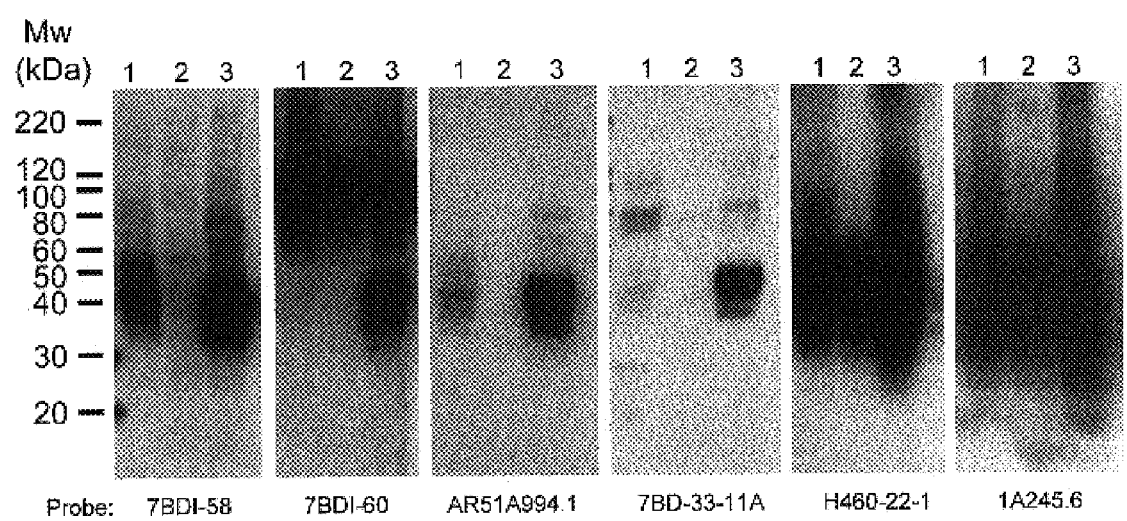
FIG. 10. Western blot of samples obtained from the total membrane fraction of MDA-MB-231 cells (lane 1) and from whole cell lysates of PC-3 (lane 2) and CCD-27sk (lane 3) cell lines. Blots were probed with 7BDI-58, 7BDI-60, AR51A994.1, 7BD-33-11A, 1A245.6 and H460-22-1 as described above.

Determination of Cross-reactivity Between the Monoclonal Antibodies 7BDI-58, 7BDI-60, AR55A994.1 and Anti-CD63 Antibodies Results from Western blots of total membrane fractions and of whole cell lysates, when probed with the monoclonal antibodies 7BDI-58, 7BDI-60 and AR51A994.1 revealed a strong similarity with those obtained with ARIUS' anti-CD63 monoclonal antibodies 7BD-33-11A, 1A245.6 and H460-22-1 (FIG. 10). In order to determine whether the former antibodies cross-reacted with CD63 they were used as probes on Western blots of immunoprecipitate complexes obtained with either 7BD-33-11A or with 1A245.6 from the total membrane fraction of cells grown in culture.

Briefly 300 micrograms of MDA-MB-231 total membrane fraction (1 mg/mL final protein concentration) was incubated with 7BD-33-11A-conjugated protein G Sepharose beads for 2 hours at 4° C. After washing the beads were boiled in 1× non-reducing SDS-PAGE sample buffer and the sample was analyzed by electrophoresis on a 10% polyacrylamide gel. After electrotransfer onto a PVDF membrane the blots were probed with the antibodies 7BDI-58, AR51A994.1, 7BD-33-11A and with IgG1 and IgG2a isotype controls according to standard Western blot procedure. All primary antibodies were used at a concentration of 5 micrograms/mL. The image of the resulting blots (FIG. 11) shows that both the 7BDI-58 and AR51A994.1 cross-reacted with the same antigen as the 7BD-33-11A antibody, and therefore that they bind specifically with CD63.

Figure 12:
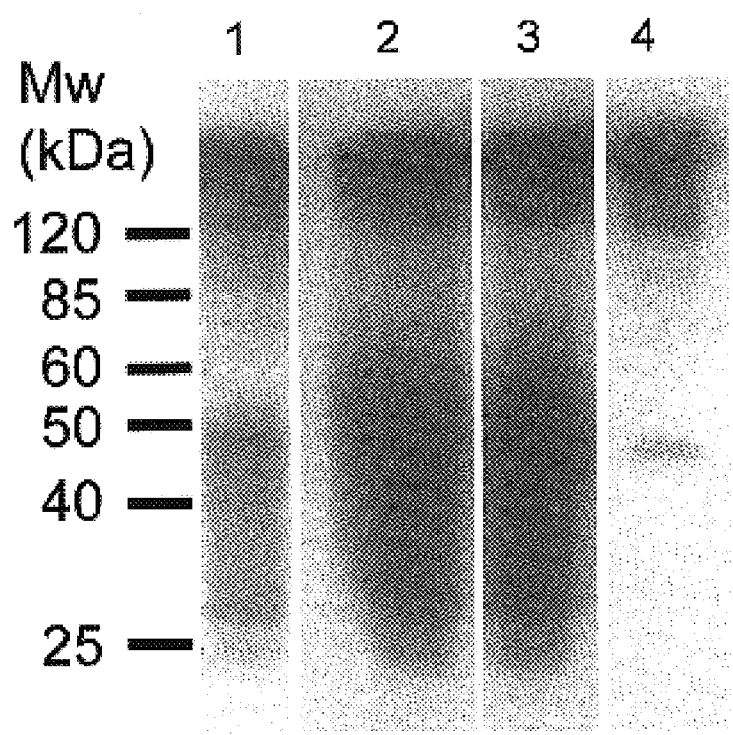
FIG. 12. Immunocomplex prepared by immunoprecipitation with 1A245.6 from the total membrane fraction of the ASPC-1 human pancreatic carcinoma cell line. Replicate lanes of the blot were probed with 7BDI-60 (lane 1), 1A245.6 (lane 2), anti-CD63 clone H5C6 (lane 3) and with an isotype control antibody (lane 4).

To determine if the antibody 7BDI-60 cross-reacted with CD63, immunocomplexes of human CD63 and the antibody 1A245.5 were prepared from the total membrane fraction isolated from the ASPC-1 cell line. After analyzing the immunocomplexes by electrophoresis, under non-reducing conditions, on a 10% SDS-polyacrylamide gel, and after electrotransfer of the proteins onto a PVDF membrane, the blots were probed with the antibodies 7BDI-60, 1A245.6, anti-CD63 clone H5C6, and with an IgG1 isotype control. All primary antibodies were used at a concentration of 5 micrograms/mL. FIG. 12 demonstrates that all antibodies, with the exception of the isotype control, cross-reacted with the same antigen, CD63.

Figure 13:
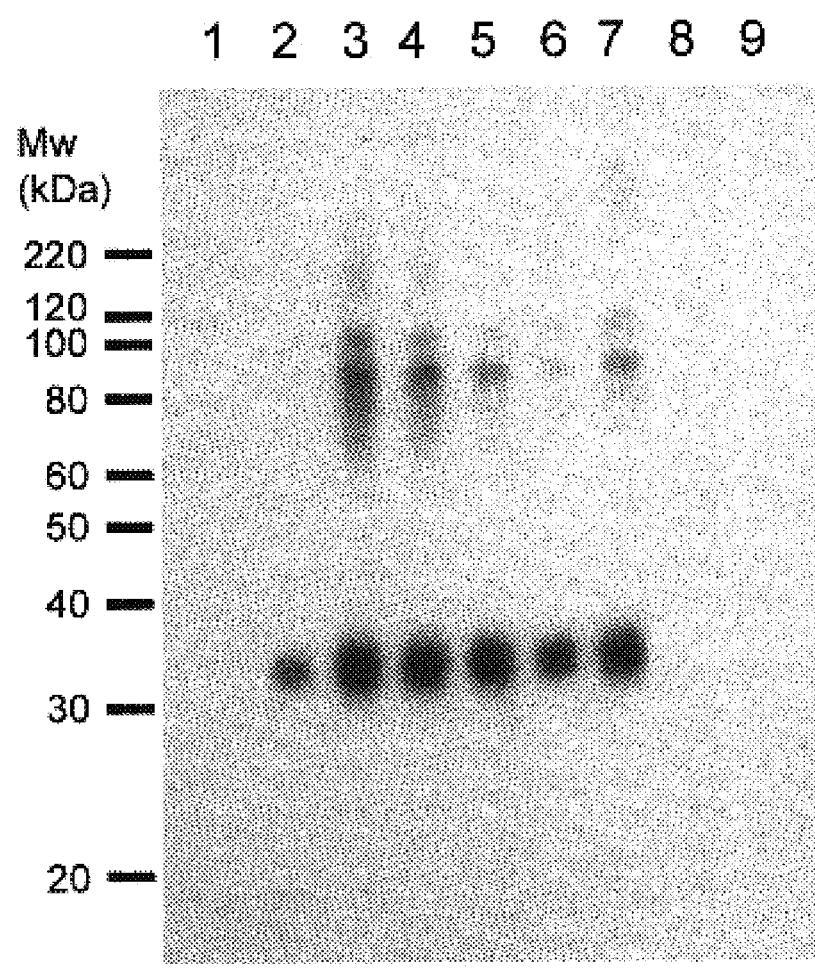
FIG. 13. Western blot of human recombinant fusion construct GST-EC2 (CD63). Individual lanes of the blot were probed with 7BDI-58 (lane 1), 7BDI-60 (lane 2), AR51A994.1 (lane 3), 7BD-33-11A (lane 4), H460-22-1 (lane 5), 1A245.6 (lane 6) and with negative controls H460-16-2 (anti-CD44; lane 7) and isotype control antibodies (lanes 8 and 9).

To further confirm the cross-reactivity between 7BDI-58, 7BDI-60 and AR51A994.1 against human CD63, the antibodies were used as probes on a Western blot of E.coli-expressed recombinant GST-fusion construct of the largest extracellular loop of human CD63. Briefly 5 micrograms of purified recombinant GST-fusion protein was analyzed by electrophoresis on a 10% preparative SDS-polyacrylamide gel. After transfer the blot was probed with the 7BDI-58, 7BDI-60 and AR51A994.1, and with the anti-CD63 antibodies 7BD-33-11A, 1A245.6 and H460-22-1, with an anti-CD44 antibody (clone H460-16-2) and with IgG1 and IgG2a isotype control antibodies, according to standard Western blot procedure. All primary antibodies were used at a concentartion of 5 micrograms/mL. The results from this experiment (FIG. 13) revealed that all antibodies, with the exception of the isotype control, cross-reacted specifically with the recombinant GST-fusion construct of human CD63 largest extracellular loop, therefore demonstrating that 7BDI-58, 7BDI-60 and AR51A994.1 bind specifically with human CD63.

EXAMPLE 5

Human Pancreatic Tumor Tissue Staining

IHC studies were conducted to further (initial staining of pancreatic adenocarcinoma disclosed in Ser. No. 10/603,006) evaluate the binding of 7BD-33-11A to human pancreatic tumor tissue. IHC optimization studies were performed previously in order to determine the conditions for further experiments.

Tissue sections were deparaffinized by drying in an oven at 58° C. for 1 hour and dewaxed by immersing in xylene 5 times for 4 minutes each in Coplin jars. Following treatment through a series of graded ethanol washes (100%-75%) the sections were re-hydrated in water. The slides were immersed in 10 mM citrate buffer at pH 6 (Dako, Toronto, Ontario) then microwaved at high, medium, and low power settings for 5 minutes each and finally immersed in cold PBS. Slides were then immersed in 3% hydrogen peroxide solution for 6 minutes, washed with PBS three times for 5 minutes each, dried, incubated with Universal blocking solution (Dako, Toronto, Ontario) for 5 minutes at room temperature. 7BD-33-11A, monoclonal mouse anti-actin (Dako, Toronto, ON) or isotype control antibody (directed towards Aspergillus niger glucose oxidase, an enzyme which is neither present nor inducible in mammalian tissues; Dako, Toronto, Ontario) were diluted in antibody dilution buffer (Dako, Toronto, Ontario) to its working concentration (5 microgrnas/mL for each antibody except for anti-actin which was diluted to 2 micrograms/mL) and incubated for 1 hour at room temperature. The slides were washed with PBS 3 times for 5 minutes each. Immunoreactivity of the primary antibodies was detected/visualized with HRP conjugated secondary antibodies as supplied (Dako Envision System, Toronto, Ontario) for 30 minutes at room temperature. Following this step the slides were washed with PBS 3 times for 5 minutes each and a color reaction developed by adding DAB (3,3'-diaminobenzidine tetrahydrachloride, Dako, Toronto, Ontario) chromogen substrate solution for immunoperoxidase staining for 10 minutes at room temperature. Washing the slides in tap water terminated the chromogenic reaction. Following counterstaining with Meyer's Hematoxylin (Sigma Diagnostics, Oakville, ON), the slides were dehydrated with graded ethanols (75-100%) and cleared with xylene. Using mounting media (Dako Faramount, Toronto, Ontario) the slides were coverslipped. Slides were microscopically examined using an Axiovert 200 (Zeiss Canada, Toronto, ON) and digital images acquired and stored using Northern Eclipse Imaging Software (Mississauga, ON). Results were read, scored and interpreted by a histopathologist.

Testing for binding of antibodies to 32 human pancreatic tumor and 4 normal pancreatic tissues was performed using a human, pancreatic normal and tumor tissue microarray (Pentagen, Seoul, Korea). FIG. 14 presents a summary of the results of 7BD-33-11A staining of an array of human normal and tumor pancreatic tissues. Each tumor sample is represented by 2 spots to overcome tissue heterogeneity. The average score for the 2 spots was considered as the final section tumor. There was only one spot available for each of the four non-neoplastic tissues.

As shown in FIG. 14, the total binding of 7BD-33-11A to pancreatic cancer tested on the microarray was 27/32 (84%). The antibody showed strong (+++) staining in 3/32, moderate (++) in 7/32, weak (+) in 9/32 and equivocal (+/−) in 8/32. The binding was restricted to tumor cells. The cellular localization was cytoplasmic and membranous with a granular staining pattern. The percentage of the stained cells showed heterogeneous binding to the tumor cells, ranging between <10 % to >50%. According to the histological type of the pancreatic tumors available on the tissue microarray, there was binding to 26/30 (87%) of ductal adenocarcinoma and to 1/2 (50%) of endocrine carcinomas. There was binding to 4/4 (100%) of non-neoplastic pancreatic tissues; the binding was to acinar epithelium and islets of langerhans (FIG. 15).

According to the histological grade of the pancreatic tumors, there was binding of the antibody to 1/1 (100%), 2/3 (67%), 9/12 (75%), 2/2 (100%), 6/6 (100%), and 1/1 (100%) to sections graded as G1, G1-G2, G2, G2-G3, G3, G4, respectively. There was binding to 5/5 (100%) of the sections with unknown grade. In relation to tumor TNM stages of adenocarcinoma of the pancreas, there was binding of the antibody to 1/1 (100%), 14/17 (82%), 1/1 (100%) and 10/11 (91%) sections from stages I, II, III and IV, respectively. Therefore, no relation could be found between the antibody binding and various cancer parameters (histological tumor types, grades and TNM stages). This lack of correlation may be due to the small sample sizes representing some of the cancer stages.

The 7BD-33-11A antigen appears to be expressed on pancreatic tumor tissue. 7BD-33-11A therefore has potential as a therapeutic drug in the treatment of pancreatic cancer.

EXAMPLE 6

Demonstration of In vitro Antibody-Dependent Cellular Cytotoxicity (ADCC) Activity of the Antibody 7BD-33-11A Previous evidence from in vivo therapeutic use of 7BD-33-11A on prophylactic human breast cancer models, obtained by comparing its efficacy in SCID versus NOD/SCID mice (as disclosed in Ser. No. 60/642,057), indicated that ADCC is a possible mechanism for the in vivo activity of this antibody in that animal model. Further demonstration of the ability of 7BD-33-11A to mediate antibody-dependent cellular cytotoxicity against the MDA-MB-231 breast cancer cell line was obtained by an in vitro cytotoxicity assay. Murine effector cells were obtained from the spleens of BALB/cAJcl⁻ nu⁻ mice and were stimulated with murine IL-2 (20 nM) for four days. Adherent and non-adherent effector cells were separated and used in the in vitro cytotoxicity assay. MDA-MB-231 target cells were dissociated from the cell culture plate and 10 million cells were labeled for 60 minutes with 40 μCi of $Na_2{}^{51}CrO_4$ (GE Healthcare Amersham Biosciences) and $10^4$ cells/well were added to 96-well plates. 7BD-33-11A or an IgG2a isotype-matched control were added to the $^{51}$Crlabeled target cells, at varying final concentrations immediately before adding the murine effector cells at effector: target (E:T) ratio of 25:1. After a 4 hour incubation at 37° C. the $^{51}$Cr released from the lysed cells was measured. Each assay was carried out in triplicate and the results were expressed as the percentage of specific lysis which is defined as: (experimental cpm-spontaneous cpm)×100/(maximum cpm-spontaneous cpm).

The results from this experiment (FIG. 16) clearly demonstrate that 7BD-33-11A induces a specific and dose-dependent MDA-MB-231 target cell lysis, both with adherent and non-adherent effector cells, that is not observed when the target cells are incubated in the presence of the isotype-matched control, at identical concentrations. Therefore, the data demonstrate that 7BD-33-11A is able to mediate ADCC by recruiting effector cell activity.

EXAMPLE 7

Macrophage Accumulation in MDA-MB-231 Xenografts

Additional demonstration of the ability of 7BD-33-11A in mediating antibody-dependent cellular cytotoxicity against the MDA-MB-231 breast cancer cell line was obtained from an in vivo study by immunohistochemistry.

Six to eight week old female SCID mice were implanted with 5 million human breast cancer cells (MDA-MB-231) in 100 microliters saline injected subcutaneously in the scruff of the neck. Tumor growth was measured with calipers every week. When the majority of the cohort reached an average tumor volume of 100 mm$^3$ (range 80-120 mm$^3$), 3 mice were sacrificed, and their tumors were harvested and portions were preserved in formalin and OCT. The remainder of the mice were assigned to treatment or control groups with 3 mice/group. The day after assignment, 7BD-33-11A test antibody or buffer control was administered intraperitoneally to each cohort, with dosing at 15 mg/kg of antibodies in a volume of 300 microliters after dilution from the stock concentration with a diluent that contained 2.7 mM KCl, 1 mM KH$_2$PO$_4$, 137 mM NaCl and 20 mM Na$_2$HPO$_4$. After 3, 6 or 10 doses of test antibody or control, given 3 times/week, mice were sacrificed and tumors were harvested and preserved in formalin and OCT. Tumor samples were transferred to the Pathology Research Lab in the Toronto General Hospital (Toronto, ON) for processing.

Tissue sections were deparaffinized by drying in an oven at 58° C. for 1 hour and dewaxed by immersing in xylene 5 times for 4 minutes each in Coplin jars. Following treatment through a series of graded ethanol washes (100%-75%) the sections were re-hydrated in water. The slides were immersed in 10 mM citrate buffer at pH 6 (Dako, Toronto, Ontario) then microwaved at high, medium, and low power settings for 5 minutes each and finally immersed in cold PBS. Slides were then immersed in 3% hydrogen peroxide solution for 6 minutes, washed with PBS three times for 5 minutes each, dried, incubated with Universal blocking solution (Dako, Toronto, Ontario) for 5 minutes at room temperature, Avidin D blocking solution (Vector Laboratories, Burlingame, Calif.) for 15 minutes at room temperature and Biotin blocking solution (Vector Laboratories, Burlingame, Calif.) for 15 minutes at room temperature. Anti-Mac-3 (BD Bioscience, Oakville, ON) was diluted in antibody dilution buffer (Dako, Toronto, Ontario) to its working concentration (0.75 micrograms/mL) and incubated for 1 hour at room temperature. Slides incubated with antibody dilution buffer alone were used as a negative control. The slides were washed with PBS 3 times for 5 minutes each. Immunoreactivity of the primary antibodies was detected/visualized with biotinylated anti-rat (BD Bioscience, Oakville, ON). The color reaction was detected with Vectastain EliteABC reagent (Vector Laboratories, Burlingame, Calif.). Washing the slides in tap water terminated the chromogenic reaction. Following counterstaining with Meyer's Hematoxylin (Sigma Diagnostics, Oakville, ON), the slides were dehydrated with graded ethanols (75-100%) and cleared with xylene. Using mounting media (Dako Faramount, Toronto, Ontario) the slides were coverslipped. Slides were microscopically examined using an Axiovert 200 (Zeiss Canada, Toronto, ON) and digital images acquired and stored using Northern Eclipse Imaging Software (Mississauga, ON). Results were read, scored and interpreted by a histopathologist. Scanning of the slides was done at 100× magnification power (Ziess Axiovert 200M). Macrophages (Mac-3 positive) were counted by randomly selecting 5 different hot spots. Intratumoral areas were selected for counting while avoiding the peripheral dense zones. After selecting the areas to be counted, magnification power was shifted to 400× and images were captured using a QImaging Retiga camera and Northern Eclipse software (Version 7.0). Manual counting of positive cells was done using the Northern Eclipse manual counting function. The necrotic areas and vascular spaces were avoided during counting.

Examination of tumor sections showed 3 distribution patterns of tumor associated macrophages. There was peripheral infiltration in a band like pattern between the periphery of tumor and the surrounding connective tissue. This pattern was obvious in all 7BD-33-11A treated tumors but only in some of buffer treated tumors. There was also aggregation in groups among the tumor cells, and lastly, there were sporadic single cells among or that encircled the tumor cells.

As displayed in FIG. 17, 7BD-33-11A-treatrnent resulted in higher accumulation of macrophages compared to buffer treatment at all 3 doses. The highest accumulation was with the 6 dose samples, and was statistically significant (p=0.047). This correlated with the data illustrating that the greatest percentage tumor growth inhibition was seen after 6 doses of 7BD-33-11A. In addition, when taking into account the data from all 3 doses, the accumulation of macrophages in the 7BD-33-11A treated tumors was also significantly higher (p=0.037). All samples incubated with antibody dilution buffer alone were negative.

Therefore, in MDA-MB-231 xenografts, there was significant accumulation of tumor-associated macrophages in the 7BD-33-11A-treatment versus the buffer-treatment xenografts. This data supports the previous evidence of ADCC as a mechanism of action for 7BD-33-11A.

EXAMPLE 8

Humanization of 7BD-33-11A

Humanization of 7BD-33-11A was carried out essentially according to the procedure of Queen et al. (1989) by Protein Design Labs (PDL, Fremont, Calif.). First, human variable (V) regions, with high homology to the amino acid sequences of the variable regions of the heavy and light chains ($V_H$ and $V_L$, respectively) of 7BD-33-11A, were identified. Next, the CDR sequences together with framework amino acids important for maintaining the structures of the CDRs were grafted into the selected human framework sequences. In addition, human framework amino acids that were found to be atypical in the corresponding human V region subgroup were substituted with consensus amino acids to reduce potential immunogenicity. The resulting humanized variable regions were expressed in the IgG1 and IgG2M3 forms ((hu)AR7BD-33-

11A-IgG1(V11L) and (hu)AR7BD-33-11A-IgG2M3 (V11L), respectively) in the mouse myeloma cell line Sp2/0.

The hybridoma cell line 7BD-33-11A, which produces mouse anti-human CD63 monoclonal antibody was cultured in DMEM (HyClone, Logan, Utah) containing 10% FBS (HyClone, Logan, Utah), 1% MEM-Non Essential Amino Acids (BioWhittaker, Walkersville, Md.), 0.1% 2-mercaptoethanol (Sigma, St. Louis, Mo.), 1% sodium pyruvate (Invitrogen, Carlsbad, Calif.), 1% L-glutamine (Invitrogen, Carlsbad, Calif.). Mouse myeloma cell line Sp2/0-Ag14 (ATCC, Manassus, Va.; referred to as Sp2/0 hereinafter) was maintained in DMEM containing 10% FBS. Mouse monoclonal antibody 7BD-33-11A was purified from culture supernatant by affinity chromatography using a Protein G Sepharose column. FITC-conjugated 7BD-33-11A was prepared using the FluoReporter Fluorescein-EX Protein Labeling Kit (Molecular Probes, Eugene, Oreg.). Human prostate cancer cell line PC-3, which was originally obtained from the National Cancer Institute, was maintained in RPMI-1640 (BioWhittaker, Walkersville, Md.) containing 10% FBS. All the cell lines were maintained at 37° C. in a 7.5% $CO_2$ incubator.

Sequencing of N-terminal amino acids of 7BD-33-11A was performed at Argo BioAnalytica, Inc. (Kenilworth, N.J.). The observed amino acid sequence shown in FIG. 18 was consistent with the sequence predicted from the mouse light chain and heavy light chain variable region genes.

Total RNA was extracted from approximately $10^7$ 7BD-33-11A hybridoma cells using TRIzol reagent (Invitrogen, Carlsbad, Calif., Burlington, ON) and poly $(A)^+$ RNA was isolated with the PolyATtract mRNA Isolation System (Promega Corporation, Madison, Wis.) according to the suppliers' protocols. Double-stranded cDNA was synthesized using the SMART RACE cDNA Amplification Kit (BD Biosciences Clontech, Palo Alto, Calif.) following the supplier's protocol. The variable region cDNAs for the heavy and light chains were amplified by polymerase chain reaction (PCR) using 3' primers that anneal, respectively, to the mouse gamma and kappa chain C regions, and a 5' universal primer provided in the SMART RACE cDNA Amplification Kit. For $V_H$ PCR, the 3' primer had the sequence 5'-GCCAGTG-GATAGACCGATGG-3'(SEQ ID NO:15). For $V_L$ PCR, the 3' primer had the sequence 5'-GATGGATACAGTTGGTG-CAGC-3' (SEQ ID NO:16). The $V_H$ and $V_L$ cDNAs were subcloned into the pCR4Blunt-TOPO vector (Invitrogen, Carlsbad, Calif.) for sequence determination. DNA sequencing was carried out by PCR cycle sequencing reactions with fluorescent dideoxy chain terminators (Applied Biosystems, Foster City, Calif.) according to the manufacturer's instructions. The sequencing reactions were analyzed on a Model 3100 Genetic Analyzer (Applied Biosystems, Foster City, Calif.). Unique sequences homologous to typical mouse light and heavy chain variable regions were identified. The $V_L$ and $V_H$ sequences were found to belong to subgroups I and IIA, respectively. The cDNA sequences encoding the light and heavy chain variable regions are shown in FIGS. 19 and 20, respectively. The deduced sequences of the N-terminal 20 amino acids from cDNA sequence analysis matched the corresponding sequences determined by amino acid sequencing for both the light and heavy chains.

Design of the humanized antibody V regions was carried out as disclosed by Queen et al. (1989). The human V region frameworks used as acceptors for the CDRs of 7BD-33-11A were chosen based on sequence homology. The computer programs ABMOD and ENCAD (Levitt, 1983) were used to construct a molecular model of the variable regions. Amino acids in the humanized V regions predicted to have contact with the CDRs were substituted with the corresponding residues of 7BD-33-11A. Amino acids in the humanized V region that were found to be atypical in the same V region subgroup were changed to consensus amino acids to eliminate potential immunogenicity. Based on a homology search against human V and J region sequences, the human V region AAR32409 (Huang et al., 1997) and J segment JH6 (Ravetch et al., 1981) were selected to provide the frameworks for the (hu)AR7BD-33-11A heavy chain variable region. For the (hu)AR7BD-33-11A light chain variable region, the human V region 1LVE (Miura et al. 2003) and J segment JK2 (Hieter et al., 1982) were used. The identity of the framework amino acids between 7BD-33-11A $V_H$ and the human acceptor AAR32409/JH6 was 77%, while the identity between 7BD-33-11A $V_L$ and the human acceptor 1L VE/JK2 was 88%.

At framework positions in which the computer model suggested significant contact with the CDRs, the amino acids from the V regions were substituted for the original human framework amino acids. This was done at residues 30, 48, 67, 68, 70, 72, 74, 97 and 98 of the heavy chain. For the light chain, replacement was made at residue 22. Framework residues that occurred only rarely at their respective positions in the corresponding human V region subgroups were replaced with human consensus amino acids at those positions. This was done at residues 38, 40 and 84 of the heavy chain. The alignments of 7BD-33-11A, designed (hu)AR7BD-33-11A and the acceptor human V region amino acid sequences for $V_L$ and $V_H$ are shown in FIGS. 21 and 22, respectively.

Figure 27:
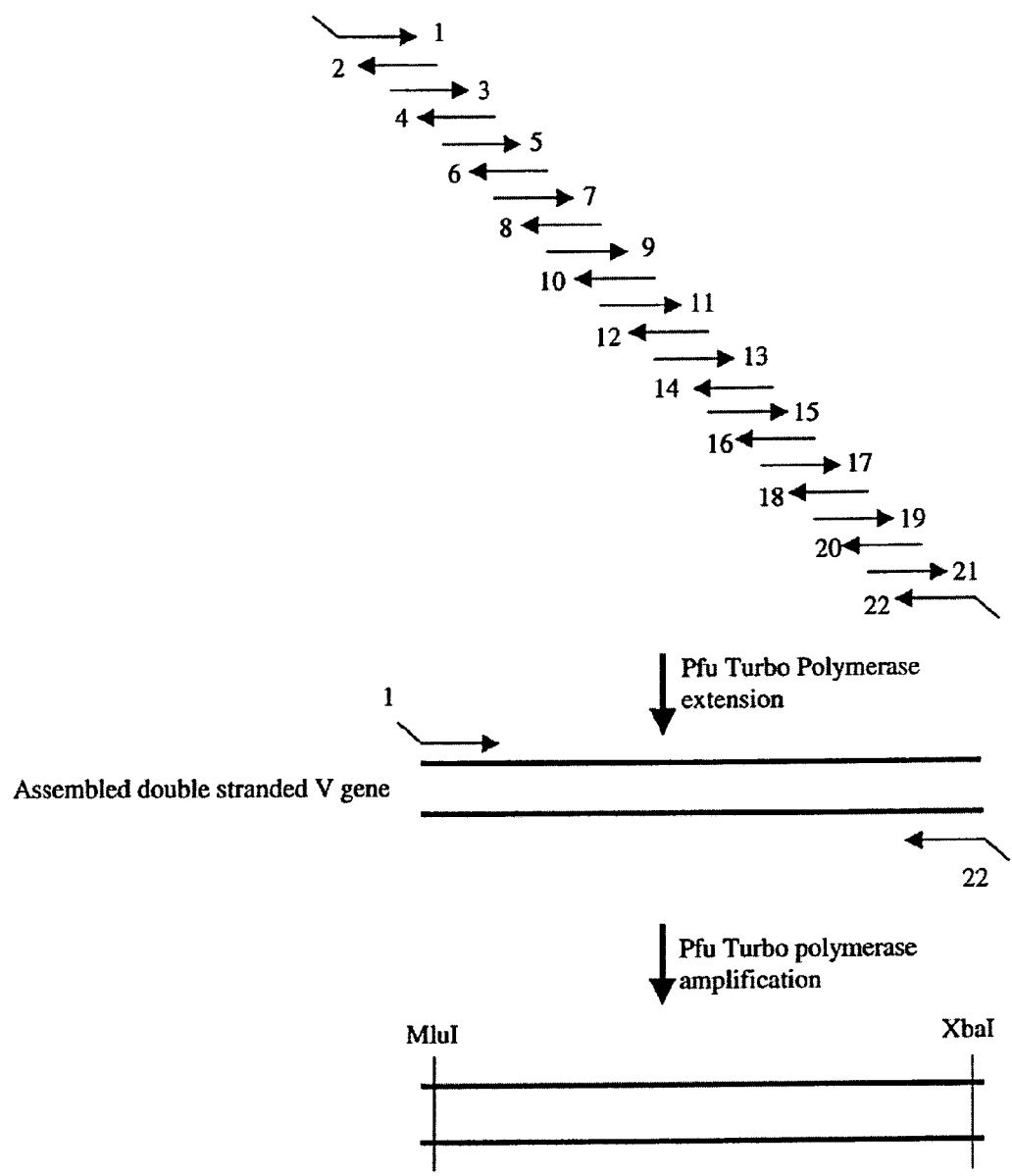
FIG. 27. Scheme for the synthesis of the (hu)AR7BD-33-11A $V_L$ or $V_H$ mini-exons. A series of 20 (for $V_L$) or 22 (for $V_H$; as illustrated in the Figure) overlapping oligonucleotides were used. Oligonucleotides 1-20 (for $V_L$) or 1-22 (for $V_H$) were annealed and extended with Pfu Turbo polymerase. The resulting assembled double stranded V gene was amplified by 5' and 3' flanking oligonucleotides to yield $V_L$ and $V_H$ gene fragments, which were gel purified, digested with MluI and XbaI, and subcloned into the pVk and pVg1.D.Tt or pVg2M3.D.T vectors, respectively.

The heavy and light chain variable region genes were constructed and amplified using 20 (for light chain) or 22 (for heavy chain) overlapping synthetic oligonucleotides approximately 40 base pairs in length (Stemmer et al., 1995). The oligonucleotides were annealed and extended with the Pfu Turbo Polymerase (Stratagene, La Jolla, Calif.), yielding an assembled double-stranded full-length V gene. The assembled heavy and light chain V gene fragments were amplified by PCR using Pfu Turbo Polymerase. The PCR-amplified fragments were gel-purified, digested with MluI and XbaI, gel-purified, and subcloned, respectively, into pVg1.D.Tt or pVg2M3.D.Tt (Cole et al., 1997) and pVk (Co et al., 1992). Plasmid pVg1.D.Tt is similar to pVg2M3.D.Tt (Cole et al., 1997), but it contains a genomic fragment encoding the ?1 constant region instead of the ?2 constant region. Single amino acid substitutions were introduced by a PCR-based single step gene assembly method with 22 overlapping oligonucleotides (Stemmer et al., 1995) using Pfu Turbo Polymerase to generate a set of (hu)AR7BD-33-11A $V_H$ variants (V24A, R38K, and V24A,R38K). Site-directed mutagenesis was carried out by overlap-extension PCR using High Fidelity Expand Polymerase (Roche Diagnostics, Indianapolis, IN) to generate another set of (hu)AR7BD-33-11A $V_H$ variants (V11L, I20M, and Q111A). Genes encoding humanized $V_L$ or $V_H$ were designed as mini-exons (FIGS. 23 and 24) including signal peptides, splice donor signals, and appropriate restriction enzyme sites for subsequent cloning into mammalian expression vectors. The splice donor signals in the $V_L$ and $V_H$ mini-exons were derived from the corresponding human germline JK and JH sequences, respectively. The signal peptide sequences in the humanized $V_L$ and $V_H$ mini-exons were derived from the mouse anti-E/P selectin monoclonal antibody EP5C7 $V_L$ and $V_H$ regions (He et al., 1998). The (hu)AR7BD-33-11A $V_L$ and $V_H$ genes were constructed by extension of 20 and 22 overlapping synthetic oligonucleotides (FIGS. 25 and 26), respectively, and PCR amplification, as illustrated in FIG. 27. Oligonucleotides 1-20 for $V_L$ and 1-22 for $V_H$ were mixed, annealed and extended by PCR with Pfu Turbo DNA polymerase. The resulting V gene double-stranded DNA assembly was amplified by PCR with primers 1 and 20 (for $V_L$) or 1 and 22 (for $V_H$) to incorporate the flanking MluI and XbaI sites. The resulting $V_L$ gene fragment was cloned into the mammalian expression vector pVk (Co et al., 1992) to generate pVk-(hu)AR7BD-33-11A. The $V_H$ fragment was cloned into pVg1.D.Tt and pVg2M3.D.Tt (Cole et al., 1997) to generate pVg1-(hu)AR7BD-33-11A and pVg2M3-(hu)AR7BD-33-11A, respectively.

Transient transfection was done by co-transfection of pVg1-(hu)AR7BD-33-11A or pVg2M3-(hu)AR7BD-33-11A and pVk-(hu)AR7BD-33-11A into 293-H cells maintained in RPMI-1640 containing 2% low Ig FBS (HyClone, Logan, Utah) using the Lipofectamine method according to the supplier's recommendations. Approximately $7 \times 10^6$ cells were transfected with 15 micrograms each of light and heavy chain plasmids that had been allowed to form complexes with 70 microliters of Lipofectamine 2000 reagent. The cells were incubated for 5-7 days in a C02 incubator.

Purification of the transiently expressed (hu)AR7BD-33-11A.IgG1 and (hu)AR7BD-33-11A.IgG2M3 antibodies was carried out by Protein A Sepharose column chromatography. The affinity of these two antibodies to human CD63 was analyzed in a FACS competition assay. 7BD-33-11A, (hu)AR7BD-33-11A.IgGI and (hu)AR7BD-33-11A.IgG2M3 antibodies competed with FITC-conjugated AR7BD-33-11A in a concentration-dependent manner. $IC_{50}$ values of the 7BD-33-11A, (hu)AR7BD-33-11A-IgG1 and (hu)AR7BD-33-11A-IgG2M3 antibodies, obtained using the computer software GraphPad Prism (GraphPad Software Inc., San Diego, Calif.), were 7.02 micrograms/mL, 25.3 micrograms/mL and 62.3 micrograms/mL, respectively (FIG. 28). The affinity of (hu)AR7BD-33-11A-IgG1 was 3.6-fold lower than that of 7BD-33-11A.

Figure 29:
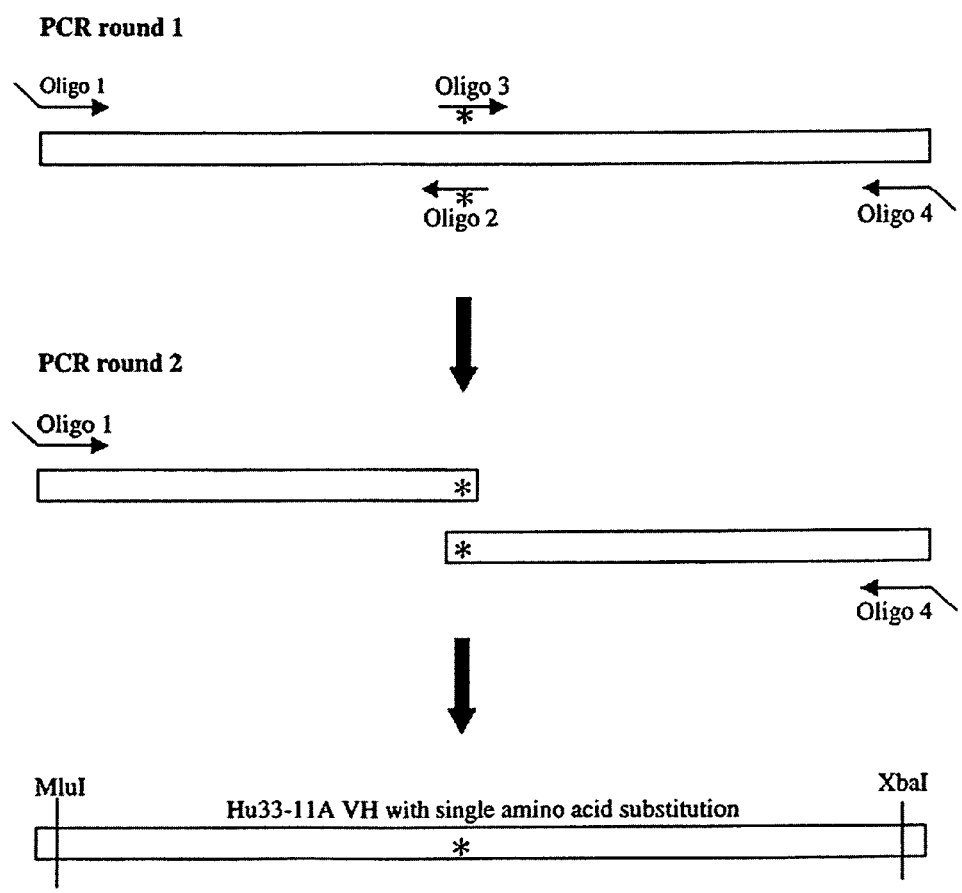
FIG. 29. Scheme for generating single amino acid substitution $V_H$ mutants by site-directed mutagenesis. Two separate rounds of PCR were carried out. In the first round of PCR, two partial $V_H$ gene fragments were amplified. These two fragments were further amplified together in the second round of PCR, to generate a full length $V_H$ gene fragment with a single amino acid substitution. The $V_H$ gene with the desired mutation was subcloned into pVg1.D.Tt and pVg2M3.D.T using the flanking MluI and XbaI sites.

To recover the antigen-binding affinity of 7BD-33-11A that was lost during humanization, several single amino acid substitutions from human residues to mouse residues were made in the $V_H$ by extension of 22 overlapping synthetic oligonucleotides and PCR amplification (V24A and R38K) and by site-directed mutagenesis (V11L, I20M and Q111A) as illustrated in FIG. 29. For each mutant, the number in the middle denotes the location of the amino acid substitution, and the left and right letters denote amino acids before and after mutation in single letter code, respectively. The V24A and R38K mutants were combined to generate a double amino acid substitution mutant (V24A,R38K). The Six $V_H$ mutants were cloned into pVg1 as described above.

The six variant (hu)AR7BD-33-11A IgG1 antibodies were expressed transiently in 293-H cells and purified by Protein A Sepharose column chromatography, and their affinity to human CD63 was analyzed by the FACS competition method. The six antibodies competed with FITC-conjugated 7BD-33-11A in a concentration-dependent manner. Their $IC_{50}$ values are shown in FIG. 28. Among them, only the V11L variant showed higher binding to CD63 than the wild type and other variant antibodies. The affinity of the (hu)AR7BD-33-11A-IgG1 antibody carrying the V11L substitution in the $V_H$ ((hu)AR7BD-33-11A-IgG1(V11L)) was within 3-fold of that of 7BD-33-11A.

Figure 30:
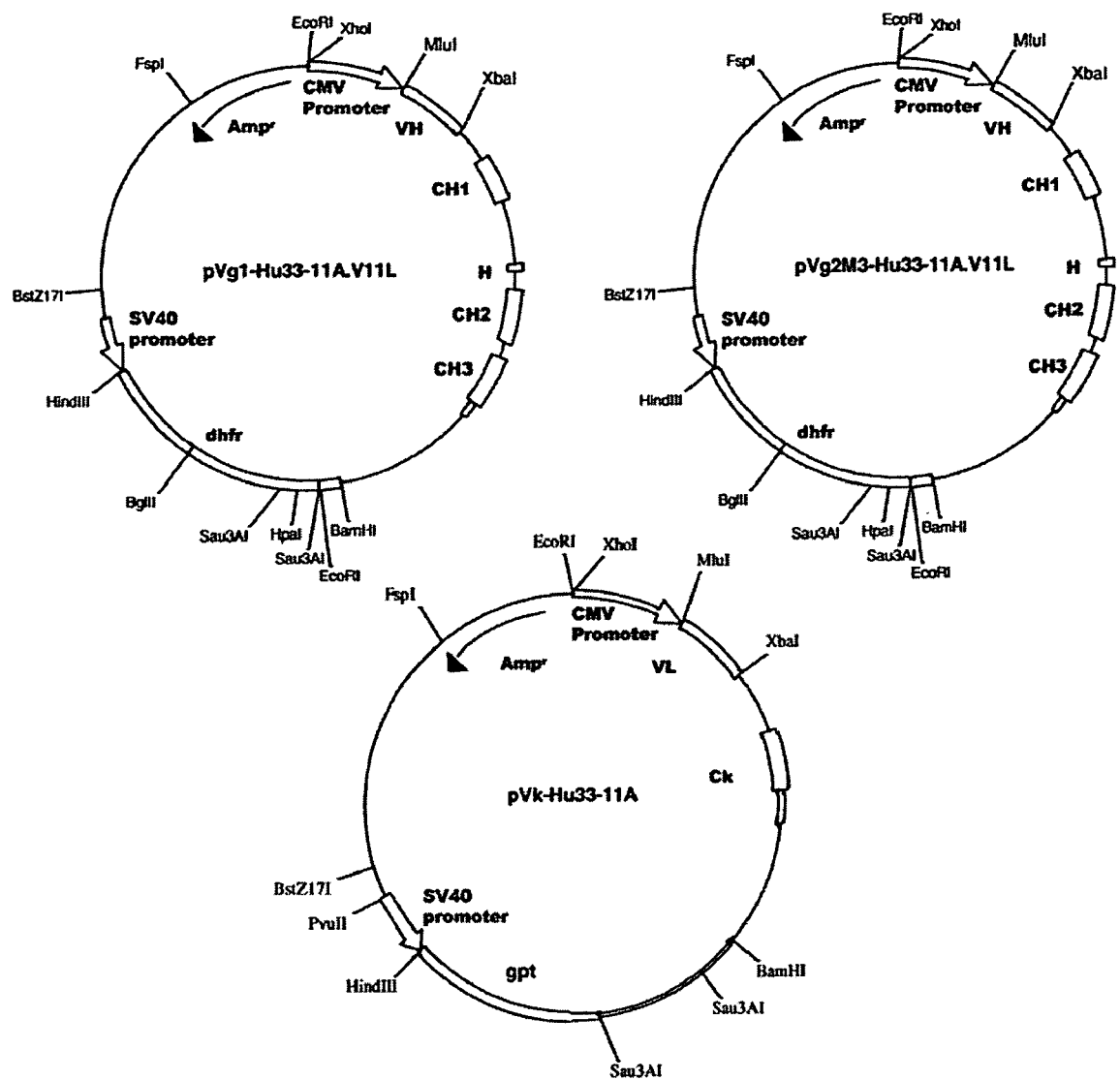
FIG. 30. Plasmid constructs for expression of (hu)AR7BD-33-11A(V11L) antibodies. The $V_L$ and $V_H$ genes were constructed as mini-exons flanked by MluI and XbaI sites. The V regions were incorporated into the corresponding expression vectors.

The heavy chain expression vector pVg1-(hu)AR7BD-33-11A carrying the V11L mutation (pVg1-(hu)AR7BD-33-11A(V11L)) was generated as described above. For expression of (hu)AR7BD-33-11A-IgG2M3(V11L), the (hu)AR7BD-33-11A $V_H$ gene carrying the V11L mutation was cloned into pVg2M3.D.Tt (Cole et al., 1997) as described above, generating pVg2M3-(hu)AR7BD-33-11A.V11L. The light chain constant region was derived from the human germline κ fragment (Hieter et al., 1980), and the heavy chains were derived from the human germline γ1 (Ellison et al., 1982) and human γ2M3 (Cole et al., 1997) fragments, respectively. It should be noted that the penultimate residue of the γ2M3 heavy chain encoded in pVg2M3(hu)AR7BD-33-11A.V11L is glycine, a more typical residue than the serine used by Cole et al. (1997). The human cytomegalovirus major immediate early promoter and enhancer drive both the light and heavy chain genes. The selection marker, a gpt gene, is driven by the SV40 early promoter. The gross structures of the final plasmids, as shown in FIG. 30, were verified by restriction mapping. The sequences of the variable and constant region exons of the light and heavy chain genes were verified by nucleotide sequencing.

To obtain cell lines stably producing (hu)AR7BD-33-11A-IgG1(V11L) and (hu)AR7BD-33-11A-IgG2M3(V11L), the corresponding heavy and light chain expression vectors were introduced into the chromosome of mouse myeloma cell line Sp2/0 by electroporation. Stable transfection into Sp2/0 was carried out by electroporation essentially as described by Co et al. (1992). Before transfection, the expression vectors were linearized using FspI. Approximately $10^7$ cells were co-transfected with 25 micrograms and 50 micrograms of linearized light and heavy chain plasmids, respectively. The transfected cells were suspended in DMEM (BioWhittaker, Walkersville, Md.) containing 10% FBS (HyClone, Logan, Utah) and plated at 100 microliters/well into several 96-well plates. After 48 hours, 100 microliters of selection media (DMEM containing 10% FBS, HT media supplement (Sigma, St. Louis, Mo.), 0.5 mg/mL xanthine (Sigma, St. Louis, Mo.) and 2.4 micrograms/mL mycophenolic acid (Sigma, St. Louis, Mo.) was applied to each well. Approximately 10 days after initiation of selection, culture supernatants were assayed, by ELISA, for antibody production. Immulon 4 HBX immunoassay plates (ThermoLabsystems, Franklin, Mass.) were coated overnight at 4° C. with 100 microliters/well of 1 microgram/mL of AffiniPure goat anti-human IgG Fcγ-chain specific polyclonal antibodies (Jackson ImmunoResearch Laboratories, Inc., West Grove, Pa.) in 0.2M sodium carbonate-bicarbonate buffer, pH 9.4, washed with Wash Buffer (PBS containing 0.1 % Tween-20), and blocked for 30 minutes at room temperature with 300 microliters/well of SuperBlock Blocking Buffer in TBS (Pierce Biotechnology, Rockford, Ill.). After washing with Wash Buffer, samples containing (hu)AR7BD-33-11A were appropriately diluted in ELISA Buffer (PBS containing 1% BSA and 0.1 % Tween 20) and 100 microliters/well was applied to the ELISA plates. As standards, humanized IgG1, kappa antibody HuAIP12 (Protein Design Labs, Inc.; WO 2004/101511A2) and chimeric IgG2M3, kappa antibody OKT3 (Cole et al., 1997) were used. After incubating the plates for 1.5 hours at room temperature, and washing with Wash Buffer, bound antibodies were detected using 100 microliters/well of a 1:1000 dilution of HRP-conjugated AffiniPure goat anti-human IgG Fcγ-chain specific polyclonal antibodies (Jackson ImmunoResearch Laboratories, Inc., West Grove, Pa.). After incubating for 1 hour at room temperature, and washing with Wash Buffer, color development was performed by adding 100 microliters/well of ABTS Peroxidase Substrate/Peroxidase Solution B (KPL, Inc., Gaithersburg, Md.). After incubating for 4 minutes at room temperature, color development was stopped by adding 100 microliters/well of 2% oxalic acid. Absorbance was read at 415 nm using a VersaMax microplate reader (Molecular Devices Corporation, Sunnyvale, Calif.).

High-yielding Sp2/0 transfectants, Sp2/0-(hu)AR7BD-33-11A-IgG1(V11L)(clone #18) and Sp2/0-(hu)AR7BD-33-11A-IgG2M3(V11L)(clone #5), were expanded in DMEM containing 10% FBS, then adapted and expanded to growth in Protein-Free Basal Medium-2 (PFBM-2) (Protein Design Labs, Inc.; Sauer et al. (2000)) containing 1% low Ig FBS (HyClone, Logan, Utah), supplemented with Protein-Free Feed Medium-3 (PFFM-3) (Protein Design Labs, Inc.; Sauer et al. (2000)), and grown to exhaustion.

To confirm the light and heavy chain mRNA sequences, total RNA was isolated from Sp2/0(hu)AR7BD-33-11A-IgG1(V11L)(clone#18) and Sp2/0-(hu)AR7BD-33-11A-IgG2M3(V11L)(clone #5). First-strand cDNA was synthesized with the Superscript Preamplification System (Invitrogen, Carlsbad, Calif.) using total RNA as a template and random hexadeoxynucleotides as primers. The reaction was performed with SuperScript II reverse transcriptase according to the supplier's protocol. DNA fragments containing the entire coding region of the (hu)AR7BD-33-11A light or heavy chain were amplified by PCR using 5' and 3' primers which bind to the 5' and 3' non-coding regions, respectively. The primer sequences are shown below:

```
5' primer for light chain and
heavy chain:
mbr3 5'-CCATAGAAGACACCGGGACC-3'   (SEQ ID NO:17)

3' primer for light chain:
mc121 5'-AGGTGCAAAGATTCACTT-3'    (SEQ ID NO:18)

3' primer for heavy chain:
mc124 5'-TCCCGTCGCGACCCACG-3'     (SEQ ID NO:19)
```

The amplified fragments were gel-purified and subjected to sequencing with appropriate primers. The determined sequences of the light and heavy chains agreed at every nucleotide position with the known coding sequences of (hu)AR7BD-33-11A-IgG1(V11L) and (hu)AR7BD-33-11A-IgG2M3(V11L)(FIGS. 31, 32 and 33).

A seed bank of ten vials was made by freezing Sp2/0-(hu)AR7BD-33-11A.V11L.G1 (clone #18) and Sp2/0-(hu)AR7BD-33-11A.V11L.G2M3 (clone #5) transfectants in 90% FBS (HyClone, Logan, Utah), 10% DMSO (Sigma, St. Louis, Mo.). Each vial contained approximately $5 \times 10^6$ cells. One vial of each seed bank was thawed and grown in PFBM-2 and the cell culture was sent for mycoplasma testing (Bionique Testing Laboratories, Saranac Lake, N.Y.). The DNA-fluorochrome assay and direct culture methods were negative for mycoplasma contamination.

Figure 34:
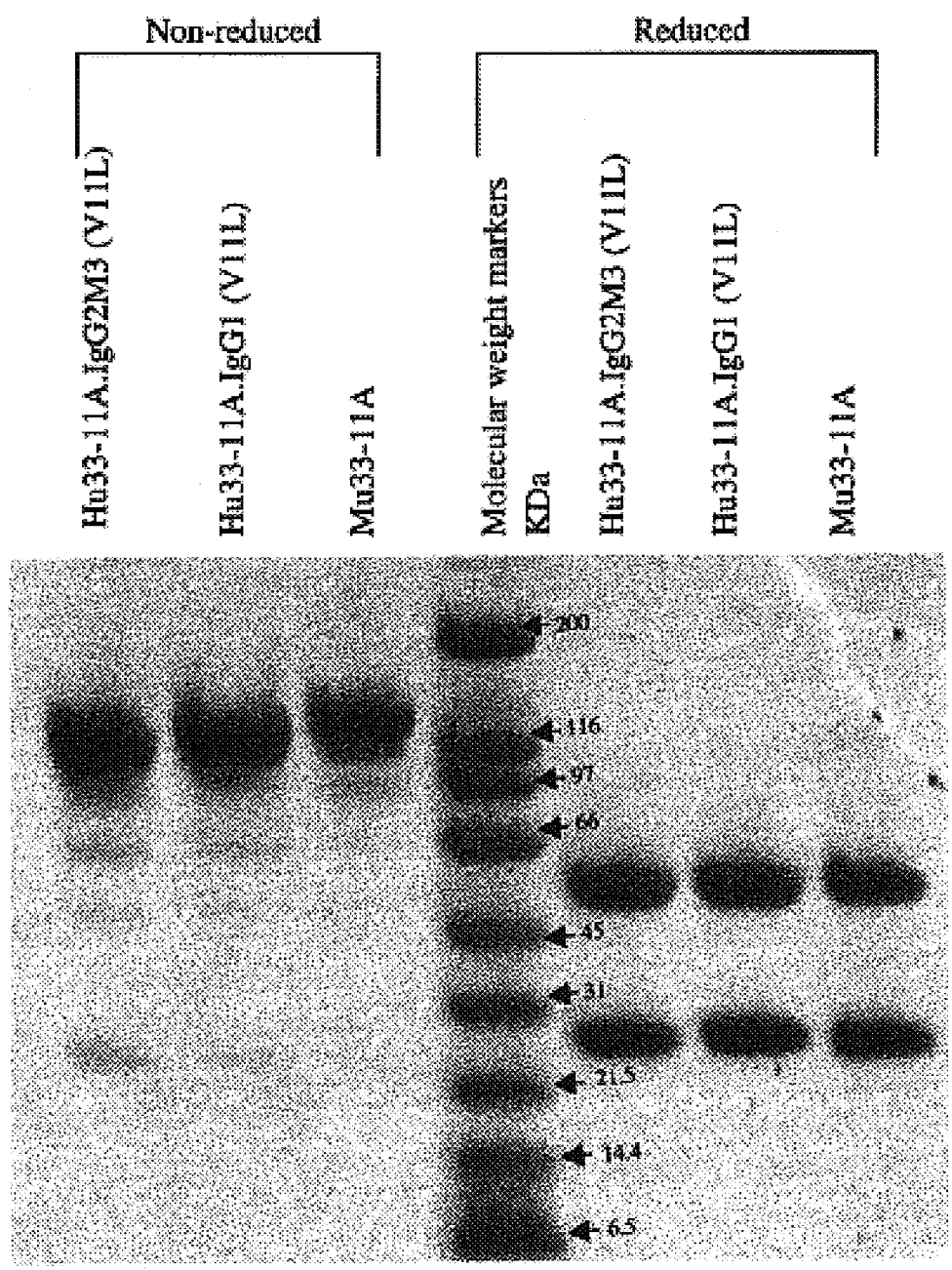
FIG. 34. SDS-PAGE analysis of 7BD-33-11A (Mu33-11A), (hu)AR7BD-33-11A-IgG1(V11L) and (hu)AR7BD-33-11A-IgG2M3(V11L) under non-reducing and reducing conditions as described in the text.
Figure 35:
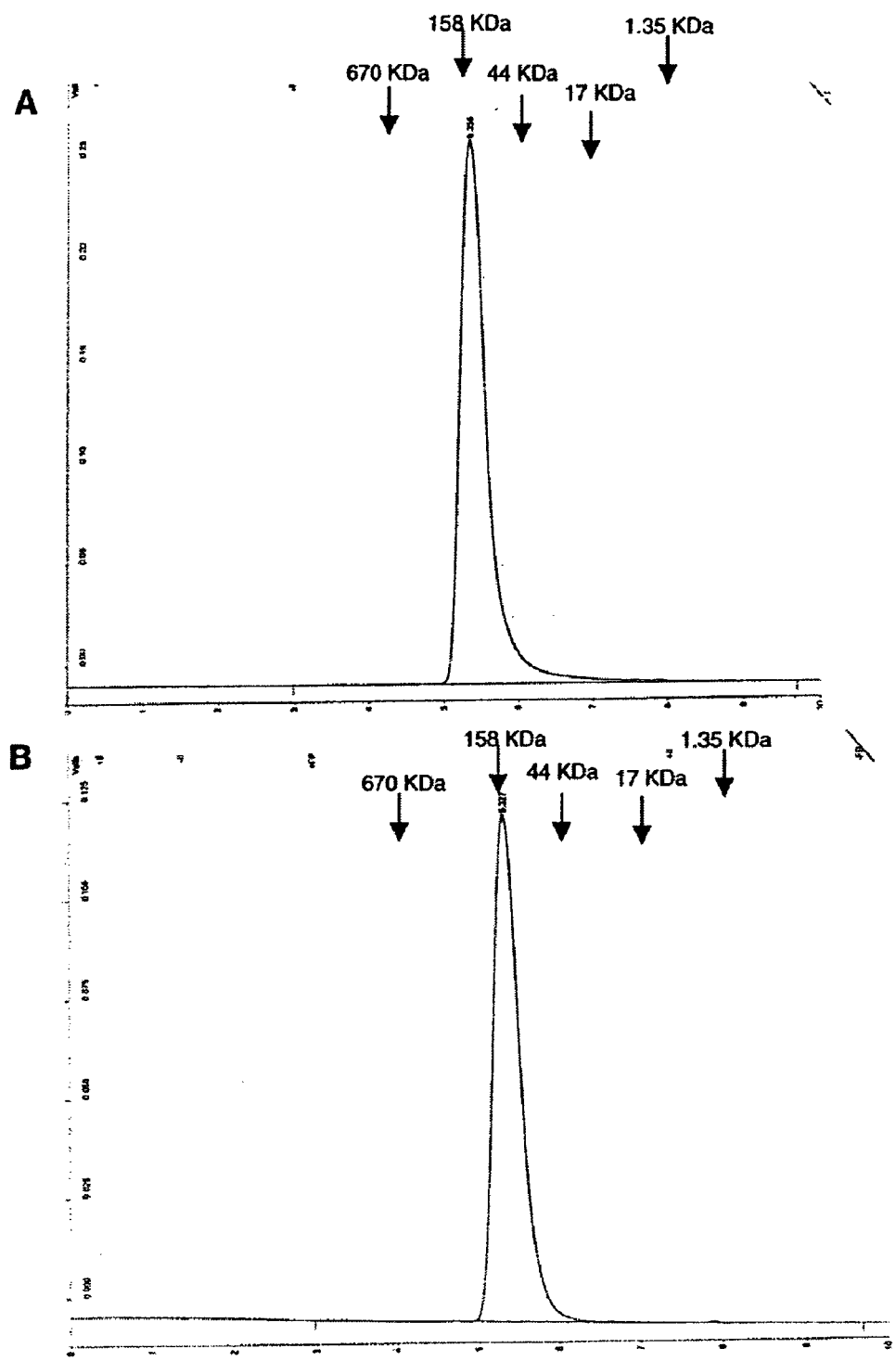
FIG. 35. HPLC analysis of (A) (hu)AR7BD-33-11A-IgG1 (V11L) and (B) (hu)AR7BD-33-11A-IgG2M3 (V11L) by size exclusion chromatography.

Hu)AR7BD-33-11A-IgG1(V11L) and (hu)AR7BD-33-11A-IgG2M3(V11L) antibodies were expressed transiently in 293-H cells or stably in Sp2/0 cells as described below. Sp2/0-(hu)AR7BD-33-11A-IgG1(V11L)(clone #18) and Sp2/0-(hu)AR7BD-33-11AIgG2M3(V11L)(clone #5) were expanded to 0.8 liters in PFBM-2 containing 1% low Ig FBS in roller bottles (400 mL per roller bottle). The (hu)AR7BD-33-11A-IgG1(V11L) and (hu)AR7BD-33-11A-IgG2M3(V11L) monoclonal antibodies were purified from spent culture supernatant by affiinity chromatography on Protein A Sepharose. After centrifugation and filtration, culture supernatant from transient or stable transfectants was loaded onto a HiTrap Protein A HP column (Amersham Biosciences, Piscataway, N.J.). The column was washed with 20 mM Na-Citrate buffer (pH 7.0) containing 150 mM NaCl before the antibody was eluted with 20 mM Na-Citrate buffer (pH 3.5). Eluted pooled fractions were neutralized with 1.5M Na-Citrate buffer (pH 6.5). The protein was dialyzed against PBS and then filtered through a 0.2 micrometer filter prior to storage at 4° C. Antibody concentration was determined by measuring the absorbance at 280 nm (1 mg/mL=$1.4A_{280}$). The yield was 50 mg for (hu)AR7BD-33-11A-IgG1(V11L) and 22 mg for (hu)AR7BD-33-11A-IgG2M3(V11L). Antibodies were then analyzed by SDS-PAGE that was performed according to standard procedures. 7BD-33-11A, (hu)AR7BD-33-11A-IgG1(V11L), and (hu)AR7BD-33-11A-IgG2M3(V11L) antibodies were heated at 70° C. for 10 minutes in the presence and absence of NuPAGE Sample Reducing Agent (Invitrogen, Carlsbad, Calif.) as per the supplier's recommendations for reducing and non-reducing conditions, respectively. Thereafter, antibodies were run on a 4-12% Bis-Tris NuPAGE gel (Invitrogen, Carlsbad, Calif.) for 20 minutes at 200 volts in NuPAGE MES SDS Running buffer (Invitrogen, Carlsbad, Calif.). As protein standards, Broad Range SDS-PAGE standard (BIO-RAD Laboratories, Hercules, Calif.) was run under reducing conditions. The gel was stained overnight at room temperature with SimplyBlue SafeStain (Invitrogen, Carlsbad, Calif.) and then destained overnight at room temperature with $H_2O$. SDS-PAGE analysis (FIG. 34) under nonreducing conditions indicated that the (hu)AR7BD-33-11A(V11L) antibodies have a molecular weight of about 150-160 kDa. Analysis under reducing conditions indicated that the (hu)AR7BD-33-11A(V11L) antibodies are comprised of a heavy chain with a molecular weight of about 50 kDa and a light chain with molecular weight of about 25 kDa. The purity was then analyzed by size exclusion chromatography. Size exclusion HPLC was performed using a Varion HPLC system consisting of a Rainin column heater model CH-1, a Dynamax solvent delivery system model SD200, and a Knaver variable wavelength monitor. Varian Prostar/Dynamax 0.24 system control version 5.51 software was used to control the autosampler, pump, and detector, and to acquire, store, and process the data. Separation was achieved using two TosoHaas TSK-GEL G3000SWXL size exclusion HPLC columns (7.8 mm×300 mm, 5 micrometer particle size, 250 Å pore size; TosoHaas, Montgomeryville, Md.) connected in series. The mobile phase was PBS, pH 7.4, and the flow rate was 1.5 mL/minute. The column eluate was monitored spectrophotometrically at 280 nm. The purity of the antibodies by size exclusion HPLC appeared to be greater than 95% pure (FIG. 35).

Figure 37:
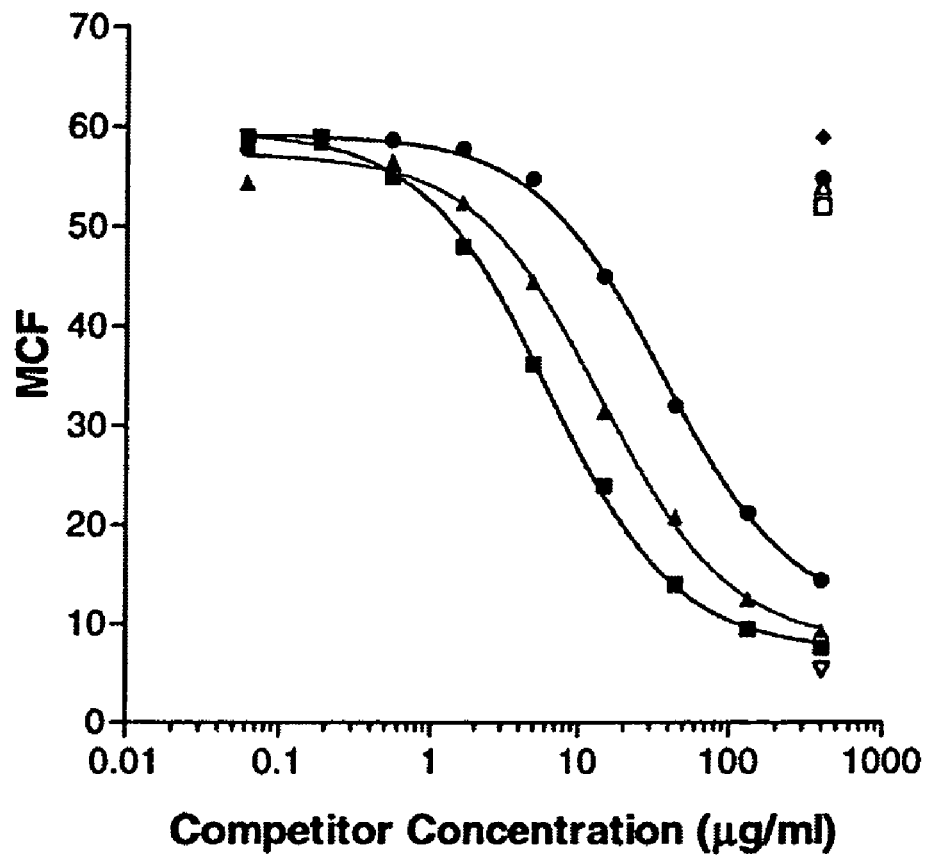
FIG. 37. FACS competition to compare the relative binding affinity to human CD63 between 7BD-33-11A, (hu)AR7BD-33-11A-IgG1(V11L), and (hu)AR7BD-33-11A-IgG2M3 (V11L). The binding of FITC-labeled 7BD-33-11A to human $CD63^+$ PC-3 cells was analyzed in the presence of different amounts of competitor 7BD-33-11A, (hu)AR7BD-33-11A-IgG1(V11L) or (hu)AR7BD-33-11A-IgG2M3(V11L) as described in the text.

The affinity to human CD63 of the (hu)AR7BD-33-11A (V11L) antibodies that had been purified from culture supernatants of stable transfectants was analyzed by the FACS competition method. PC-3 cells were washed three times with sterile PBS (BioWhittaker, Walkersville, Md.). The cells were incubated in HBSS (BioWhittaker, Walkersville, Md.) containing 2.5 mM EDTA media at 37° C. in a $CO_2$ incubator for 5-7 minutes to detach the cells. The cells were washed three times in FACS Staining Buffer (FSB)(PBS containing 0.5% BSA (Sigma, St. Louis, Mo.)) The final wash of the cells was carried out in V-bottom 96-well assay plates (Nalgene Nunc International, Rochester, N.Y.) and the supernatant was discarded. Each well contained $10^5$ cells per test. A mixture of FITC-conjugated 7BD-33-11A (15 micrograms/mL final concentration) and competitor antibody (7BD-33-11A or (hu)AR7BD-33-11A starting at 400 micrograms/mL final concentration and serially diluted 3-fold) in 100 microliters/well was added to the cell pellet in the assay plate and incubated at 4° C. for 1 hour. The cells were washed three times in FSB, and then the pellet was resuspended in 200 microliters of 1% paraformaldehyde solution and analyzed by flow cytometry on a dual laser FACSCalibur flow cytometer (BD Biosciences Immunocytometry Systems, San Jose, Calif.). The 7BD-33-11A, (hu)AR7BD-33-11A-IgG1(V11L) and (hu)AR7BD-33-11A-IgG2M3(V11L) antibodies competed with FITC-conjugated 7BD-33-11A in a concentration-dependent manner. As shown in FIG. 36, the mean $IC_{50}$ values of 7BD-33-11A, (hu)AR7BD-33-11A-IgG1(V11L) and (hu) AR7BD-33-11A-IgG2M3(V11L) obtained using the computer software GraphPad Prism were 6.83 micrograms/mL, 12.7 micrograms/mL and 38.8 micrograms/mL, respectively. A representative result of the FACS competition assay is shown in FIG. 37. The relative binding of (hu)AR7BD-33-11A-IgG1(V11L) and (hu)AR7BD-33-11A-IgG2M3(V11L) to human CD63 was approximately 1.9- and 5.7-fold less than that of 7BD-33-11A. It has been shown previously that the avidity of IgG2 subclass antibodies is 2- to 3-fold lower than that of IgG1 subclass antibodies (Cole et al., 1997; Morelock et al., 1994) and here the same avidity difference was observed between the (hu)AR7BD-33-11A-IgG1(V11L) and (hu)AR7BD-33-11A-IgG2M3(V11L) antibodies. The humanized (hu)AR7BD-33-11A-IgG1(V11L) and (hu) AR7BD-33-11A-IgG2M3(V11L) antibodies are hereafter referred to as (hu)AR7BD-33-11A-IgG1 and (hu)AR7BD-33-11A-IgG2M3 respectively.

EXAMPLE 9

In vivo Tumor Experiments with A2058 Cells

With reference to FIGS. 38 and 39, 4 to 6 week old female SCID mice were implanted with 500,000 human melanoma cells (A2058) in 100 microliters saline injected subcutaneously in the scruff of the neck. The mice were randomly divided into 4 treatment groups of 8 mice/group. On the day after implantation, 2 mg/kg of 7BD-33-11A, (hu)AR7BD-33-11A-IgG1, (hu)AR7BD-33-11A-IgG2M3 test antibodies or buffer control were administered intraperitoneally to each cohort in a volume of 300 microliters after dilution from the stock concentration with a diluent that contained 2.7 mM KCl, 1 mM $KH_2PO_4$, 137 mM NaCl and 20 mM $Na_2HPO_4$. The antibody and control samples were then administered once per week for the duration of the study in the same fashion. Tumor growth was measured about every seventh day with calipers. The group treated with (hu)AR7BD-33-11A-IgG2M3 received a total of 3 doses because of antibody availability. The study was terminated after 34 days, as the animals reached CCAC end-points due to large ulcerated lesions. At this point, the control, 7BD-33-11A, and (hu) AR7BD-33-11A-IgG1 treated groups had received 6 doses. Body weights of the animals were recorded once per week for the duration of the study. At the end of the study all animals were euthanized according to CCAC guidelines.

Figure 38:
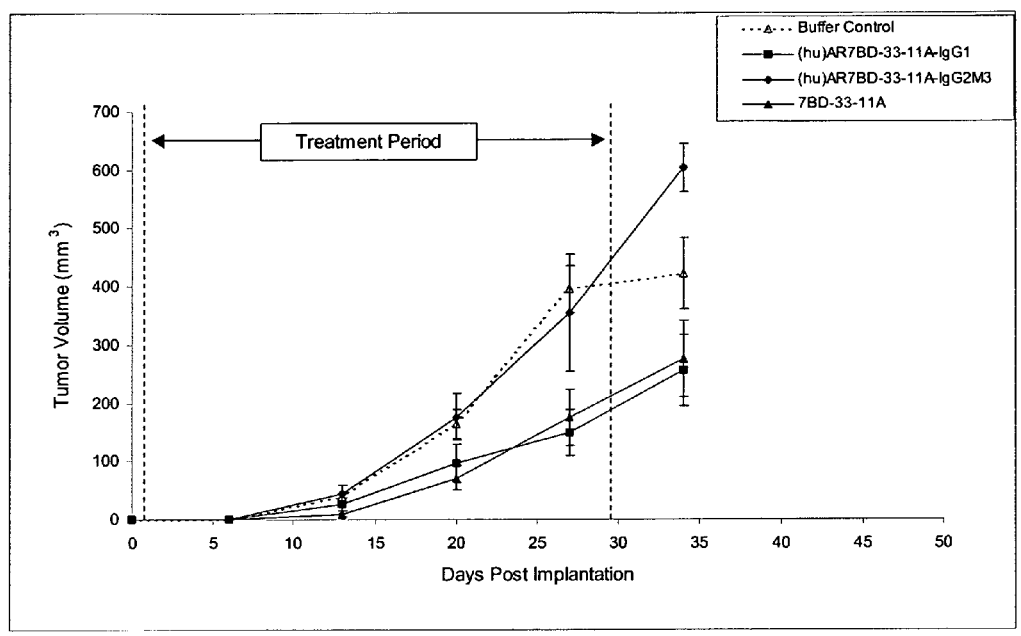
FIG. 38 demonstrates the effect of treatment with 7BD-33-11A, (hu)AR7BD-33-11A-IgG1, and (hu)AR7BD-33-11A-IgG2M3 on tumor growth in a mouse model of human melanoma. Tumor volume is presented as the group mean±SEM. Vertical dashed lines indicate the first and last day of dosing.

Both murine 7BD-33-11A and (hu)AR7BD-33-11A-IgG1 reduced tumor growth in an established A2058 in vivo model of human melanoma cancer. FIG. 38 shows the effect of the 3 antibodies on tumor growth at 2 mg/kg compared to the buffer control. On day 27, when all of the mice in the treatment groups were still alive, 7BD-33-11A decreased tumor growth by 56% (p=0.0086), (hu)AR7BD-33-11A-IgG1 decreased tumor growth by 63% (p=0.0016) and (hu)AR7BD-33-11A-IgG2M3 had no significant effect on tumor growth (10% tumor suppression). These results demonstrate that the humanized IgG1 retains the efficacy of the murine antibody, while the efficacy is markedly decreased in the IgG2M3 version. This observed decrease may be due, at least in part, to the lower number of doses received by the IgG2M3-treatment group, or the lower avidity of the isotype (see above).

Figure 39:
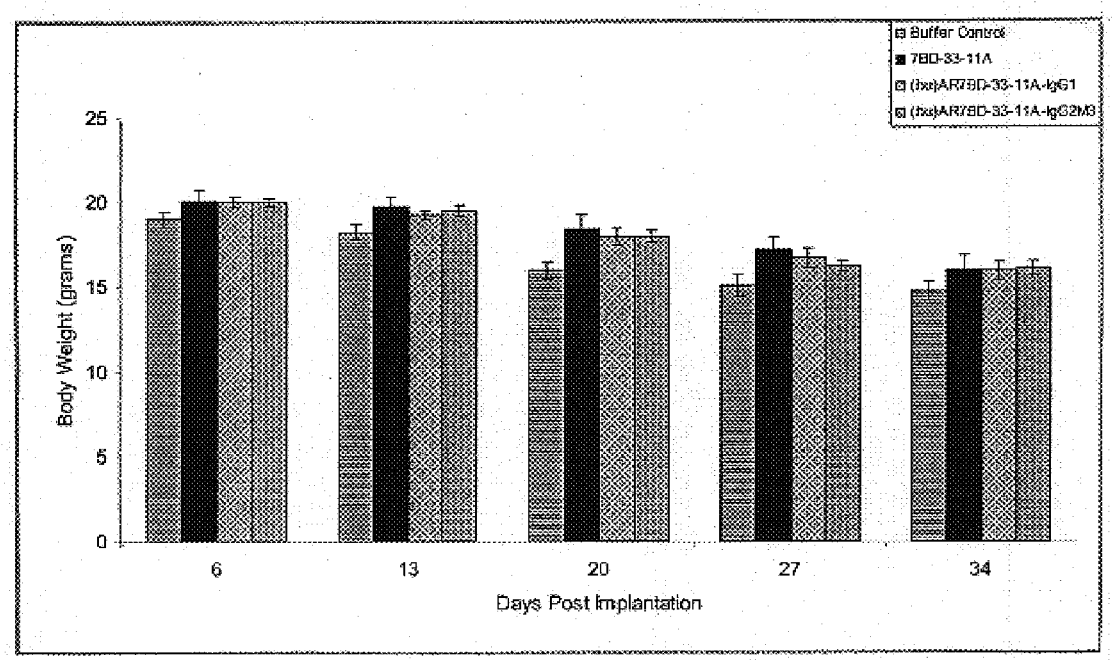
FIG. 39 demonstrates the effect of treatment with monoclonal antibodies on body weight over the duration of the study. Body weight is presented as the group mean±SEM.

There were no clinical signs of toxicity throughout the study. Body weight measured at weekly intervals was a surrogate for well-being and failure to thrive. FIG. 39 presents the results of the body weight of each of the treated groups over the course of the study. There were no significant changes in body weight in mice from any of the antibody-treated groups compared to the buffer control group, at day 27 or at the end of the study (day 34).

In summary, (hu)AR7BD-33-11A-IgG1 demonstrated the same or greater efficacy compared to the murine antibody in the A2058 melanoma model. By contrast, the (hu)AR7BD-33-11A-IgG2M3 chimeric antibody did not reduce tumor growth in this model of human A2058 melanoma. In addition, the murine and humanized antibodies appreared to be well-tolerated by the mice.

EXAMPLE 10

Determination of the Binding Affinity of the 7BD-33-11A, 1A245.6 H460-22-1, (hu)AR7BD-33-11A-IgG1 and (hu) AR7BD-33-11A-IgG2M3 to CD63

The binding affinity of 7BD-33-11A, 1A245.6, H460-22-1, and of (hu)AR7BD-33-11A-IgG1 and (hu)AR7BD-33-11A-IgG2M3, was compared by determination of the respective dissociation constants after binding to the bacteria-expressed and purified recombinant protein GST-fusion construct of the extracellular domain 2 (GST-EC2) of human CD63.

An anti-GST antibody was immobilized using the standard amine coupling procedure. The surface of a CM5 sensor chip (Biacore, Uppsala, Sweden) was activated by the injection of 35 mL of a mixture containing 0.05 M NHS and 0.2 M EDC in $H_2O$. The anti-GST antibody was injected at a concentration of 30 mg/mL in 10 mM sodium acetate pH5.0 until 50,000 RU to 100,000 RU was captured. Finally, 35 mL of 1.0 M ethanolamine-HCl, pH 8.5, was injected to block any activated sites on the sensor chip surface. GST-EC2 (25 mL) was injected at 5 mg/mL followed by a 25-50 mL injection of the antibody. Regeneration of the sensor chip surface for subsequent injections was accomplished by application of two 10 mL pulses of 20 mM glycine pH 2.2. Antibodies were serially injected at concentration ranging from 12.5 to 200 nM. As a control, each antibody concentration was injected over a surface where GST, instead of GST-EC2, was captured. The affinity of the different antibodies for the EC2 was calculated from the measured steady state binding levels. For each sensorgram, a report point was taken 20 seconds before the end of the antibody injection (Req). For each antibody concentration, the Req obtained when antibody was injected over GST was subtracted from the Req obtained when the antibody was injected over the GST-EC2. The slope of a plot of Req/Conc vs. Req was determined and it represented the association constant (KA). The dissociation constant (KD) was calculated as the reciprocal of KA. The experiments were carried out using a Biacore 2000 system (Biacore, Uppsala, Sweden). This experiment yielded the values of 135 nM, 42 nM and 10 nM for 7BD-33-11A, H460-22-1 and 1A245.6, respectively (FIG. 40), therefore indicating that 7BD-33-11A has the lowest affinity of those used in this study. It also indicates that the affinities of the humanized antibodies (hu)AR7BD-33-11A-IgG1 and (hu)AR7BD-33-11A-IgG2M3 are higher than that of the parental murine 7BD-33-11A. These results are different than those reported in Example 8. The differences in the results may be due, in part, to the following. First of all, different methodologies were used, FACS versus surface plasmon resonsance. Also, in Example 8, PC-3 cells were used whereas in Example 10, bacterially expressed recombinant CD63 was used. These two sources might represent slightly different conformational or glycosylated forms of CD63.

The preponderance of evidence shows that AR51A994.1, 7BDI-58, 7BDI-60, H460-22-1, 7BD-33-11A, (hu)AR7BD- 33-11A-IgG1 and 1A245.6 mediate anti-cancer effects through ligation of epitopes present on CD63. It has been shown, in Example 4, AR51A994.1, 7BDI-58, 7BDI-60 and 7BD-33-11A antibody can be used to immunoprecipitate the cognate antigen from expressing cells such as MDA-MB-231 cells. Further it could be shown that the AR51A994.1, 7BDI-58, 7BDI-60, 7BD-33-11A, (hu)AR7BD-33-11A-IgG1 and (hu)AR7BD-33-11A-IgG2M3 antibody could be used in detection of cells and/or tissues which express a CD63 antigenic moiety which specifically binds thereto, utilizing techniques illustrated by, but not limited to FACS, cell ELISA or IHC.

Thus, it could be shown that the immunoprecipitated AR51A994.1, 7BDI-58, 7BDI-60 and 7BD-33-11A antigen can inhibit the binding of either antibody to such cells or tissues using FACS, cell ELISA or IHC assays. Further, as with the AR51A994.1, 7BDI-58, 7BDI-60 and 7BD-33-11A antibody, other anti-CD63 antibodies could be used to immunoprecipitate and isolate other forms of the CD63 antigen, and the antigen can also be used to inhibit the binding of those antibodies to the cells or tissues that express the antigen using the same types of assays.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objects and obtain the ends and advantages mentioned, as well as those inherent therein. Any oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

---

What is claimed is:

1. An isolated monoclonal antibody produced by the hybridoma deposited with the IDAC as accession number 141205-06 or an antigen binding fragment thereof wherein the monoclonal antibody or antigen binding fragment thereof binds CD63.

2. A humanized version of the isolated monoclonal antibody of claim 1, or antigen binding fragment thereof wherein the humanized version of the monoclonal antibody or antigen binding fragment thereof binds CD63.

3. A chimeric version of the isolated monoclonal antibody of claim 1, or antigen binding fragment thereof wherein the chimeric version of the monoclonal antibody or antigen binding fragment thereof binds CD63.

4. The isolated clone deposited with the IDAC as accession number 141205-06.

5. The isolated antibody or antigen binding fragment of any one of claims 1, 2, or 3 conjugated with a member selected from the group consisting of cytotoxic moieties, enzymes, radioactive compounds, and hematogenous cells.

* * * * *

SEQUENCE LISTING

```
<160> NUMBER OF SEQ ID NOS: 66

<210> SEQ ID NO 1
<211> LENGTH: 396
<212> TYPE: DNA
<213> ORGANISM: mouse

<400> SEQUENCE: 1
atggaatcac agactcaggt cttcctctcc ctgctgctct gggtatctgg tacctgtggg      60
aacattatga tgacacagtc gccatcatct ctggctgtgt ctgcaggaga aaaggtcact     120
atgagctgta agtccagtca aagtgtttta tacagttcaa atcagaaaaa ctacttggcc     180
tggtaccagc agaaaccagg gcagtctcct aaactgctga tctactgggc atccactagg     240
gaatctggtg tccctgatcg cttcacaggc agtggatctg ggacagattt tactcttacc     300
atcagcagtg tacaagctga agacctggca gtttattact gtcatcaata tttctcctcg     360
tacacgttcg gaggggggac caagctggaa ataaaa                               396

<210> SEQ ID NO 2
<211> LENGTH: 132
<212> TYPE: PRT
<213> ORGANISM: mouse

<400> SEQUENCE: 2

Met Glu Ser Gln Thr Gln Val Phe Leu Ser Leu Leu Leu Trp Val Ser
 1               5                  10                  15

Gly Thr Cys Gly Asn Ile Met Met Thr Gln Ser Pro Ser Ser Leu Ala
             20                  25                  30

Val Ser Ala Gly Glu Lys Val Thr Met Ser Cys Lys Ser Ser Gln Ser
         35                  40                  45

Val Leu Tyr Ser Ser Asn Gln Lys Asn Tyr Leu Ala Trp Tyr Gln Gln
     50                  55                  60
```

-continued

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys His Gln Tyr Phe Ser Ser Tyr Thr Phe Gly Gly Gly Thr Lys
        115                 120                 125

Leu Glu Ile Lys
        130

<210> SEQ ID NO 3
<211> LENGTH: 414
<212> TYPE: DNA
<213> ORGANISM: mouse

<400> SEQUENCE: 3
atggaatgga gttggatatt tctctttctc ctgtcaggaa ctgcaggtgt ccactctgag      60
gtccagctgc agcagtctgg acctgggctg gtaaagcctg ggcttcagt gaagatgtcc     120
tgcaaggctt ctggatacac attcactagt tatgttatgc actgggtgaa gcagatgcct    180
gggcagggcc ttgagtggat tggatatatt actccttata atgatggtac taaatacaat    240
gagaagttca aggcaaggc cacactgact tcagacaaat cctccagcac agcctacatg    300
gacctcagca gcctgacctc tgaggactct gcggtctatt actgtgtcta cggtagtaga    360
tacgactggt acttcgatgt ctggggcgca gggaccacgg tcaccgtctc ctca         414

<210> SEQ ID NO 4
<211> LENGTH: 138
<212> TYPE: PRT
<213> ORGANISM: mouse

<400> SEQUENCE: 4

Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Gly Leu Val Lys
            20                  25                  30

Pro Gly Ala Ser Val Lys Met Ser Cys Lys Ala Ser Gly Tyr Thr Phe
        35                  40                  45

Thr Ser Tyr Val Met His Trp Val Lys Gln Met Pro Gly Gln Gly Leu
    50                  55                  60

Glu Trp Ile Gly Tyr Ile Thr Pro Tyr Asn Asp Gly Thr Lys Tyr Asn
65                  70                  75                  80

Glu Lys Phe Lys Gly Lys Ala Thr Leu Thr Ser Asp Lys Ser Ser Ser
                85                  90                  95

Thr Ala Tyr Met Asp Leu Ser Ser Leu Thr Ser Glu Asp Ser Ala Val
            100                 105                 110

Tyr Tyr Cys Val Tyr Gly Ser Arg Tyr Asp Trp Tyr Phe Asp Val Trp
        115                 120                 125

Gly Ala Gly Thr Thr Val Thr Val Ser Ser
        130                 135

<210> SEQ ID NO 5
<211> LENGTH: 433
<212> TYPE: DNA
<213> ORGANISM: Artificial
<220> FEATURE:

<223> OTHER INFORMATION: humanized light chain, variable region

<400> SEQUENCE: 5

```
acgcgtccac catggatttt caagtgcaga ttttcagctt cctgctaatc agtgcctcag      60
tcataatatc cagaggagac attgtgatga cacagtcgcc agactctctg gctgtgtctc     120
taggagaaag ggccactatc agctgcaagt ccagtcaaag tgttttatac agttcaaatc     180
agaaaaacta cttggcctgg taccagcaga accagggca gcctcctaaa ctgctgatct      240
actgggcatc cactagggaa tctggtgtcc ctgatcgctt ctcaggcagt ggatctggga     300
cagattttac tcttaccatc agcagtctac aagctgaaga cgtggcagtt tattactgtc     360
atcaatattt ctcctcgtac acgttcggac aggggaccaa gctggaaata aaacgtaagt     420
acttttttct aga                                                        433
```

<210> SEQ ID NO 6
<211> LENGTH: 134
<212> TYPE: PRT
<213> ORGANISM: Artificial
<220> FEATURE:
<223> OTHER INFORMATION: humanized light chain, variable region

<400> SEQUENCE: 6

```
Met Asp Phe Gln Val Gln Ile Phe Ser Phe Leu Leu Ile Ser Ala Ser
1               5                   10                  15
Val Ile Ile Ser Arg Gly Asp Ile Val Met Thr Gln Ser Pro Asp Ser
            20                  25                  30
Leu Ala Val Ser Leu Gly Glu Arg Ala Thr Ile Ser Cys Lys Ser Ser
        35                  40                  45
Gln Ser Val Leu Tyr Ser Ser Asn Gln Lys Asn Tyr Leu Ala Trp Tyr
    50                  55                  60
Gln Gln Lys Pro Gly Gln Pro Pro Lys Leu Leu Ile Tyr Trp Ala Ser
65                  70                  75                  80
Thr Arg Glu Ser Gly Val Pro Asp Arg Phe Ser Gly Ser Gly Ser Gly
                85                  90                  95
Thr Asp Phe Thr Leu Thr Ile Ser Ser Leu Gln Ala Glu Asp Val Ala
            100                 105                 110
Val Tyr Tyr Cys His Gln Tyr Phe Ser Ser Tyr Thr Phe Gly Gln Gly
        115                 120                 125
Thr Lys Leu Glu Ile Lys
    130
```

<210> SEQ ID NO 7
<211> LENGTH: 446
<212> TYPE: DNA
<213> ORGANISM: Artificial
<220> FEATURE:
<223> OTHER INFORMATION: humanized heavy chain, variable region

<400> SEQUENCE: 7

```
acgcgtccac catggactcc aggctcaatt tagttttcct tgtccttatt ttaaaaggtg      60
tccagtgtga ggtccagctg gtgcagtctg gagctgagct gaaaaagcct ggggctacag     120
tgaagatctc ctgcaaggtc tctggataca cattcactag ttatgttatg cactgggtta     180
ggcaggcgcc tgggaagggc cttgagtgga ttggatatat tactcgttat aatgatggta     240
ctaaatacaa tgagaagttc aaaggcaagg ccacactgac ttcagacaaa tccaccgaca     300
cagcctacat ggaactcagc agcctgcgct ctgaggacac tgcggtctat tactgtgtct     360
```

```
acggtagtag atacgactgg tacttcgatg tctggggcca agggaccacc gtcaccgtct    420
cctcaggtaa gaatggccac tctaga                                         446
```

<210> SEQ ID NO 8
<211> LENGTH: 138
<212> TYPE: PRT
<213> ORGANISM: Artificial
<220> FEATURE:
<223> OTHER INFORMATION: humanized heavy chain, variable region

<400> SEQUENCE: 8

```
Met Asp Ser Arg Leu Asn Leu Val Phe Leu Val Leu Ile Leu Lys Gly
1               5                   10                  15

Val Gln Cys Glu Val Gln Leu Val Gln Ser Gly Ala Glu Leu Lys Lys
            20                  25                  30

Pro Gly Ala Thr Val Lys Ile Ser Cys Lys Val Ser Gly Tyr Thr Phe
        35                  40                  45

Thr Ser Tyr Val Met His Trp Val Arg Gln Ala Pro Gly Lys Gly Leu
    50                  55                  60

Glu Trp Ile Gly Tyr Ile Thr Pro Tyr Asn Asp Gly Thr Lys Tyr Asn
65                  70                  75                  80

Glu Lys Phe Lys Gly Lys Ala Thr Leu Thr Ser Asp Lys Ser Thr Asp
                85                  90                  95

Thr Ala Tyr Met Glu Leu Ser Ser Leu Arg Ser Glu Asp Thr Ala Val
            100                 105                 110

Tyr Tyr Cys Val Tyr Gly Ser Arg Tyr Asp Trp Tyr Phe Asp Val Trp
        115                 120                 125

Gly Gln Gly Thr Thr Val Thr Val Ser Ser
    130                 135
```

<210> SEQ ID NO 9
<211> LENGTH: 726
<212> TYPE: DNA
<213> ORGANISM: Artificial
<220> FEATURE:
<223> OTHER INFORMATION: humanized kappa light chain

<400> SEQUENCE: 9

```
atggattttc aagtgcagat tttcagcttc ctgctaatca gtgcctcagt cataatatcc    60
agaggagaca ttgtgatgac acagtcgcca gactctctgg ctgtgtctct aggagaaagg   120
gccactatca gctgcaagtc cagtcaaagt gttttataca gttcaaatca gaaaaactac   180
ttggcctggt accagcagaa accagggcag cctcctaaac tgctgatcta ctgggcatcc   240
actagggaat ctggtgtccc tgatcgcttc tcaggcagtg gatctgggac agatttttact   300 cttaccatca gcagtctaca agctgaagac gtggcagttt attactgtca tcaatatttc   360
tcctcgtaca cgttcggaca ggggaccaag ctggaaataa aacgtactgt ggctgcacca   420
tctgtcttca tcttcccgcc atctgatgag cagttgaaat ctggaactgc ctctgttgtg   480
tgcctgctga ataacttcta tcccagagag gccaaagtac agtggaaggt ggataacgcc   540
ctccaatcgg gtaactccca ggagagtgtc acagagcagg acagcaagga cagcacctac   600
agcctcagca gcaccctgac gctgagcaaa gcagactacg agaaacacaa agtctacgcc   660
tgcgaagtca cccatcaggg cctgagctcg cccgtcacaa agagcttcaa caggggagag   720
tgttag                                                              726
```

<210> SEQ ID NO 10

<211> LENGTH: 241
<212> TYPE: PRT
<213> ORGANISM: Artificial
<220> FEATURE:
<223> OTHER INFORMATION: humanized kappa light chain

<400> SEQUENCE: 10

```
Met Asp Phe Gln Val Gln Ile Phe Ser Phe Leu Leu Ile Ser Ala Ser
1               5                   10                  15

Val Ile Ile Ser Arg Gly Asp Ile Val Met Thr Gln Ser Pro Asp Ser
            20                  25                  30

Leu Ala Val Ser Leu Gly Glu Arg Ala Thr Ile Ser Cys Lys Ser Ser
        35                  40                  45

Gln Ser Val Leu Tyr Ser Ser Asn Gln Lys Asn Tyr Leu Ala Trp Tyr
    50                  55                  60

Gln Gln Lys Pro Gly Gln Pro Pro Lys Leu Leu Ile Tyr Trp Ala Ser
65                  70                  75                  80

Thr Arg Glu Ser Gly Val Pro Asp Arg Phe Ser Gly Ser Gly Ser Gly
                85                  90                  95

Thr Asp Phe Thr Leu Thr Ile Ser Ser Leu Gln Ala Glu Asp Val Ala
            100                 105                 110

Val Tyr Tyr Cys His Gln Tyr Phe Ser Ser Tyr Thr Phe Gly Gln Gly
        115                 120                 125

Thr Lys Leu Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys
```

<210> SEQ ID NO 11
<211> LENGTH: 1404
<212> TYPE: DNA
<213> ORGANISM: Artificial
<220> FEATURE:
<223> OTHER INFORMATION: humanized heavy chain (V11L)

<400> SEQUENCE: 11

```
atggactcca ggctcaattt agtttttcctt gtccttattt taaaggtgt ccagtgtgag      60 gtccagctgg tgcagtctgg agctgagctg aaaaagcctg ggctacagt gaagatctcc     120 tgcaaggtct ctggatacac attcactagt tatgttatgc actgggttag gcaggcgcct     180
gggaagggcc ttgagtggat tggatatatt actccttata atgatggtac taaatacaat     240
gagaagttca aggcaaggc cacactgact tcagacaaat ccaccgacac agcctacatg      300
gaactcagca gcctgcgctc tgaggacact gcggtctatt actgtgtcta cggtagtaga     360
tacgactggt acttcgatgt ctggggccaa gggaccaccg tcaccgtctc ctcagcctcc     420
```

-continued

```
accaagggcc catcggtctt ccccctggca ccctcctcca agagcacctc tgggggcaca    480
gcggccctgg gctgcctggt caaggactac ttccccgaac cggtgacggt gtcgtggaac    540
tcaggcgccc tgaccagcgg cgtgcacacc ttcccggctg tcctacagtc ctcaggactc    600
tactccctca gcagcgtggt gaccgtgccc tccagcagct tgggcaccca gacctacatc    660
tgcaacgtga atcacaagcc cagcaacaag gtggacaaga agttgagcc caaatcttgt     720 gacaaaactc acacatgccc accgtgccca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggatga gctgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca agagcaggtg gcagcagggg   1320
aacgtcttct catgctccgt gatgcatgag gctctgcaca accactacac gcagaagagc   1380
ctctccctgt ctccgggtaa atga                                          1404
```

<210> SEQ ID NO 12
<211> LENGTH: 468
<212> TYPE: PRT
<213> ORGANISM: Artificial
<220> FEATURE:
<223> OTHER INFORMATION: humanized heavy chain (V11L)

<400> SEQUENCE: 12

```
Met Asp Ser Arg Leu Asn Leu Val Phe Leu Val Leu Ile Leu Lys Gly
1               5                   10                  15

Val Gln Cys Glu Val Gln Leu Val Gln Ser Gly Ala Glu Leu Lys Lys
            20                  25                  30

Pro Gly Ala Thr Val Lys Ile Ser Cys Lys Val Ser Gly Tyr Thr Phe
        35                  40                  45

Thr Ser Tyr Val Met His Trp Val Arg Gln Ala Pro Gly Lys Gly Leu
    50                  55                  60

Glu Trp Ile Gly Tyr Ile Thr Pro Tyr Asn Asp Gly Thr Lys Tyr Asn
65                  70                  75                  80

Glu Lys Phe Lys Gly Lys Ala Thr Leu Thr Ser Asp Lys Ser Thr Asp
                85                  90                  95

Thr Ala Tyr Met Glu Leu Ser Ser Leu Arg Ser Glu Asp Thr Ala Val
            100                 105                 110

Tyr Tyr Cys Val Tyr Gly Ser Arg Tyr Asp Trp Tyr Phe Asp Val Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190
```

Ala Val Leu Gln Ser Ser Gly Leu Tyr Ser Leu Ser Val Val Thr
          195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 13
<211> LENGTH: 1395
<212> TYPE: DNA
<213> ORGANISM: Artificial
<220> FEATURE:
<223> OTHER INFORMATION: humanized heavy chain (V11L M3)

<400> SEQUENCE: 13
atggactcca ggctcaattt agttttcctt gtccttattt taaaaggtgt ccagtgtgag      60
gtccagctgg tgcagtctgg agctgagctg aaaaagcctg ggctacagt gaagatctcc     120 tgcaaggtct ctggatacac attcactagt tatgttatgc actgggttag gcaggcgcct     180
gggaagggcc ttgagtggat tggatatatt actccttata atgatggtac taaatacaat     240
gagaagttca aaggcaaggc cacactgact tcagacaaat ccaccgacac agcctacatg     300
gaactcagca gcctgcgctc tgaggacact gcggtctatt actgtgtcta cggtagtaga     360
tacgactggt acttcgatgt ctggggccaa gggaccacg tcaccgtctc ctcagcctcc     420

-continued

| | |
|---|---|
| accaagggcc catcggtctt ccccctggcg ccctgctcca ggagcacctc cgagagcaca | 480 |
| gcggccctgg gctgcctggt caaggactac ttccccgaac cggtgacggt gtcgtggaac | 540 |
| tcaggcgctc tgaccagcgg cgtgcacacc ttcccagctg tcctacagtc ctcaggactc | 600 |
| tactccctca gcagcgtggt gaccgtgccc tccagcaact tcggcaccca gacctacacc | 660 |
| tgcaacgtag atcacaagcc cagcaacacc aaggtggaca agacagttga gcgcaaatgt | 720 |
| tgtgtcgagt gcccaccgtg cccagcacca cctgcggcag caccgtcagt cttcctcttc | 780 |
| cccccaaaac ccaaggacac cctcatgatc tcccggaccc ctgaggtcac gtgcgtggtg | 840 |
| gtggacgtga gccacgaaga ccccgaggtc cagttcaact ggtacgtgga cggcgtggag | 900 |
| gtgcataatg ccaagacaaa gccacgggag gagcagttca acagcacgtt ccgtgtggtc | 960 |
| agcgtcctca ccgttgtgca ccaggactgg ctgaacggca aggagtacaa gtgcaaggtc | 1020 |
| tccaacaaag gcctcccagc ccccatcgag aaaaccatct ccaaaaccaa agggcagccc | 1080 |
| cgagaaccac aggtgtacac cctgccccca tcccgggagg agatgaccaa gaaccaggtc | 1140 |
| agcctgacct gcctggtcaa aggcttctac cccagcgaca tcgccgtgga gtgggagagc | 1200 |
| aatgggcagc cggagaacaa ctacaagacc acacctccca tgctggactc cgacggctcc | 1260 |
| ttcttcctct acagcaagct caccgtggac aagagcaggt ggcagcaggg gaacgtcttc | 1320 |
| tcatgctccg tgatgcatga ggctctgcac aaccactaca cgcagaagag cctctccctg | 1380 |
| tctccgggta aatga | 1395 |

<210> SEQ ID NO 14
<211> LENGTH: 464
<212> TYPE: PRT
<213> ORGANISM: Artificial
<220> FEATURE:
<223> OTHER INFORMATION: humanized heavy chain (V11L M3)

<400> SEQUENCE: 14

Met Asp Ser Arg Leu Asn Leu Val Phe Leu Val Leu Ile Leu Lys Gly
1               5                   10                  15

Val Gln Cys Glu Val Gln Leu Val Gln Ser Gly Ala Glu Leu Lys Lys
            20                  25                  30

Pro Gly Ala Thr Val Lys Ile Ser Cys Lys Val Ser Gly Tyr Thr Phe
        35                  40                  45

Thr Ser Tyr Val Met His Trp Val Arg Gln Ala Pro Gly Lys Gly Leu
    50                  55                  60

Glu Trp Ile Gly Tyr Ile Thr Pro Tyr Asn Asp Gly Thr Lys Tyr Asn
65                  70                  75                  80

Glu Lys Phe Lys Gly Lys Ala Thr Leu Thr Ser Asp Lys Ser Thr Asp
                85                  90                  95

Thr Ala Tyr Met Glu Leu Ser Ser Leu Arg Ser Glu Asp Thr Ala Val
            100                 105                 110

Tyr Tyr Cys Val Tyr Gly Ser Arg Tyr Asp Trp Tyr Phe Asp Val Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

```
Ala Val Leu Gln Ser Ser Gly Leu Tyr Ser Leu Ser Ser Val Val Thr
            195                 200                 205

Val Pro Ser Ser Asn Phe Gly Thr Gln Thr Tyr Thr Cys Asn Val Asp
        210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Ala Ala Ala Pro Ser
            245                 250                 255

Val Phe Leu Phe Pro Pro Lys Pro Lys Asp Thr Leu Met Ile Ser Arg
        260                 265                 270

Thr Pro Glu Val Thr Cys Val Val Asp Val Ser His Glu Asp Pro
            275                 280                 285

Glu Val Gln Phe Asn Trp Tyr Val Asp Gly Val Glu Val His Asn Ala
        290                 295                 300

Lys Thr Lys Pro Arg Glu Glu Gln Phe Asn Ser Thr Phe Arg Val Val
305                 310                 315                 320

Ser Val Leu Thr Val Val His Gln Asp Trp Leu Asn Gly Lys Glu Tyr
            325                 330                 335

Lys Cys Lys Val Ser Asn Lys Gly Leu Pro Ala Pro Ile Glu Lys Thr
            340                 345                 350

Ile Ser Lys Thr Lys Gly Gln Pro Arg Glu Pro Gln Val Tyr Thr Leu
            355                 360                 365

Pro Pro Ser Arg Glu Glu Met Thr Lys Asn Gln Val Ser Leu Thr Cys
        370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
        450                 455                 460

<210> SEQ ID NO 15
<211> LENGTH: 20
<212> TYPE: DNA
<213> ORGANISM: Artificial
<220> FEATURE:
<223> OTHER INFORMATION: primer for PCR

<400> SEQUENCE: 15
gccagtggat agaccgatgg                                                   20

<210> SEQ ID NO 16
<211> LENGTH: 21
<212> TYPE: DNA
<213> ORGANISM: Artificial
<220> FEATURE:
<223> OTHER INFORMATION: primer for PCR

<400> SEQUENCE: 16
gatggataca gttggtgcag c                                                 21

<210> SEQ ID NO 17
<211> LENGTH: 20
```

<210> SEQ ID NO 17
<211> LENGTH: 20
<212> TYPE: DNA
<213> ORGANISM: Artificial
<220> FEATURE:
<223> OTHER INFORMATION: primer for PCR

<400> SEQUENCE: 17
ccatagaaga caccgggacc                                              20

<210> SEQ ID NO 18
<211> LENGTH: 18
<212> TYPE: DNA
<213> ORGANISM: Artificial
<220> FEATURE:
<223> OTHER INFORMATION: primer for PCR

<400> SEQUENCE: 18
aggtgcaaag attcactt                                                18

<210> SEQ ID NO 19
<211> LENGTH: 17
<212> TYPE: DNA
<213> ORGANISM: Artificial
<220> FEATURE:
<223> OTHER INFORMATION: primer for PCR

<400> SEQUENCE: 19
tcccgtcgcg acccacg                                                 17

<210> SEQ ID NO 20
<211> LENGTH: 40
<212> TYPE: DNA
<213> ORGANISM: Artificial
<220> FEATURE:
<223> OTHER INFORMATION: primer for PCR

<400> SEQUENCE: 20
tataacgcgt ccaccatgga ttttcaagtg cagattttca                        40

<210> SEQ ID NO 21
<211> LENGTH: 40
<212> TYPE: DNA
<213> ORGANISM: Artificial
<220> FEATURE:
<223> OTHER INFORMATION: primer for PCR

<400> SEQUENCE: 21
ggcactgatt agcaggaagc tgaaaatctg cacttgaaaa                        40

<210> SEQ ID NO 22
<211> LENGTH: 40
<212> TYPE: DNA
<213> ORGANISM: Artificial
<220> FEATURE:
<223> OTHER INFORMATION: primer for PCR

<400> SEQUENCE: 22
gcttcctgct aatcagtgcc tcagtcataa tatccagagg                        40

<210> SEQ ID NO 23
<211> LENGTH: 40
<212> TYPE: DNA
<213> ORGANISM: Artificial
<220> FEATURE:
<223> OTHER INFORMATION: primer for PCR

<400> SEQUENCE: 23
actgtgtcat cacaatgtct cctctggata ttatgactga                              40

<210> SEQ ID NO 24
<211> LENGTH: 40
<212> TYPE: DNA
<213> ORGANISM: Artificial
<220> FEATURE:
<223> OTHER INFORMATION: primer for PCR

<400> SEQUENCE: 24
agacattgtg atgacacagt cgccagactc tctggctgtg                              40

<210> SEQ ID NO 25
<211> LENGTH: 40
<212> TYPE: DNA
<213> ORGANISM: Artificial
<220> FEATURE:
<223> OTHER INFORMATION: primer for PCR

<400> SEQUENCE: 25
gtggcccttt ctcctagaga cacagccaga gagtctggcg                              40

<210> SEQ ID NO 26
<211> LENGTH: 40
<212> TYPE: DNA
<213> ORGANISM: Artificial
<220> FEATURE:
<223> OTHER INFORMATION: primer for PCR

<400> SEQUENCE: 26
tctctaggag aaagggccac tatcagctgc aagtccagtc                              40

<210> SEQ ID NO 27
<211> LENGTH: 40
<212> TYPE: DNA
<213> ORGANISM: Artificial
<220> FEATURE:
<223> OTHER INFORMATION: primer for PCR

<400> SEQUENCE: 27
tgaactgtat aaaacacttt gactggactt gcagctgata                              40

<210> SEQ ID NO 28
<211> LENGTH: 40
<212> TYPE: DNA
<213> ORGANISM: Artificial
<220> FEATURE:
<223> OTHER INFORMATION: primer for PCR

<400> SEQUENCE: 28
aaagtgtttt atacagttca aatcagaaaa actacttggc                              40

<210> SEQ ID NO 29
<211> LENGTH: 40
<212> TYPE: DNA
<213> ORGANISM: Artificial
<220> FEATURE:
<223> OTHER INFORMATION: primer for PCR

<400> SEQUENCE: 29
ctggtttctg ctggtaccag gccaagtagt ttttctgatt                              40

<210> SEQ ID NO 30
<211> LENGTH: 40
<212> TYPE: DNA
<213> ORGANISM: Artificial

```
<220> FEATURE:
<223> OTHER INFORMATION: primer for PCR

<400> SEQUENCE: 30
ctggtaccag cagaaaccag ggcagcctcc taaactgctg                           40

<210> SEQ ID NO 31
<211> LENGTH: 40
<212> TYPE: DNA
<213> ORGANISM: Artificial
<220> FEATURE:
<223> OTHER INFORMATION: primer for PCR

<400> SEQUENCE: 31
ctagtggatg cccagtagat cagcagttta ggaggctgcc                           40

<210> SEQ ID NO 32
<211> LENGTH: 40
<212> TYPE: DNA
<213> ORGANISM: Artificial
<220> FEATURE:
<223> OTHER INFORMATION: primer for PCR

<400> SEQUENCE: 32
atctactggg catccactag ggaatctggt gtccctgatc                           40

<210> SEQ ID NO 33
<211> LENGTH: 40
<212> TYPE: DNA
<213> ORGANISM: Artificial
<220> FEATURE:
<223> OTHER INFORMATION: primer for PCR

<400> SEQUENCE: 33
agatccactg cctgagaagc gatcagggac accagattcc                           40

<210> SEQ ID NO 34
<211> LENGTH: 40
<212> TYPE: DNA
<213> ORGANISM: Artificial
<220> FEATURE:
<223> OTHER INFORMATION: primer for PCR

<400> SEQUENCE: 34
gcttctcagg cagtggatct gggacagatt ttactcttac                           40

<210> SEQ ID NO 35
<211> LENGTH: 40
<212> TYPE: DNA
<213> ORGANISM: Artificial
<220> FEATURE:
<223> OTHER INFORMATION: primer for PCR

<400> SEQUENCE: 35
cagcttgtag actgctgatg gtaagagtaa aatctgtccc                           40

<210> SEQ ID NO 36
<211> LENGTH: 40
<212> TYPE: DNA
<213> ORGANISM: Artificial
<220> FEATURE:
<223> OTHER INFORMATION: primer for PCR

<400> SEQUENCE: 36
catcagcagt ctacaagctg aagacgtggc agtttattac                           40
```

<210> SEQ ID NO 37
<211> LENGTH: 40
<212> TYPE: DNA
<213> ORGANISM: Artificial
<220> FEATURE:
<223> OTHER INFORMATION: primer for PCR

<400> SEQUENCE: 37
gaggagaaat attgatgaca gtaataaact gccacgtctt                    40

<210> SEQ ID NO 38
<211> LENGTH: 40
<212> TYPE: DNA
<213> ORGANISM: Artificial
<220> FEATURE:
<223> OTHER INFORMATION: primer for PCR

<400> SEQUENCE: 38
tgtcatcaat atttctcctc gtacacgttc ggacagggga                    40

<210> SEQ ID NO 39
<211> LENGTH: 57
<212> TYPE: DNA
<213> ORGANISM: Artificial
<220> FEATURE:
<223> OTHER INFORMATION: primer for PCR

<400> SEQUENCE: 39
tctagaaaaa agtacttacg ttttatttcc agcttggtcc cctgtccgaa cgtgtac    57

<210> SEQ ID NO 40
<211> LENGTH: 40
<212> TYPE: DNA
<213> ORGANISM: Artificial
<220> FEATURE:
<223> OTHER INFORMATION: primer for PCR

<400> SEQUENCE: 40
tataacgcgt ccaccatgga ctccaggctc aatttagttt                    40

<210> SEQ ID NO 41
<211> LENGTH: 40
<212> TYPE: DNA
<213> ORGANISM: Artificial
<220> FEATURE:
<223> OTHER INFORMATION: primer for PCR

<400> SEQUENCE: 41
ttttaaaata aggacaagga aaactaaatt gagcctggag                    40

<210> SEQ ID NO 42
<211> LENGTH: 40
<212> TYPE: DNA
<213> ORGANISM: Artificial
<220> FEATURE:
<223> OTHER INFORMATION: primer for PCR

<400> SEQUENCE: 42
tccttgtcct tattttaaaa ggtgtccagt gtgaggtcca                    40

<210> SEQ ID NO 43
<211> LENGTH: 40
<212> TYPE: DNA
<213> ORGANISM: Artificial
<220> FEATURE:
<223> OTHER INFORMATION: primer for PCR

<400> SEQUENCE: 43
cagctccaga ctgcaccagc tggacctcac actggacacc            40

<210> SEQ ID NO 44
<211> LENGTH: 40
<212> TYPE: DNA
<213> ORGANISM: Artificial
<220> FEATURE:
<223> OTHER INFORMATION: primer for PCR

<400> SEQUENCE: 44
gctggtgcag tctggagctg aggtgaaaaa gcctggggct            40

<210> SEQ ID NO 45
<211> LENGTH: 40
<212> TYPE: DNA
<213> ORGANISM: Artificial
<220> FEATURE:
<223> OTHER INFORMATION: primer for PCR

<400> SEQUENCE: 45
ttgcaggaga tcttcactgt agccccaggc ttttcacct            40

<210> SEQ ID NO 46
<211> LENGTH: 40
<212> TYPE: DNA
<213> ORGANISM: Artificial
<220> FEATURE:
<223> OTHER INFORMATION: primer for PCR

<400> SEQUENCE: 46
acagtgaaga tctcctgcaa ggtctctgga tacacattca            40

<210> SEQ ID NO 47
<211> LENGTH: 40
<212> TYPE: DNA
<213> ORGANISM: Artificial
<220> FEATURE:
<223> OTHER INFORMATION: primer for PCR

<400> SEQUENCE: 47
ccagtgcata acataactag tgaatgtgta tccagagacc            40

<210> SEQ ID NO 48
<211> LENGTH: 40
<212> TYPE: DNA
<213> ORGANISM: Artificial
<220> FEATURE:
<223> OTHER INFORMATION: primer for PCR

<400> SEQUENCE: 48
ctagttatgt tatgcactgg gttaggcagg cgcctgggaa            40

<210> SEQ ID NO 49
<211> LENGTH: 40
<212> TYPE: DNA
<213> ORGANISM: Artificial
<220> FEATURE:
<223> OTHER INFORMATION: primer for PCR

<400> SEQUENCE: 49
atccaatcca ctcaaggccc ttcccaggcg cctgcctaac            40

<210> SEQ ID NO 50

<211> LENGTH: 40
<212> TYPE: DNA
<213> ORGANISM: Artificial
<220> FEATURE:
<223> OTHER INFORMATION: primer for PCR

<400> SEQUENCE: 50
gggccttgag tggattggat atattactcc ttataatgat        40

<210> SEQ ID NO 51
<211> LENGTH: 40
<212> TYPE: DNA
<213> ORGANISM: Artificial
<220> FEATURE:
<223> OTHER INFORMATION: primer for PCR

<400> SEQUENCE: 51
ttctcattgt atttagtacc atcattataa ggagtaatat        40

<210> SEQ ID NO 52
<211> LENGTH: 40
<212> TYPE: DNA
<213> ORGANISM: Artificial
<220> FEATURE:
<223> OTHER INFORMATION: primer for PCR

<400> SEQUENCE: 52
ggtactaaat acaatgagaa gttcaaaggc aaggccacac        40

<210> SEQ ID NO 53
<211> LENGTH: 40
<212> TYPE: DNA
<213> ORGANISM: Artificial
<220> FEATURE:
<223> OTHER INFORMATION: primer for PCR

<400> SEQUENCE: 53
ggtggatttg tctgaagtca gtgtggcctt gcctttgaac        40

<210> SEQ ID NO 54
<211> LENGTH: 40
<212> TYPE: DNA
<213> ORGANISM: Artificial
<220> FEATURE:
<223> OTHER INFORMATION: primer for PCR

<400> SEQUENCE: 54
tgacttcaga caaatccacc gacacagcct acatggaact        40

<210> SEQ ID NO 55
<211> LENGTH: 40
<212> TYPE: DNA
<213> ORGANISM: Artificial
<220> FEATURE:
<223> OTHER INFORMATION: primer for PCR

<400> SEQUENCE: 55
cctcagagcg caggctgctg agttccatgt aggctgtgtc        40

<210> SEQ ID NO 56
<211> LENGTH: 40
<212> TYPE: DNA
<213> ORGANISM: Artificial
<220> FEATURE:
<223> OTHER INFORMATION: primer for PCR

<400> SEQUENCE: 56

```
cagcagcctg cgctctgagg acactgcggt ctattactgt                                40
```

<210> SEQ ID NO 57
<211> LENGTH: 40
<212> TYPE: DNA
<213> ORGANISM: Artificial
<220> FEATURE:
<223> OTHER INFORMATION: primer for PCR

<400> SEQUENCE: 57

```
tcgtatctac taccgtagac acagtaatag accgcagtgt                                40
```

<210> SEQ ID NO 58
<211> LENGTH: 40
<212> TYPE: DNA
<213> ORGANISM: Artificial
<220> FEATURE:
<223> OTHER INFORMATION: primer for PCR

<400> SEQUENCE: 58

```
gtctacggta gtagatacga ctggtacttc gatgtctggg                                40
```

<210> SEQ ID NO 59
<211> LENGTH: 40
<212> TYPE: DNA
<213> ORGANISM: Artificial
<220> FEATURE:
<223> OTHER INFORMATION: primer for PCR

<400> SEQUENCE: 59

```
ggtgacggtg gtcccttggc cccagacatc gaagtaccag                                40
```

<210> SEQ ID NO 60
<211> LENGTH: 40
<212> TYPE: DNA
<213> ORGANISM: Artificial
<220> FEATURE:
<223> OTHER INFORMATION: primer for PCR

<400> SEQUENCE: 60

```
gccaagggac caccgtcacc gtctcctcag gtaagaatgg                                40
```

<210> SEQ ID NO 61
<211> LENGTH: 34
<212> TYPE: DNA
<213> ORGANISM: Artificial
<220> FEATURE:
<223> OTHER INFORMATION: primer for PCR

<400> SEQUENCE: 61

```
tatatctaga gtggccattc ttacctgagg agac                                      34
```

<210> SEQ ID NO 62
<211> LENGTH: 23
<212> TYPE: PRT
<213> ORGANISM: Artificial
<220> FEATURE:
<223> OTHER INFORMATION: human acceptor for light chain, variable region

<400> SEQUENCE: 62

Asp Ile Val Met Thr Gln Ser Pro Asp Ser Leu Ala Val Ser Leu Gly
1               5                   10                  15

Glu Arg Ala Thr Ile Asn Cys
            20

```
<210> SEQ ID NO 63
<211> LENGTH: 30
<212> TYPE: PRT
<213> ORGANISM: Artificial
<220> FEATURE:
<223> OTHER INFORMATION: human acceptor for heavy chain, variable region

<400> SEQUENCE: 63

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Ile
            20                  25                  30

<210> SEQ ID NO 64
<211> LENGTH: 14
<212> TYPE: PRT
<213> ORGANISM: Artificial
<220> FEATURE:
<223> OTHER INFORMATION: human acceptor for heavy chain, variable region

<400> SEQUENCE: 64

Trp Val Gln Gln Val Pro Gly Lys Gly Leu Glu Trp Met Gly
1               5                   10

<210> SEQ ID NO 65
<211> LENGTH: 24
<212> TYPE: PRT
<213> ORGANISM: Artificial
<220> FEATURE:
<223> OTHER INFORMATION: human acceptor for heavy chain, variable region

<400> SEQUENCE: 65

Arg Val Thr Ile Thr Ala Asp Thr Ser Thr Asp Thr Ala Tyr Met Glu
1               5                   10                  15

Leu Gly Ser Leu Arg Ser Glu Asp
            20

<210> SEQ ID NO 66
<211> LENGTH: 8
<212> TYPE: PRT
<213> ORGANISM: Artificial
<220> FEATURE:
<223> OTHER INFORMATION: human acceptor heavy chain, variable region

<400> SEQUENCE: 66

Thr Ala Val Tyr Tyr Cys Ala Thr
1               5
```